United States Patent
Shlien et al.

(10) Patent No.: US 12,080,381 B2
(45) Date of Patent: Sep. 3, 2024

(54) SYSTEM AND METHOD FOR CANCER-CELL SPECIFIC TRANSCRIPTION IDENTIFICATION

(71) Applicant: THE HOSPITAL FOR SICK CHILDREN, Toronto (CA)

(72) Inventors: Adam Shlien, Toronto (CA); Matthew Zatzman, Toronto (CA)

(73) Assignee: THE HOSPITAL FOR SICK CHILDREN, Toronto (CA)

( * ) Notice: Subject to any disclaimer, the term of this patent is extended or adjusted under 35 U.S.C. 154(b) by 0 days.

(21) Appl. No.: 18/251,174

(22) PCT Filed: Nov. 5, 2021

(86) PCT No.: PCT/CA2021/051580
§ 371 (c)(1),
(2) Date: Apr. 28, 2023

(87) PCT Pub. No.: WO2022/094720
PCT Pub. Date: May 12, 2022

(65) Prior Publication Data
US 2023/0326550 A1 Oct. 12, 2023

Related U.S. Application Data

(60) Provisional application No. 63/203,458, filed on Jul. 23, 2021, provisional application No. 63/110,527, filed on Nov. 6, 2020.

(51) Int. Cl.
*G16B 20/20* (2019.01)
*G16B 20/10* (2019.01)
(Continued)

(52) U.S. Cl.
CPC .............. *G16B 20/20* (2019.02); *G16B 20/10* (2019.02); *G16B 40/20* (2019.02); *G16H 10/40* (2018.01); *G16H 50/70* (2018.01)

(58) Field of Classification Search
CPC ........ G16B 20/20; G16B 20/10; G16B 40/20; G16H 50/70
See application file for complete search history.

(56) References Cited

U.S. PATENT DOCUMENTS

| | | | |
|---|---|---|---|
| 10,233,495 B2 * | 3/2019 | Hatchwell | ............ C12Q 1/6883 |
| 2014/0161721 A1 * | 6/2014 | Hatchwell | ............ C12Q 1/6883 |
| | | | 424/1.49 |

(Continued)

OTHER PUBLICATIONS

International Search Report and Written Opinion of the International Searching Authority for PCT/CA2021/051580, mailing date Jan. 10, 2022.

(Continued)

*Primary Examiner* — Jay M. Patel
(74) *Attorney, Agent, or Firm* — Bhole IP Law; Anil Bhole; Mar Lampert

(57) ABSTRACT

The present invention relates a system and method for cancer-cell specific transcription identification. The method including: receiving nucleic acid data from one or more samples; determining variant allele fraction (VAF) of markers in ribonucleic acid (RNA) in the nucleic acid data and markers for deoxyribonucleic acid (DNA) in the nucleic acid data; comparing the VAF of the RNA relative to the DNA for each of the markers; and outputting the comparison as a quantification of cancer-cell specific changes in transcriptional output as a marker of prognosis or therapeutic response in cancer.

20 Claims, 46 Drawing Sheets

(51) Int. Cl.
  *G16B 40/20* (2019.01)
  *G16H 10/40* (2018.01)
  *G16H 50/70* (2018.01)

(56) References Cited

U.S. PATENT DOCUMENTS

2017/0202939 A1* 7/2017 Carreno ........... G01N 33/56977
2019/0194753 A1* 6/2019 Scherer .............. C07K 14/4728
2019/0241968 A1* 8/2019 Lee ..................... C12Q 1/6827
2020/0332365 A1* 10/2020 Tabori .................... A61P 35/00

OTHER PUBLICATIONS

Ma, Xiaotu , et al., "Pan-cancer genome and transcriptome analyses of 1,699 paediatric leukaemias and solid tumours", Nature, vol. 555, Mar. 15, 2018, Entire document.
Yizhak, Keren , et al., "RNA sequence analysis reveals macroscopic somatic clonal expansion across normal tissues", Science, 364(6444), Jun. 7, 2019, Entire document.
"An integrated encyclopedia of DNA elements in the human genome", Nature 489, 57-74 (2012). https://doi.org/10.1038/nature11247.
Aaltonen, Lauri A. , et al., "Pan-cancer analysis of whole genomes", (2020). Nature, 578(7793), 82-93. https://doi.org/10.1038/s41586-020-1969-6.
Ben-Porath, Ittai , et al., "An embryonic stem cell-like gene expression signature in poorly differentiated aggressive human tumors", Nat Genet 40, 499-507 (2008). https://doi.org/10.1038/ng.127.
Bielski, Craig M. , et al., "Genome doubling shapes the evolution and prognosis of advanced cancers", Nat Genet 50, 1189-1195 (2018). https://doi.org/10.1038/s41588-018-0165-1.
Campbell, Brittany B. , et al., "Comprehensive Analysis of Hypermutation in Human Cancer", (2017). Cell, 171(5). https://doi.org/10.1016/j.cell.2017.09.048.
Cao, Shaolong , et al., "Estimation of tumor cell total mRNA expression in 15 cancer types predicts disease progression", Nat Biotechnol 40, 1624-1633 (2022). https://doi.org/10.1038/s41587-022-01342-x.
Carter, Scott L. , et al., "Absolute quantification of somatic DNA alterations in human cancer", Nat Biotechnol 30, 413-421 (2012). https://doi.org/10.1038/nbt.2203.
Caspersson, T. , et al., "Pentose Nucleotides in the Cytoplasm of Growing Tissues", (1939). Nature, 143(3623), 602-603. https://doi.org/10.1038/143602c0.
Cherniack, Andrew D. , et al., "Integrated Molecular Characterization of Uterine Carcinosarcoma", (2017). Cancer Cell, 31(3), 411-423. https://doi.org/10.1016/j.ccell.2017.02.010.
Chow, Po-Ming , et al., "The covalent CDK7 inhibitor THZ1 enhances temsirolimus-induced cytotoxicity via autophagy suppression in human renal cell carcinoma", Cancer Letters, vol. 471, 2020, pp. 27-37, ISSN 0304-3835, https://doi.org/10.1016/j.canlet.2019.12.005.
Dobin, Alexander , et al., "STAR: ultrafast universal RNA-seq aligner", (2012). Bioinformatics, 29(1), 15-21. https://doi.org/10.1093/bioinformatics/bts635.
Eliezer M., Van Allen , et al., "Genomic correlates of response to CTLA-4 blockade in metastatic melanoma", (2015). Science, 350(6257), 207-211. https://doi.org/10.1126/science.aad0095.
Feng, Felix Y. , et al., "Molecular Pathways: Targeting ETS Gene Fusions in Cancer", (2014). Clinical Cancer Research, 20(17), 4442-4448. https://doi.org/10.1158/1078-0432.ccr-13-0275.
Gao, Qingsong , et al., "Driver Fusions and Their Implications in the Development and Treatment of Human Cancers", (2018). Cell Reports, 23(1). https://doi.org/10.1016/j.celrep.2018.03.050.
Gonda, Thomas J. , et al., "Directly targeting transcriptional dysregulation in cancer", (2015). Nature Reviews Cancer, 15(11), 686-694. https://doi.org/10.1038/nrc4018.
Goodman, Aaron M. , et al., "Tumor Mutational Burden as an Independent Predictor of Response to Immunotherapy in Diverse Cancers", (2017). Molecular Cancer Therapeutics, 16(11), 2598-2608. https://doi.org/10.1158/1535-7163.mct-17-0386.
Greenall, SA , et al., "Cyclin-dependent kinase 7 is a therapeutic target in high-grade glioma", Oncogenesis 6, e336 (2017). https://doi.org/10.1038/oncsis.2017.33.
Grömping, Ulrike , "Relative Importance for Linear Regression in R: The Package relaimpo", (2006). Journal of Statistical Software, 17(1). https://doi.org/10.18637/jss.v017.i01.
Han, Heonjong , et al., "TRRUST: a reference database of human transcriptional regulatory interactions", Sci Rep 5, 11432 (2015). https://doi.org/10.1038/srep11432.
Hänzelmann, Sonja, et al., "GSVA: gene set variation analysis for microarray and RNA-Seq data", BMC Bioinformatics 14, 7 (2013). https://doi.org/10.1186/1471-2105-14-7.
Huang, Annie , et al., "Identification of a Novel c-Myc Protein Interactor, JPO2, with Transforming Activity in Medulloblastoma Cells", (2005). Cancer Research, 65(13), 5607-5619. https://doi.org/10.1158/0008-5472.can-05-0500.
Hugo, Willy , et al., "Genomic and Transcriptomic Features of Response to Anti-PD-1 Therapy in Metastatic Melanoma", (2016). Cell, 165(1), 35-44. https://doi.org/10.1016/j.cell.2016.02.065.
Iniguez, Amanda Balboni, et al., "EWS/FLI Confers Tumor Cell Synthetic Lethality to CDK12 Inhibition in Ewing Sarcoma", (2018). Cancer Cell, 33(2). https://doi.org/10.1016/j.ccell.2017.12.009.
Jiang, Lichun , et al., "Synthetic spike-in standards for RNA-seq experiments", Genome Research, 21(9), 1543-1551. https://doi.org/10.1101/gr.121095.111.
Jiang, C. , et al., "TRED: a transcriptional regulatory element database, new entries and other development", (2007). Nucleic Acids Research, 35(Database). https://doi.org/10.1093/nar/gkl1041.
Kim, Jonghwan , et al., "A Myc Network Accounts for Similarities between Embryonic Stem and Cancer Cell Transcription Programs", (2010). Cell, 143(2), 313-324. https://doi.org/10.1016/j.cell.2010.09.010.
Kwiatkowski, Nicholas , et al., "Targeting transcription regulation in cancer with a covalent CDK7 inhibitor", Nature 511, 616-620 (2014). https://doi.org/10.1038/nature13393.
Lachmann, Alexander , et al., "ChEA: transcription factor regulation inferred from integrating genome-wide ChIP-X experiments", (2010). Bioinformatics, 26(19), 2438-2444. https://doi.org/10.1093/bioinformatics/btq466.
Lambrechts, Diether , et al., "Phenotype molding of stromal cells in the lung tumor microenvironment", Nat Med 24, 1277-1289 (2018). https://doi.org/10.1038/s41591-018-0096-5.
Li, Yilong , et al., "Patterns of somatic structural variation in human cancer genomes", Nature 578, 112-121 (2020). https://doi.org/10.1038/s41586-019-1913-9.
Liberzon, Arthur , et al., "The Molecular Signatures Database Hallmark Gene Set Collection", (2015). Cell Systems, 1(6), 417-425. https://doi.org/10.1016/j.cels.2015.12.004.
Lin, Charles Y. , et al., "Transcriptional Amplification in Tumor Cells with Elevated c-Myc", (2012). Cell, 151(1), 56-67. https://doi.org/10.1016/j.cell.2012.08.026.
Liu, Jianfang , et al., "An Integrated TCGA Pan-Cancer Clinical Data Resource to Drive High-Quality Survival Outcome Analytics", (2018). Cell, 173(2). https://doi.org/10.1016/j.cell.2018.02.052.
Liu, David , et al., "Integrative molecular and clinical modeling of clinical outcomes to PD1 blockade in patients with metastatic melanoma", Nat Med 25, 1916-1927 (2019). https://doi.org/10.1038/s41591-019-0654-5.
López-Ratón, Mónica , et al., "OptimalCutpoints: An R Package for Selecting Optimal Cutpoints in Diagnostic Tests", (2014). Journal of Statistical Software, 61(8). https://doi.org/10.18637/jss.v061.i08.
Lovén, Jakob , et al., "Revisiting Global Gene Expression Analysis", (2012). Cell, 151(3), 476-482. https://doi.org/10.1016/j.cell.2012.10.012.
Lu, Ping , et al., "THZ1 reveals CDK7-dependent transcriptional addictions in pancreatic cancer", Oncogene 38, 3932-3945 (2019). https://doi.org/10.1038/s41388-019-0701-1.
Malta, Tathiane M. , et al., "Machine Learning Identifies Stemness Features Associated with Oncogenic Dedifferentiation", (2018). Cell, 173(2). https://doi.org/10.1016/j.cell.2018.03.034.

(56) References Cited

OTHER PUBLICATIONS

Matys, V., et al., "TRANSFAC(R) and its module transcompel(r): Transcriptional gene regulation in eukaryotes", (2006). Nucleic Acids Research, 34(90001). https://doi.org/10.1093/nar/gkj143.
McDermott, Martina S. J., et al., "CDK7 Inhibition Is Effective in all the Subtypes of Breast Cancer: Determinants of Response and Synergy with EGFR Inhibition", (2020). Cells, 9(3), 638. https://doi.org/10.3390/cells9030638.
Meng, Wei, et al., "CDK7 inhibition is a novel therapeutic strategy against GBM both in vitro and in vivo", (2018). Cancer Management and Research, vol. 10, 5747-5758. https://doi.org/10.2147/cmar.s183696.
Mossmann, Dirk, et al., "mTOR signalling and cellular metabolism are mutual determinants in cancer", Nat Rev Cancer 18, 744-757 (2018). https://doi.org/10.1038/s41568-018-0074-8.
Nik-Zainal, Serena, et al., "Mutational Processes Molding the Genomes of 21 Breast Cancers", (2012). Cell, 149(5), 979-993. https://doi.org/10.1016/j.cell.2012.04.024.
Palmer, Nathan P., et al., "A gene expression profile of stem cell pluripotentiality and differentiation is conserved across diverse solid and hematopoietic cancers", (2012). Genome Biology, 13(8). https://doi.org/10.1186/gb-2012-13-8-r71.
Pavlova, Natalya N., et al., "The Emerging Hallmarks of Cancer Metabolism", (2016). Cell Metabolism, 23(1), 27-47. https://doi.org/10.1016/j.cmet.2015.12.006.
Percharde, Michelle, et al., "Global Hypertranscription in the Mouse Embryonic Germline", Cell Reports, 19(10), 1987-1996. https://doi.org/10.1016/j.celrep.2017.05.036.
Percharde, Michelle, et al., "Hypertranscription in Development, Stem Cells, and Regeneration", (2017). Developmental Cell, 40(1), 9-21. https://doi.org/10.1016/j.devcel.2016.11.010.
Petermann, M. L., "The nucleic acid distribution in normal and leukemic mouse spleen", (1949). Cancer, 2(3), 510-515. https://doi.org/10.1002/1097-0142(194905)2:3lt;510::aid-cncr2820020315gt;3.0.co;2-9.
Peters, Jeffrey M., et al., "The role of peroxisome proliferator-activated receptors in carcinogenesis and chemoprevention", Nat Rev Cancer 12, 181-195 (2012). https://doi.org/10.1038/nrc3214.
Rasmussen, Markus, et al., "Allele-specific copy number analysis of tumor samples with aneuploidy and tumor heterogeneity", (2011). Genome Biology, 12(10). https://doi.org/10.1186/gb-2011-12-10-r108.
Rehman, Sumaiyah K., et al., "Colorectal Cancer Cells Enter a Diapause-like DTP State to Survive Chemotherapy", (2021). Cell, 184(1). https://doi.org/10.1016/j.cell.2020.11.018.
Riaz, Nadeem, et al., "Tumor and Microenvironment Evolution during Immunotherapy with Nivolumab", (2017). Cell, 171(4), 934-949. https://doi.org/10.1016/j.cell.2017.09.028.
Robinson, Mark D., et al., "edgeR: a Bioconductor package for differential expression analysis of digital gene expression data", Bioinformatics, vol. 26, Issue 1, Jan. 2010, pp. 139-140, https://doi.org/10.1093/bioinformatics/btp616.
Sabò, Arianna, et al., "Selective transcriptional regulation by Myc in cellular growth control and lymphomagenesis", (2014). Nature, 511(7510), 488-492. https://doi.org/10.1038/nature13537.
Schaub, Franz X., et al., "Pan-cancer Alterations of the MYC Oncogene and Its Proximal Network across the Cancer Genome Atlas", (2018). Cell Systems, 6(3). https://doi.org/10.1016/j.cels.2018.03.003.
Shen, Ronglai, et al., "FACETS: allele-specific copy number and clonal heterogeneity analysis tool for high-throughput DNA sequencing", Nucleic Acids Research, vol. 44, Issue 16, Sep. 19, 2016, p. e131, https://doi.org/10.1093/nar/gkw520.
Shlien, Adam, et al., "Direct Transcriptional Consequences of Somatic Mutation in Breast Cancer", (2016). Direct transcriptional consequences of somatic mutation in breast cancer. Cell Reports, 16(7), 2032-2046. https://doi.org/10.1016/j.celrep.2016.07.028.
Smid, Marcel, et al., "Gene length corrected trimmed mean of M-values (GeTMM) processing of RNA-seq data performs similarly in intersample analyses while improving intrasample comparisons", BMC Bioinformatics 19, 236 (2018). https://doi.org/10.1186/s12859-018-2246-7.
Taniguchi, Koji, et al., "NF B, inflammation, immunity and cancer: coming of age", Nat Rev Immunol 18, 309-324 (2018). https://doi.org/10.1038/nri.2017.142.
Wang, Cun, et al., "A CRISPR screen identifies CDK7 as a therapeutic target in hepatocellular carcinoma", Cell Res 28, 690-692 (2018). https://doi.org/10.1038/s41422-018-0020-z.
Wang, Jian, et al., "Antitumor effects of a covalent cyclin-dependent kinase 7 inhibitor in colorectal cancer", (2019). Anti-Cancer Drugs, 30(5), 466-474. https://doi.org/10.1097/cad.0000000000000749.
Wong, David J., et al., "Module Map of Stem Cell Genes Guides Creation of Epithelial Cancer Stem Cells".
Yan, Xiaowei, et al., "A CD133-related gene expression signature identifies an aggressive glioblastoma subtype with excessive mutations", (2011). Proceedings of the National Academy of Sciences, 108(4), 1591-1596. https://doi.org/10.1073/pnas.1018696108.
Yarchoan, Mark, et al., "Tumor Mutational Burden and Response Rate to PD-1 Inhibition", (2017). New England Journal of Medicine, 377(25), 2500-2501. https://doi.org/10.1056/nejmc1713444.
Zack, Travis I, et al., "Pan-cancer patterns of somatic copy No. alteration", Nat Genet 45, 1134-1140 (2013). https://doi.org/10.1038/ng.2760.
Zhang, Wei, et al., "Combinational therapeutic targeting of BRD4 and CDK7 synergistically induces anticancer effects in head and neck squamous cell carcinoma", Cancer Letters, vol. 469, 2020, pp. 510-523, ISSN 0304-3835, https://doi.org/10.1016/j.canlet.2019.11.027.
Zhang, Zhenfeng, et al., "Preclinical Efficacy and Molecular Mechanism of Targeting CDK7-Dependent Transcriptional Addiction in Ovarian Cancer", (2017). Molecular Cancer Therapeutics, 16(9), 1739-1750. https://doi.org/10.1158/1535-7163.mct-17-0078.
Zhong, Shanshan, et al., "CDK7 inhibitor suppresses tumor progression through blocking the cell cycle at the G2/M phase and inhibiting transcriptional activity in cervical cancer", Onco Targets Ther. 2019;12:2137-2147. https://doi.org/10.2147/OTT.S195655.
Zhong, Liqiang, et al., "Inhibition of cyclin-dependent kinase 7 suppresses human hepatocellular carcinoma by inducing apoptosis", (2018). Journal of Cellular Biochemistry, 119(12), 9742-9751. https://doi.org/10.1002/jcb.27292.

\* cited by examiner

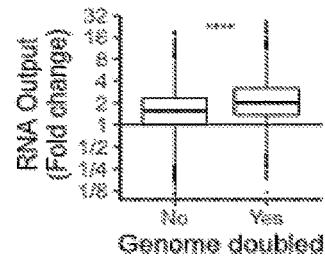
FIG. 7A
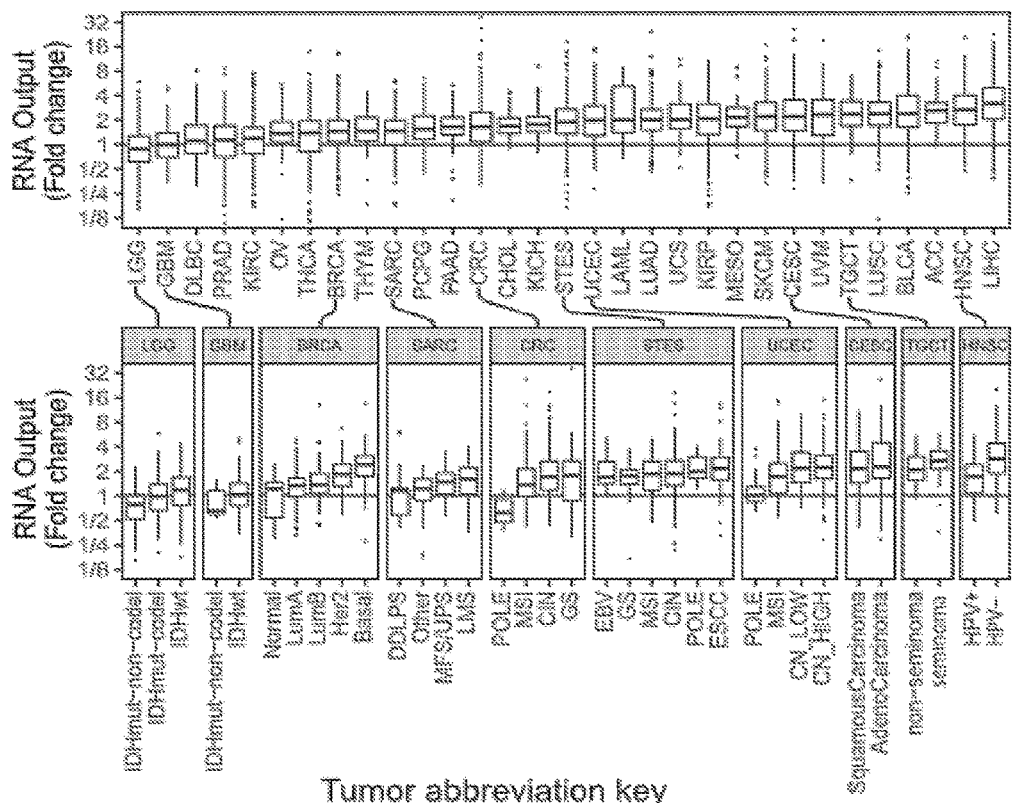
FIG. 7B
FIG. 7C

Variability explained

Variable
- Purity
- Ploidy
- Mutation burden
- Tumor type
- Unexplained
- Tumor Stage
- Age
- Gender
- Tumor subtype Hypertranscription — Low — High Hypertranscription — Low — High Hypertranscription — Low — High

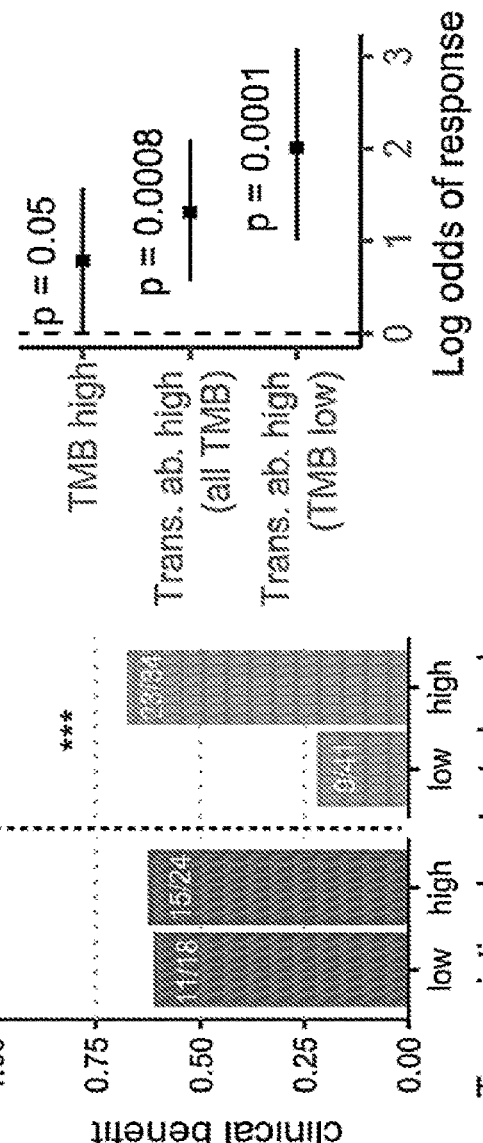
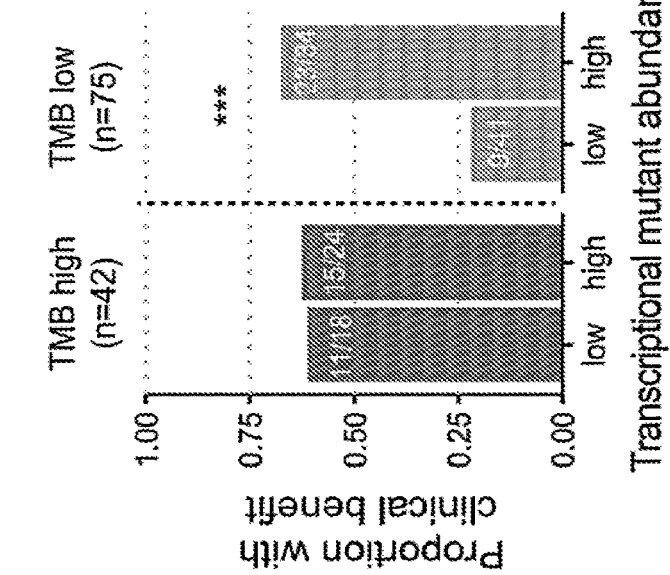
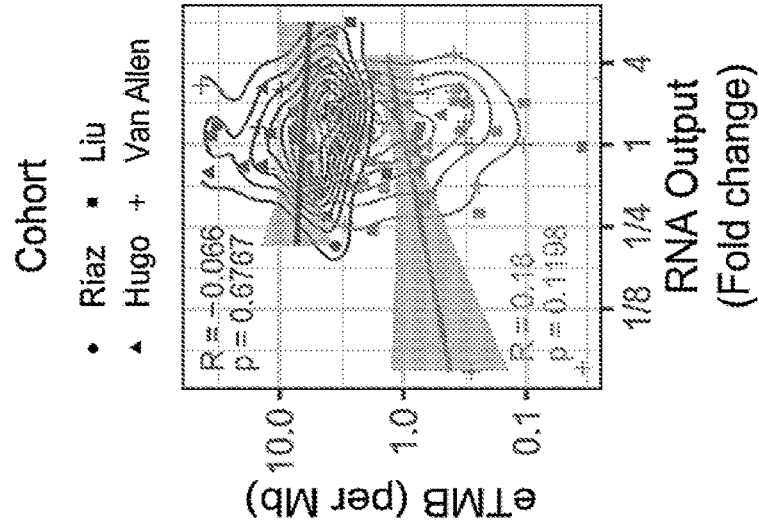
FIG. 20A
FIG. 20B
FIG. 20C

SYSTEM AND METHOD FOR CANCER-CELL SPECIFIC TRANSCRIPTION IDENTIFICATION

The present invention relates to nucleic acid analysis; and more particularly, to a system and method for cancer-cell specific transcription identification.

BACKGROUND

Global increase in the production of ribonucleic acid (RNA) from all genes has been described in a limited number of cell line models. This phenomenon, also called 'transcriptional amplification' or 'hypertranscription', is thought to play a direct role in driving cancer cell proliferation in these models. Specific oncogenes, including MYC, mediate transcriptional amplification directly or indirectly via downstream targets. However, because transcriptional amplification has generally not been explored in primary human cancers, many of its fundamental properties are unknown.

For solid tumors, they are typically preserved as bulk tissue, which is comprised of an unknown number of cells. Without knowing the number of cells from which the nucleic acid was extracted, it is generally not possible to measure RNA content per cell. Likewise, many tumor specimens are made up of multiple genetically distinct cell populations, which also includes an unknown amount of stromal (i.e., normal cell) contamination. Once homogenized, the tumor cells' contribution to the total RNA pool becomes unknown.

It is therefore an object of the present invention to provide a system and method in which the above disadvantages are obviated or mitigated, and attainment of various desirable attributes is facilitated.

SUMMARY

In an aspect, there is provided a computer-implemented method for cancer-cell specific transcription identification, the method comprising: receiving nucleic acid data from one or more samples; determining variant allele fraction (VAF) of markers in ribonucleic acid (RNA) in the nucleic acid data and markers for deoxyribonucleic acid (DNA) in the nucleic acid data; comparing the VAF of the RNA relative to the DNA for each of the markers; and outputting the comparison as a quantification of cancer-cell specific changes in transcriptional output as a marker of prognosis or therapeutic response in cancer.

In a particular case of the method, comparing the VAF of the RNA relative to the DNA for each of the markers comprises determining, a VAF difference, a VAF ratio, and an allelic ratio.

In another case of the method, the quantification of cancer-cell specific changes in transcriptional output comprises outputting no elevation in cancer global transcription when the VAF indicates that the markers in the RNA and the DNA are similar, and outputting elevation in cancer global transcription when the VAF indicates that the markers in the RNA are elevated relative to the markers in the DNA.

In yet another case of the method, the samples comprise both cancer cells and normal cells, and wherein determining the VAF in the RNA comprises measuring the cancer cells total RNA output and measuring the normal cells total RNA output.

In yet another case of the method, the method further comprising determining a relative fold amplification of tumor cells versus normal cells, and wherein the outputting further comprising outputting the relative fold amplification as a proportion of tumor derived RNA.

In yet another case of the method, the markers comprise somatic single nucleotide substitutions and single nucleotide polymorphisms (SNP) in regions of loss-of-heterozygosity (LOH-SNPs).

In yet another case of the method, the one or more samples come from human tumors whose RNA was derived from bulk tissue.

In yet another case of the method, the method further comprising determining expressed mutation burden due to the quantification of cancer-cell specific changes in transcriptional output for identification of patients that would respond to immune checkpoint inhibitor (ICI) therapy.

In yet another case of the method, the method further comprising determining an adjusted genomic tumor mutation burden (TMB) value based on the expressed TMB using a linear regression model with the expressed TMB as a predictor variable and genomic TMB as an outcome variable.

In yet another case of the method, the method further comprising using the quantification of cancer-cell specific changes in transcriptional output to identify patients with non-hypermutant tumors that would respond to immunotherapy.

In another aspect, there is provided a system for cancer-cell specific transcription identification, the system comprising one or more processors and a data storage, the one or more processors receiving instructions from the data storage to execute: an input module to receive nucleic acid data from one or more samples; a comparison module to determine variant allele fraction (VAF) of markers in ribonucleic acid (RNA) in the nucleic acid data and markers for deoxyribonucleic acid (DNA) in the nucleic acid data, and to compare the VAF of the RNA relative to the DNA for each of the markers; and an output module to output the comparison as a quantification of cancer-cell specific changes in transcriptional output as a marker of prognosis or therapeutic response in cancer.

In a particular case of the system, comparing the VAF of the RNA relative to the DNA for each of the markers comprises determining, a VAF difference, a VAF ratio, and an allelic ratio.

In another case of the system, the quantification of cancer-cell specific changes in transcriptional output comprises outputting no elevation in cancer global transcription when the VAF indicates that the markers in the RNA and the DNA are similar, and outputting elevation in cancer global transcription when the VAF indicates that the markers in the RNA are elevated relative to the markers in the DNA.

In yet another case of the system, the samples comprise both cancer cells and normal cells, and wherein determining the VAF in the RNA comprises measuring the cancer cells total RNA output and measuring the normal cells total RNA output.

In yet another case of the system, the system further comprising an amplification module to determine a relative fold amplification of tumor cells versus normal cells, and wherein the outputting further comprising outputting the relative fold amplification as a proportion of tumor derived RNA.

In yet another case of the system, the markers comprise somatic single nucleotide substitutions and single nucleotide polymorphisms in regions of loss-of-heterozygosity (LOH-SNPs).

In yet another case of the system, the one or more samples come from human tumors whose RNA was derived from bulk tissue.

In yet another case of the system, the output module further determining expressed mutation burden due to the quantification of cancer-cell specific changes in transcriptional output for identification of patients that would respond to immune checkpoint inhibitor (ICI) therapy.

In yet another case of the system, the output module further determining an adjusted genomic tumor mutation burden (TMB) value based on the expressed TMB using a linear regression model with the expressed TMB as a predictor variable and genomic TMB as an outcome variable.

In yet another case of the system, the output module further using the quantification of cancer-cell specific changes in transcriptional output to identify patients with non-hypermutant tumors that would respond to immunotherapy.

These and other aspects are contemplated and described herein. The foregoing summary sets out representative aspects of systems and methods to assist skilled readers in understanding the following detailed description.

DESCRIPTION OF THE DRAWINGS

An embodiment of the present invention will now be described by way of example only with reference to the accompanying drawings, in which:

FIG. 7A shows a diagram of an example of RNA amplification levels of cancers grouped by whether the tumors have undergone whole genome doubling;

FIG. 7B shows a diagram of an example of fold amplification levels of cancers by their tumor type;

FIG. 7C shows a diagram of an example of fold amplification levels of selected cancer types by their subtype;

FIG. 10 shows proportion of variability explained in specific tumor types, including hallmark pathway expression;

FIGS. 13A to 16 show an example showing hypertranscription defining patient subgroups with worse overall survival, where FIG. 13A shows uterus carcinosarcoma, FIG. 15 shows luminal A breast cancer, and FIG. shows HPV+ head and neck squamous cell carcinoma;

FIG. 20A shows a diagram of a correlation between between eTMB and hypertranscription for hypermutant (>10 mut/Mb) and non-hypermutant tumors (<10 mut/Mb) in four melanoma ICI cohorts;

FIG. 20B shows a diagram of proportion of patients with clinical benefit from ICI in high and low TMB groups split by transcriptional mutant abundance levels;

FIG. 20C shows a diagram of log odds of response to ICI for different tumor mutation burden markers;

DETAILED DESCRIPTION

Figure 1:
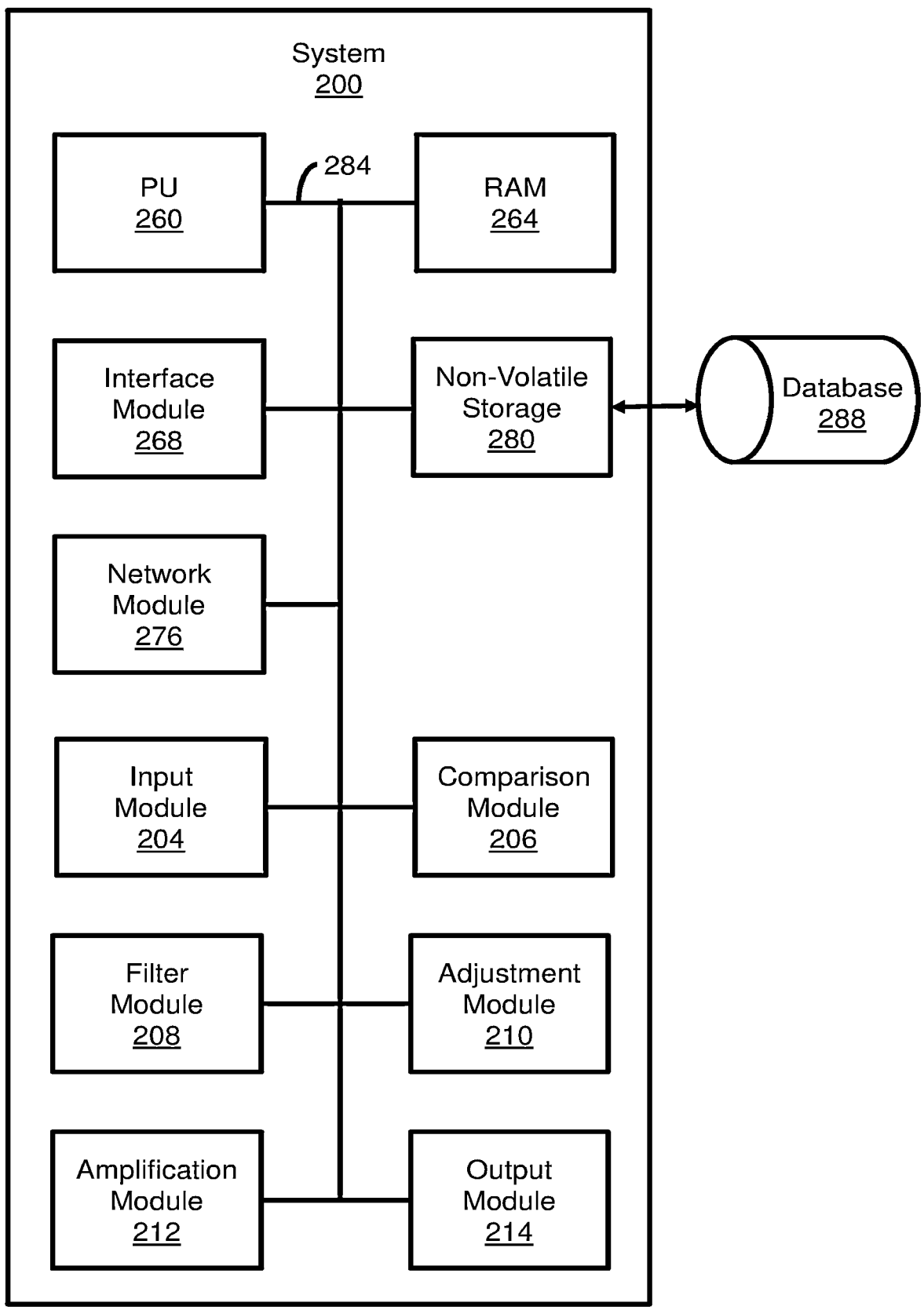
FIG. 1 is a block diagram showing a system for cancer-cell specific transcription identification, according to an embodiment.

Embodiments will now be described with reference to the figures. For simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Any module, unit, component, server, computer, computing device, mechanism, terminal or other device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Any application or module herein described may be implemented using computer readable/executable instructions that may be stored or otherwise held by such computer readable media and executed by the one or more processors.

The present invention relates to ribonucleic acid (RNA) analysis; and more particularly, to a system and method for cancer-cell specific transcription identification.

Observations have associated variable RNA levels with proliferation rates in different cell types. For example, early work in a mouse model of leukemia demonstrated that the RNA content of rapidly proliferating transplanted cells is greater than either normal cells or of that of slower growing spontaneous leukemias (4.2-fold vs. 1.6-fold above normal respectively). Therefore, the available data, while limited, suggests that cells that globally increase transcription have a growth advantage over those that cannot.

Studies have shown that cancer cells are reliant, or even 'addicted', to their gene expression programs; which provides advancement in targeting transcription. The analysis of transcriptional output in primary tumors is technically challenging. Using a focused approach, the present embodiments were used to observe the prevalence and consequences of transcriptional amplification across human cancer. The present inventors performed example experiments using the present embodiments to measure transcriptional output of 7,494 cancer samples from 31 cancer types, finding that cancer cells are universally more transcriptionally active than their surrounding stromal cells. Strikingly, specific tumor types and subtypes exhibit >4-fold higher transcriptional output. For some cancers, transcriptional output is completely explained by their molecular subtype plus gene expression programs, while for other tumor types the drivers of transcriptional output are unknown. Transcriptional amplification was determined to be an independent prognostic marker for disease outcomes across multiple cancer types. It was further determined that patients whose tumors are "amplified" express more mutations and appear to respond better to immune checkpoint inhibition.

Once homogenized, tumor cells' contribution to the total RNA pool generally becomes unknown. To measure cancer cell specific transcriptional output, a person would need to perform cell sorting (to account for normal cell contamination), then normalize for the number of cells, as well as use RNA spike-in controls mixed into the sequencing run itself. Even if these additional steps were technically feasible for ongoing specimens (without destroying the RNA), they have not been used by most publicly available RNA-sequencing datasets, which includes the nearly 10,000 tumor samples from The Cancer Genome Atlas (TCGA).

To overcome these challenges, in some cases, the present embodiments can use somatic single nucleotide substitutions (subs) and single nucleotide polymorphisms (SNP) in regions of loss-of-heterozygosity (LOH-SNPs) as markers of cancer-cell specific transcription. By quantifying the relative proportion of sequencing reads supporting these marker variants in both the DNA and RNA, the levels of transcriptional output of cancer cells in a primary tumor sample can be assessed. These metrics can be combined to derive a final value of transcriptional output levels.

FIG. 1 illustrates a schematic diagram of a system 200 for cancer-cell specific transcription identification (informally referred to as "RNAmp"), according to an embodiment. As shown, the system 200 has a number of physical and logical components, including a processing unit ("PU") 260, random access memory ("RAM") 264, an interface module 268, a network module 276, non-volatile storage 280, and a local bus 284 enabling PU 260 to communicate with the other components. PU 260 can include one or more processors. RAM provides relatively responsive volatile storage to PU 260. In some cases, the system 200 can be in communication with a device, for example, a nucleic acid sequencer, via, for example, the interface module 268. The interface module 268 enables input to be provided; for example, directly via a user input device, or indirectly, for example, via an external device. The interface module 268 also enables output to be provided; for example, directly via a user display, or indirectly, for example, sent over the network module 276. The network module 276 permits communication with other systems or computing devices; for example, over a local area network or over the Internet. Non-volatile storage 280 can store an operating system and programs, including computer-executable instructions for implementing the methods described herein, as well as any derivative or related data. In some cases, this data can be stored in a database 288. During operation of the system 200, the operating system, the programs and the data may be retrieved from the non-volatile storage 280 and placed in RAM 264 to facilitate execution. In other embodiments, any operating system, programs, or instructions can be executed in hardware, specialized microprocessors, logic arrays, or the like.

In an embodiment, the PU 260 can be configured to execute an input module 204, a comparison module 206, a filter module 208, an adjustment module 210, an amplification module 212, and an output module 214. In further cases, functions of the above modules can be combined or executed on other modules. In some cases, functions of the above modules can be executed on remote computing devices, such as centralized servers and cloud computing resources communicating over the network module 276.

Figure 2:
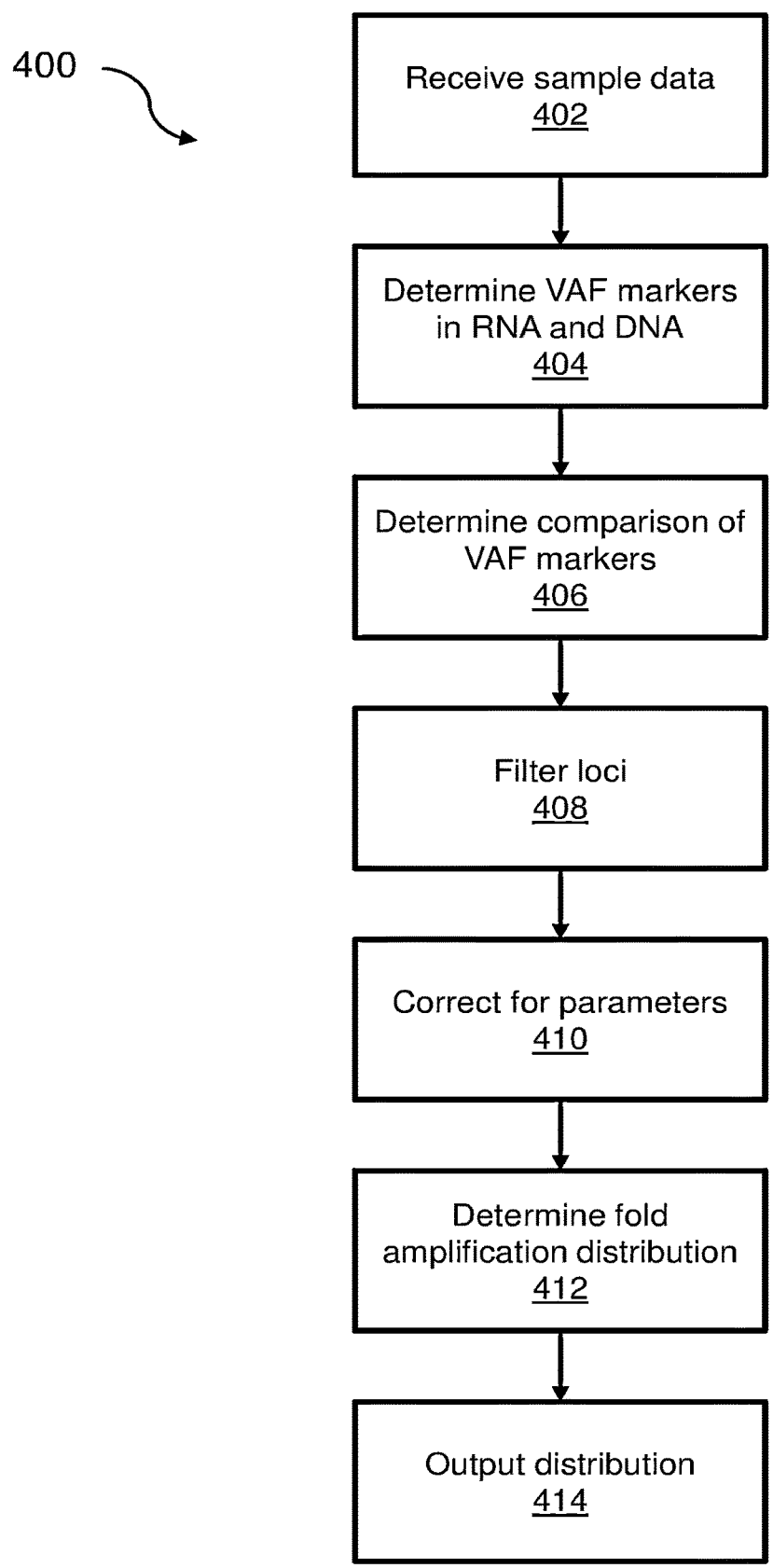
FIG. 2 is a flow chart showing a method for cancer-cell specific transcription identification, according to an embodiment.

Turning to FIG. 2, a method for cancer-cell specific transcription identification 400 is shown. At block 402, the input module 204 receives nucleic acid data from one or more samples. In some cases, for greater accuracy, the received nucleic acid data comprises sequence data of all coding genes in both DNA and RNA of the tumor. In some cases, this sequencing can be done by exome (or genome) and full transcriptome (also referred to as RNA-Seq), respectively. In other cases, where accuracy is less important, the received nucleic acid data comprises only RNA data for sequencing or only a subset of the genes are assessed. In either case, once the sequencing is complete, somatic variants, including substitutions and copy number changes, in the DNA can be determined using appropriate approaches; in some cases, followed by quality control filters. The resulting high-quality variants comprise the nucleic acid data from the one or more samples that is received by the input module 204. In other cases, the input module 204 can receive already sequenced tumors for which either raw data is available in a suitable format or comprises a list of high-quality variants.

At block 404, the comparison module 206 determines variant allele fraction (VAF) of markers in ribonucleic acid (RNA) in the nucleic acid data and markers for deoxyribonucleic acid (DNA) in the nucleic acid data. At block 406, the comparison module 206 compares the VAF of the RNA relative to the DNA. This comparison provides quantification of cancer-cell specific changes in transcriptional output. The variant allele fraction (VAF) of a mutation represents the proportion of reads in a next generation sequencing that support the presence of that variant, divided by the total number of reads at that same position. In most cases, it can generally be assumed that all of the variant reads are derived from tumor DNA, not the surrounding non-tumor material. There are multiple somatic processes that can impact the VAF. For example, regions of the DNA may be duplicated, which can lead to a higher VAF in that region. Advantageously, the present embodiments provide a comparison between the expected VAF (from DNA sequencing) and the observed VAF (in RNA-Seq) for variants in a given tumor. When the RNA has been globally amplified, the VAF of most variants as measured in RNA-Seq will be increased compared to the DNA.

At block 408, in some cases, the filter module 208 removes loci in imprinted regions and/or loci associated with unexpressed variants from the comparison output. In an example implementation, as part of example experiments conducted by the present inventors, allele-counting was performed on variant sites for each sample using GenomeAnalysisToolkit's ASEReadCounter on matched exome and RNA-sequencing data. Minimum read mapping quality and minimum base quality was set to 10 and 2 respectively. Depth downsampling was turned off. SNPs determined to be heterozygous in the germline, but where over 97.5% of DNA reads supported a single allele in the tumor, were removed due to the likelihood that these were misidentified homozygous loci. Likewise, germline variants in imprinted loci, where over 97.5% of RNA reads supported a single allele, were identified and removed.

At block 410, in some cases, the adjustment module 210 corrects for one or more parameters; for example, sample purity, sample ploidy, and local variant DNA copy number. Various features (for example, ploidy, etc.) may alter the VAF of the DNA in the impacted regions of the genome; which may then also impact the VAFs of the same variants when measured in the RNA. The present embodiments, as described herein, advantageously correct for the features of the genome that alter the VAF, such that any excess in VAF RNA can be due to transcriptional amplification.

At block 412, the amplification module 212 determines fold amplification distribution per sample. This distribution is associated with cancer-cell specific transcription identification.

At block 414, the output module 214 outputs the fold amplification distribution and/or the VAF comparison.

In some cases, as part of the output at 414, the output module can further determine expressed mutation burden due to the quantification of cancer-cell specific changes in transcriptional output for identification of patients that would respond to immune checkpoint inhibitor (ICI) therapy. In some cases, the output module can further determine an adjusted genomic tumor mutation burden (TMB) value based on the expressed TMB using a linear regression model with the expressed TMB as a predictor variable and genomic TMB as an outcome variable. In further cases, the output module can use the quantification of cancer-cell specific changes in transcriptional output to identify patients with non-hypermutant tumors that would respond to immunotherapy.

The inherent challenges of analyzing transcriptional output are addressed by the system 200 by using knowledge of cancers with globally elevated transcription and quantifying their RNA output compared to non-neoplastic cells (expressed as a fold change). Advantageously, the system 200 can analyze already-sequenced human tumors (usually genetically heterogenous and often non-diploid) whose RNA was derived from bulk tissue comprised of an unknown number of cells.

The RNA fraction ($VAF_{RNA}$) of a given mutation (i) at locus l is predicted by dividing the number of mutant RNA transcripts produced per tumor cell at a given locus by the total number of RNA transcripts (mutant and non-mutant) produced from that locus by both cancer or normal cells:

$$VAF_{RNA_{(i,l)}} = \frac{\text{Mutant } RNA \text{ copies}_{(i,l)}}{\text{Total } RNA \text{ Copies}_{(l)}} \quad (1)$$

For a mutation with copy number, $C_M$ in a tumor of a purity, p, local tumor total copy number $C_T$, and with normal copy number, $C_N$, the RNA fraction can be approximated if the level of transcriptional amplification (amp) at locus l is known:

$$VAF_{RNA_{(i,l)}} \approx \frac{C_{M_{(i,l)}} * amp_{(l)}}{\left(C_{T_{(l)}} * amp_{(l)}\right) + \left(C_{N_{(l)}} * \left(\frac{1-p}{p}\right)\right)} \quad (2)$$

where $C_M$*amp represents the number of RNA copies produced from chromosomes harbouring the mutated allele per cancer cell, $C_T$*amp represents the number of RNA copies produced from both mutant and normal chromosomal alleles per cancer cell and $$C_N * \left(\frac{1-p}{p}\right)$$

represents the number of RNA copies produced per contaminating normal cell.

The mutation copy number (number of chromosomal alleles harbouring the mutation per cancer cell) is given by:

$$C_{M_{(i,l)}} = \frac{VAF_{DNA_{(i,l)}}}{p} * \left(\left(p * C_{T_{(l)}}\right) + C_{N_{(l)}} * (1-p)\right) \quad (3)$$

Substituting Equation (3) into Equation (2) and rearranging to solve for amp gives:

$$amp_{(i,l)} \approx \frac{VAF_{RNA_{(i,l)}} * C_{N_{(l)}}(1-p)}{VAF_{DNA_{(i,l)}} * C_{N_{(l)}}(1-p) - pC_{T_{(l)}}\left(VAF_{RNA_{(i,l)}} - VAF_{DNA_{(i,l)}}\right)} \quad (4)$$

The RNA fraction ($VAF_{RNA}$) of a given LOH SNP (i) at locus l can be predicted by dividing the number of variant RNA transcripts produced per tumor and normal cell at a given locus by the total number of RNA transcripts produced from that locus:

$$VAF_{RNA_{(i,l)}} = \frac{\text{Variant } RNA \text{ copies}_{(i,l)}}{\text{Total } RNA \text{ Copies}_{(l)}} \quad (5)$$

For a SNP with copy number, $C_S$ (see equation 13), in a tumor of a purity, p, local tumor total copy number $C_T$, and with normal copy number, $C_N$, and normal minor copy number $C_{Nm}$, the RNA fraction can be approximated if the level of transcriptional amplification (amp) at locus l is known:

$$VAF_{RNA_{(i,l)}} \approx \frac{C_{S_{(i,l)}} * amp_{(l)} + \left(\frac{1-p}{p}\right) * C_{Nm}}{C_{T_{(i,l)}} * amp_{(l)} + \left(\frac{1-p}{p}\right) * C_N} \quad (6)$$

where $C_{S(i,l)}$*$amp_{(l)}$ represents the number of alternate allele RNA copies produced from the tumor, $C_{T(i,l)}$*$amp_{(l)}$ represents the total number of RNA copies produced from the tumor, and $$C_{Nm} * \left(\frac{1-p}{p}\right)$$

and $$C_N * \left(\frac{1-p}{p}\right)$$

represents the number of alternate allele and total copies produced per contaminating normal cell.

Substituting Equation (1) and Equation (2) for the minor and total normal copy number (as is expected on normal autosomal chromosomes) and then rearranging to solve for amp gives:

$$amp_{(i,l)} = \frac{C_{Nm} * (1-p) + C_N * VAF_{RNA_{(i,l)}} * (p-1)}{p * \left(C_{T_{(l)}} * VAF_{RNA_{(i,l)}} - C_{S_{(i,l)}}\right)} \quad (7)$$

In some cases, variants are included in the analysis performed by the system 200 if they meet certain quality criteria. For example, variant loci supported by too few reads in the DNA (<8) or the RNA (<5) can be removed. Variants can also be filtered to only include silent and missense mutations on autosomes with at least 4 alternate reads support in both the DNA and RNA, and VAF RNA and DNA greater than 0.05. These filters can be used to ensure that only high-quality variants are considered, in regions that were expressed, and variants that were not impacted by strong selection pressures (such as stop-gain or stop-loss mutations).

In the present examples, the measure of RNA amplification is generally focused on the elevated transcription of both alleles (normal and mutated); however, it is understood that the system 200 can be directed to many genes that undergo allele specific expression in the tumor for other reasons. Such variants can be identified because their $VAF_{RNA}$ increase that causes the denominator of Equation (4) to become negative (~26% of variants). In some cases, these can be removed to ensure that the measure of transcriptional output was not impacted by allele specific expression.

In some cases, to further prevent outlier variants, whose individual expression is not reflective of genome-wide transcriptional output, from influencing the output, the system 200 can use an average amplification value calculated for the central 98% of variants (post filtering for both subs and LOH-SNPs). This effectively removes any remaining outliers whose amplification levels are more reflective of allele specific, or cancer specific expression, rather than true transcriptional amplification. The resulting distributions represent the fold change in RNA output between the cancer and normal cells within a single tumor sample. The mean value of this distribution can be used as a final estimate of transcriptional output for this specific patient sample.

The theoretical tumor RNA content per sample, being the proportion of all RNA in a tumor sample which is cancer cell derived, can be given by:

$$\text{Tumor } RNA \text{ Content} = \frac{p * RNAt * \text{ploidy}/2}{p * RNAt * \text{ploidy}/2 + (1-p) * RNAn} \quad (8)$$

where p is purity, RNAt is RNA output per tumor cell, and RNAn is RNA output per normal cell.

Given that:

$$\text{amp} = \frac{RNAt}{RNAn} \quad (9)$$

RNAt/amp can be substituted for RNAn in the denominator and simplified to give:

$$\text{Tumor } RNA \text{ Content} = \frac{\text{purity} * \text{amp} * \text{ploidy}/2}{(\text{purity} * \text{amp} * \text{ploidy}/2) + (1 - \text{purity})} \quad (10)$$

Thus, given the relative fold amplification of tumor cells versus normal cells, and tumor purity, the proportion of tumor derived RNA in the intermixed sample can be estimated.

In example experiments conducted by the present inventors, as described below, cell lines HCC1954, HCC1143, HCC2218, HCC1954BL, HCC1143BL, HCC2218BL were obtained and cultured in Roswell Park Memorial Institute (RPMI) with 10% fetal bovine serum (FBS). UW228 cells were obtained and cultured in α-MEM with 10% FBS. UW228 cells made to stably express cMyc by infection with pMN-GFP-c-Myc. Cells were harvested and counted using Vi-Cell XR Cell Viability Analyzer prior to DNA and RNA extraction using Allprep DNA/RNA Mini Kit and RNA quantification using Nanodrop 1000 to generate per cell estimates of RNA output, and fold amplification values. RNA from tumor and normal cell lines were then mixed in RNA cellular equivalents create dilutions of 0, 20, 40, 60, 80, and 100 percent purity. Evaluation of the External RNA Controls Consortium (ERCC) RNA-spike-ins were added to the pure cell line RNA samples normalized to cell number prior to sequencing. UW228 does not have a matched normal, therefore HCC1954BL peripheral blood cell line was used. These mixtures underwent library preparation using NEBnext and RNA-sequenced to at least 100× depth using the Illumina HiSeq 2500. DNA was extracted from the pure cell lines and underwent whole exome sequencing (WES) using an exome enrichment kit. DNA from UW228 and HCC2218 cells was also used for Affymetrix CytoscanHD SNP array analysis. Affymetrix SNP6 array data was downloaded for HCC1954 and HCC1143 cell lines. Mutation calling was performed using MuTect2 and DNA copy number was derived using the Tumor Aberration Prediction Suite (TAPs). For the UW228 cell line, LOH-SNPs were identified by finding the union between heterozygous SNPs in the HCC1954BL normal cell line and matching alleles in LOH regions of the UW228 cell line. DNA VAFs in the impure samples were corrected based on purity and mutation copy number using the following equations for germline and somatic variants respectively:

$$\text{Purity corrected } VAF \text{ } DNA \text{ (Germline } SNPs) = \frac{(1-p) + (p * C_S)}{2 * (1-p) + (p * C_T)} \quad (11)$$

$$\text{Purity corrected } VAF \text{ } DNA \text{ (Somatic } Subs) = \quad (12)$$

$$\frac{p * C_M}{p * C_T + C_N * (1 - \text{purity})}$$

The samples were then processed using the system 200.

Germline SNPs were identified from matched normal exome sequence data using GenomeAnalysis Toolkit (GATK) best practices. Each sample was first processed using HaplotypeCaller in single-sample genotype discovery mode. Joint genotyping was subsequently performed across the entire cohort. Variants were filtered using GATK's Variant Quality Score Recalibration using known polymorphic sites from HapMap and Illumina's Omni 2.5M SNP chip array for 1000 Genomes samples as true sites and training resources, 1000 Genomes high confidence SNPs as non-true training resource, and dbSNP for known sites but not training. The truth sensitivity filter level was set to 99.5%. Germline SNPs were filtered to select only biallelic heterozygous SNPs with a genotype quality score above 30.

Raw SNP6 CEL files were pre-processed using the PennCNV-Affy pipeline to generate LogR and BAF values for each sample. Affymetrix Power Tools software was used to generate genotype clusters (apt-genotype) and to perform quantile normalization and median polish to produce signal intensities for A and B alleles of SNPs (apt-summarize). PennCNV was then used to convert the signal intensities into LogR and BAF values (normalize_affy_geno_cluster.pl). LogR and BAF files were then processed in R using the ASCAT R package to generate allele-specific copy number calls, and purity and ploidy estimates for each sample. In this example, the copy number status of MYC was defined using ASCAT and defined parameters; where a total copy number greater than or equal to 5 in a sample with ploidy less than 2.7, or total copy number greater than or equal to 9 in a sample with ploidy greater than 2.7 are defined as copy gain events.

Somatic and germline single base variants were merged into a single VCF file for each sample and annotated using vcf2maf and the Ensembl Variant Effect Predictor to produce annotated MAF files for each sample. Allele-counting was performed on variant sites for each sample using GATK's ASEReadCounter on matched exome and RNA-sequencing data. Minimum read mapping quality and minimum base quality was set to 10 and 2 respectively. Depth downsampling was turned off. In this example experiment, SNPs called as heterozygous in the germline, but where over 97.5% of DNA reads supported a single allele in the tumor were removed due to the likelihood that these were misidentified homozygous loci. Likewise, germline variants in imprinted loci, where over 97.5% of RNA reads supported a single allele, were identified and removed.

The copy numbers of each SNP, $C_S$, were determined from tumor exome read count data using:

$$C_S = \frac{VAF_{DNA} * ((p * C_T) + (2 * (1 - p))) - (1 - p)}{p} \qquad (13)$$

These values were used to determine whether the reference or alternate allele at a given loci was lost in regions of loss-of-heterozygosity (LOH).

The VAF distributions for LOH-SNPs located on the reference and alternate alleles are generally mirror images of each other. To harmonize all LOH-SNPs, the reference and alternate allele counts for SNPs in regions where the alternate allele was lost were inverted prior to any filtering. Samples with fewer than 15 high quality variants passing filters were removed.

Figure 30:
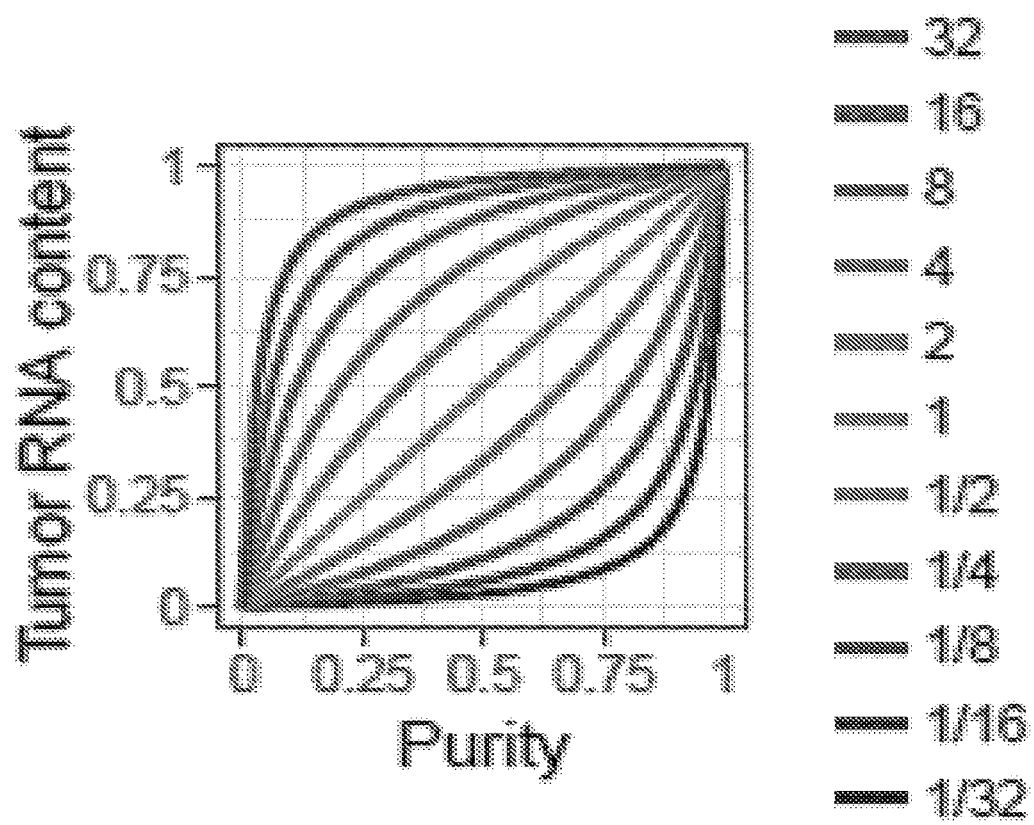
FIG. 30 shows in-silico tumor RNA content calculations for different amplification levels and purity levels.

Based on in-silico analysis, at low tumor purities, high levels of transcriptional amplification lead to more appreciable changes in the measured RNA content, as shown in FIG. 30. As purity increases, however, the sample can become "saturated" by tumor-derived RNA, such that further increase in transcriptional output can lead to diminishingly small gains in tumor transcripts relative to the normal. Put simply, if 95% of the total RNA is already derived from the tumor cells (due to high purity), any additional increase in RNA (due to amplification) may be difficult to quantify accurately. In such situations, the tumor is correctly marked as 'amplified', but its value may be a conservative underestimate of the tumor's true transcriptional output. To maintain accuracy and sensitivity in subsequent experiments, using the whole TCGA cohort, samples with very high purity (>75%) were removed and statistically corrected for differences in purity where necessary. After applying all filters, 6,095 TCGA samples remained for downstream analysis.

Figure 33:
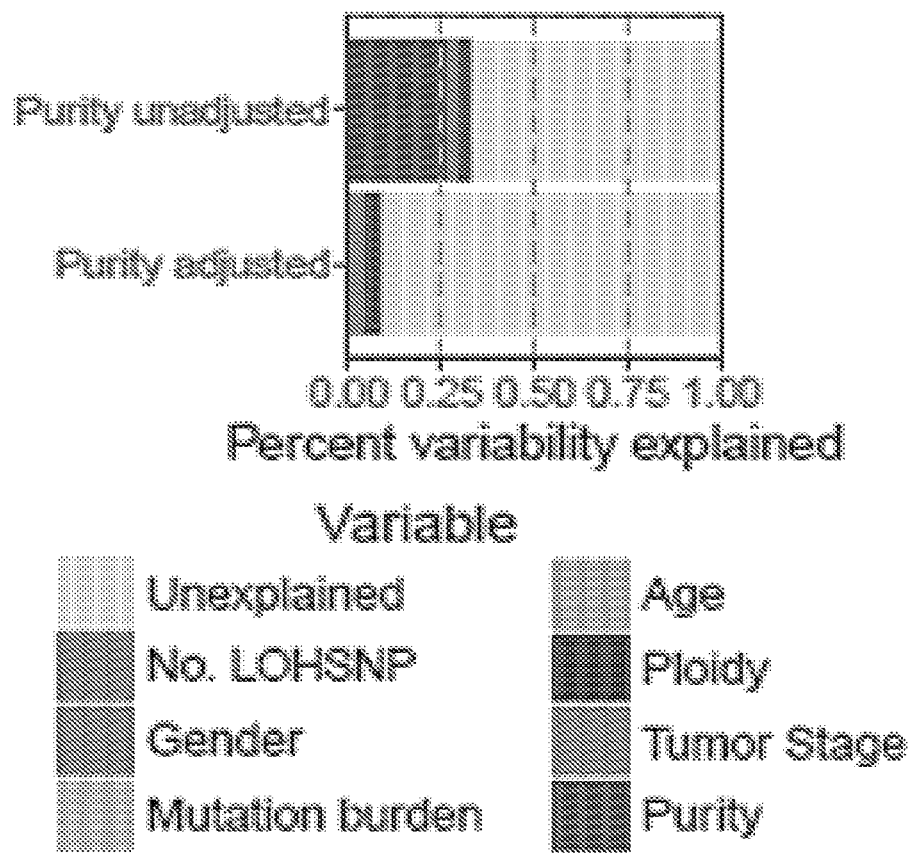
FIG. 33 shows a diagram of variability explained in RNA amplification levels before and after adjusting for tumor purity.

To determine the variance explained in transcriptional output levels by predictor variables, the relaimpo R package and the 'lmg' method was used. The proportion of additional variability explained by tissue germ layers, tumor types, and tumor subtypes was accessed by adding each in turn, and comparing the differences in variability explained between each model. Purity was included as a covariate in this analysis, prior to removing it and readjusting the remaining variables, as shown in FIG. 33.

Duplicate reads were removed from RNA-sequencing data using picard MarkDuplicates prior to gene and exon level expression counting. Gene expression counts were generated using HTseq. Exon expression counts were created using the dexseq_count.py script. Gencode V25 gene annotations were used for both genes and exons. Counts were normalized using the counts per million method for correlation analysis. Gene lists for the 50 hallmark expression pathways were obtained from the Molecular Signatures Database. To measure expression of the 50 hallmark expression pathways, Gene Set Variation Analysis (GSVA) was used on Reads Per Kilobase of transcript, per Million mapped reads (RPKM) normalized gene expression counts.

The system 200 trained a ridge regression model using a leave-one-out cross validation approach. The model included transcriptional output levels as the outcome variable, and hallmark pathway expression data (50 pathways), purity, ploidy, tumor type, mutation burden, LOH-SNP count, tumor stage, gender, and age at diagnosis as predictors. This approach was repeated within tumor types in which at least 80 samples contained information for all included predictors and the resulting normalized coefficients were plotted as a heatmap. To assess the variability explained by hallmark pathway expression, Analysis of Variance (ANOVA) was performed with all 50 pathways included alongside all covariates used in the variability explained model, and assessed, in aggregate, how much additional variability in each model was explained by inclusion of all hallmark pathway expression levels. This analysis was performed both across the pan-cancer cohort and within individual tumor types.

A list of relevant metabolic genes involved in either the Warburg effect or rate limiting for nucleotide synthesis in cancer were manually curated. Kyoto Encyclopedia of Genes and Genomes (KEGG) metabolic pathways were curated from the Molecular Signatures Database and processed by GSVA to produce pathway level expression values. Pearson's correlations between each of these genes' or pathways expression values and amplification was determined. P-values were adjusted using a false discovery rate (FDR) approach.

mRNA expression based stemness index values were obtained and stemness genesets were curated. Pathway activity levels were determined using GSVA on RPKM normalized gene expression counts. Correlations to amplification levels were determined using Pearson correlation, and adjusted p-values were produced using the FDR approach.

Clinical data for the TCGA cohort was obtained. To accommodate the variable follow-up times in each tumor cohort, the example experiments focused on 5-year overall survival, and tumor types with at least 3 or more events (which excluded KICH, PCPG and THCA tumor types), or subtypes with at least 1 or more events (which excluded BRCA Normal, TGCT Seminoma, SARC Other, UCEC CN Low and UCEC Pole subtypes). Pancreatic adenocarcinomas were excluded from tumor type specific analysis due to known inconsistencies with that particular cohort's survival data compared to established pancreatic cancer cohorts. To determine prognostically relevant thresholds of transcriptional output levels, the R package OptimalCutpoints was used. A transcriptional output level which best discriminated prognostic outcomes by maximizing Youden's index was defined. Youden's index was used due to its ability to maximize the sum of specificity and sensitivity. Each tumor type or subtype was assigned an independently defined transcriptional cut-off. Tumor types or subtypes where over 95% of samples were assigned to either the high or low group were removed. The remaining tumor types and subtypes were used for Kaplan-Meier survival analysis and Cox regression. Tumor type, tumor stage, age at diagnosis, tumor mutation burden, purity, ploidy, race, gender and ethnicity were included in Cox regression models when available.

Fully processed Illumina Infinium HumanMethylation450K array data for the TCGA cohort was obtained. Each sample's mean methylation was calculated across all probes. The most variable probes were used for hierarchical clustering of the IDHmutant-codel cohort.

In the example experiments, only missense, nonsense, and nonstop mutations were considered for the expressed tumor mutation burden analysis. To be considered expressed, a mutation required at least 3 alternate read support in the RNA. To determine a threshold for transcriptional hypermutation from the TCGA cohort we considered the proportion of samples which harbored genomic hypermutation (~10.3% of samples). A quantile function was applied to determine the threshold of transcriptional mutation burden for the top 10.3% of samples, which was 3.03 expressed mutations per megabase. This value was also very close to the average proportion of expressed mutations per megabase for hypermutant samples (31.5%—meaning that on average ~3.15 out of every 10 mutations were expressed in the RNA of hypermutant samples). These estimates were rounded to a value of 3 expressed mutations per megabase as the cut-off for transcriptional hypermutation.

To determine an adjusted gTMB value based on the expressed TMB, a linear regression model was built with eTMB as the predictor variable and gTMB as the outcome variable. This model captured the average relationship between a tumors genomic and transcriptomic mutation burden across the entire TCGA cohort. This model was used to predict, on a sample-by-sample basis, what gTMB value would be expected based only upon a tumor's eTMB value. This new value was referred to as an adjusted gTMB, which reflects the genomic mutation burden one would expect given only a tumor's expressed mutation burden.

Raw whole-exome and RNA sequencing data was retrieved for ICI treated melanoma patients. Whole exome sequencing (WES) sequence data was aligned and RNA-sequencing data was aligned using STAR in 2-pass mode. Somatic mutation data was obtained and GATK's ASEReadCounter was used to count reference and alternate reads for each somatic mutation. Samples were then processed by the system 200, without requiring copy number data. Instead, a combination of three related metrics were used comparing the RNA and DNA allele fractions, the VAF difference, VAF ratio, and allelic ratio as:

$$VAF_{DIFF} = VAF_{RNA} - VAF_{DNA} \qquad (14)$$

$$VAF_{RATIO} = \frac{VAF_{RNA}}{VAF_{DNA}} \qquad (15)$$

$$\text{if } (VAF_{RNA} < VAF_{DNA})\left\{\text{Allelic Ratio} = \frac{VAF_{DIFF}}{VAF_{DNA}}\right\} \qquad (16)$$

$$\text{else } \left\{\text{Allelic Ratio} = \frac{VAF_{DIFF}}{1 - VAF_{DNA}}\right\}$$

Each sample was ranked according to each of these metrics, taking the mean ranking to assess global amplification levels. Samples were then grouped into high and low amplification groups based on a median split. Genomic hypermutation was defined as >10 mutations per megabase. Expressed mutations were determined, and transcriptional hypermutation was defined as >3 expressed mutations per megabase.

Figure 3:
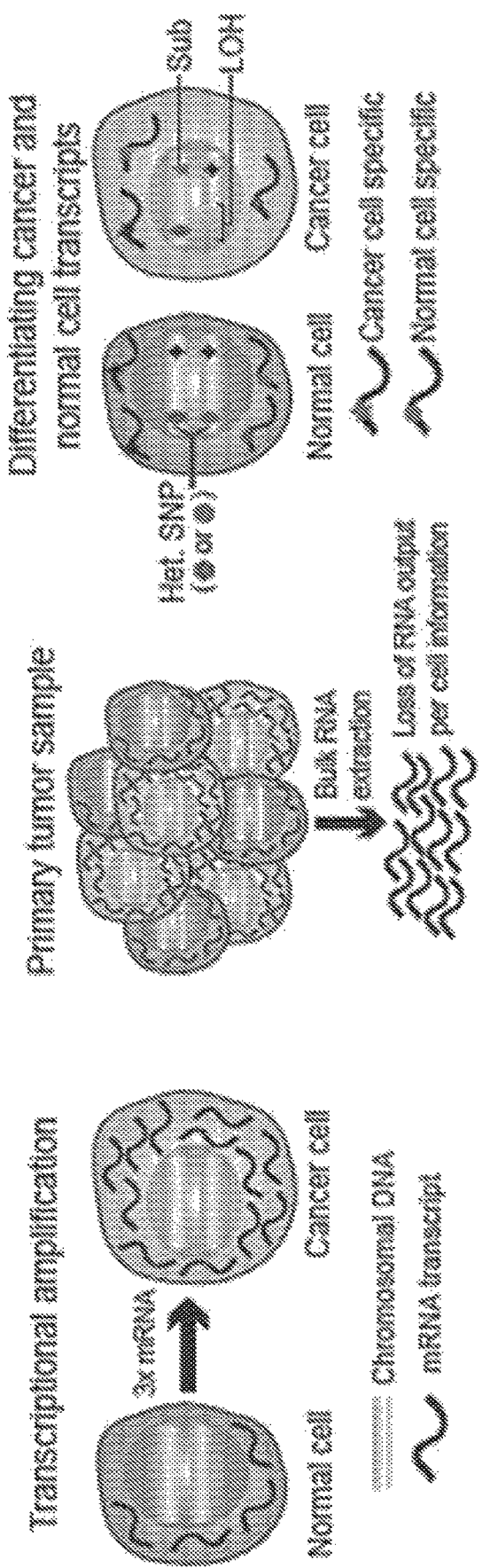
FIG. 3 shows a diagram of how transcriptional amplification occurs when cancer cells elevate their transcriptional output above normal cell level.

Using the above approach of the system 200, the present inventors determined the results of the example experiments. To distinguish sequencing reads derived from tumor cells from the intermixed normal cells, the system 200 uses expressed mutations and loss-of-heterozygosity (LOH) events, as shown in FIG. 3. A typical adult cancer contains ~8,000 somatic substitution mutations, of which over 200 are located within a transcription unit (excluding introns). Similarly, LOH is a feature of neoplastic cells. Heterozygous single-nucleotide polymorphisms (SNPs) in LOH will be mono-allelically expressed in the tumor, whereas the intermixed non-neoplastic cells with retained heterozygosity express both alleles. Considered together, expressed somatic substitutions and LOH-SNPs form hundreds to thousands of individual 'markers' from which a tumor's cancer-cell-specific expression can be detected by the system 200.

Figure 4:
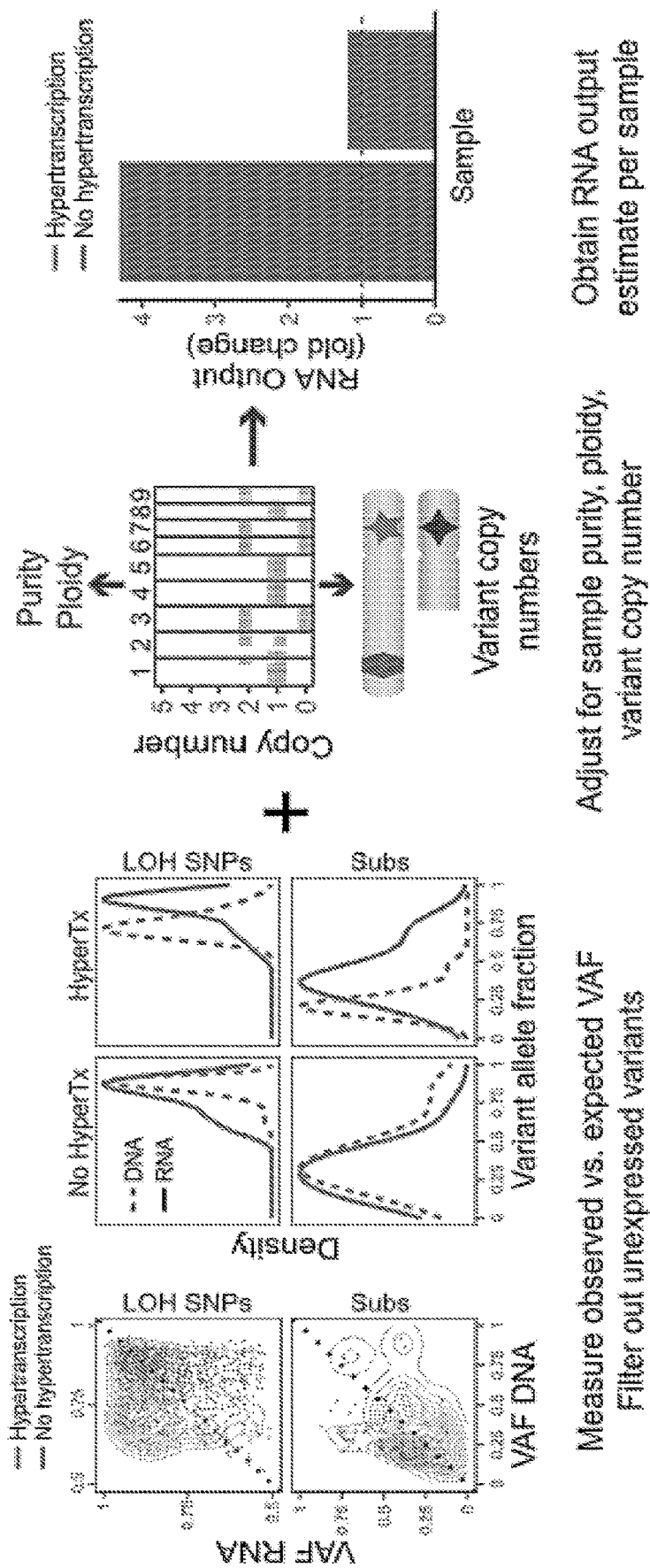
FIG. 4 shows a diagram of an overview of measuring transcriptional output in primary tumors.

The system 200 compares the variant allele fraction (VAF) of markers in the RNA relative to deoxyribonucleic acid (DNA) to quantify cancer-cell specific changes in transcriptional output, as shown in FIG. 4. When there is no elevation in the cancer's global transcription, the fraction of reads supporting cancer variants in the RNA would be consistent with that of the DNA (i.e., similar VAFs). In cases of elevated RNA production, an increase in the fraction of RNA reads supporting cancer variants relative to the DNA is expected. In some cases, to accurately quantify levels, loci in imprinted regions, as well as unexpressed variants, can be removed; and then corrected for tumor purity, and regional DNA copy number.

Figures 5A, 5B, 5C:
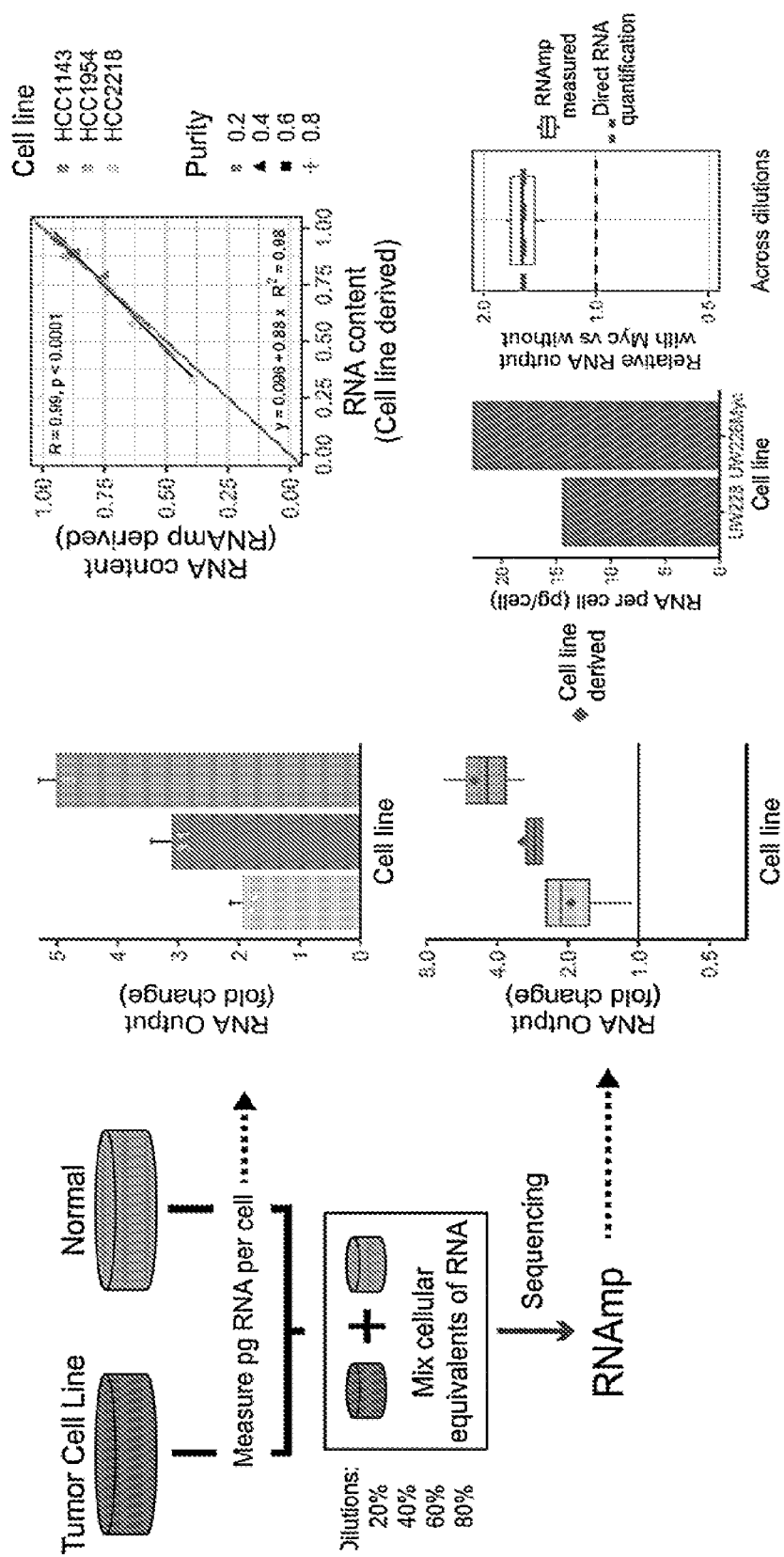
FIG. 5A shows a diagram of a validation example experiment involving mixtures of cellular equivalents of RNA from tumor and normal cells.
FIG. 5B shows a chart of fold amplification levels of cell lines based on cell counting and direct RNA quantification.
FIG. 5C illustrates a chart of RNA amplification derived tumor RNA content compared to actual RNA content demonstrating very high concordance.
Figure 22:
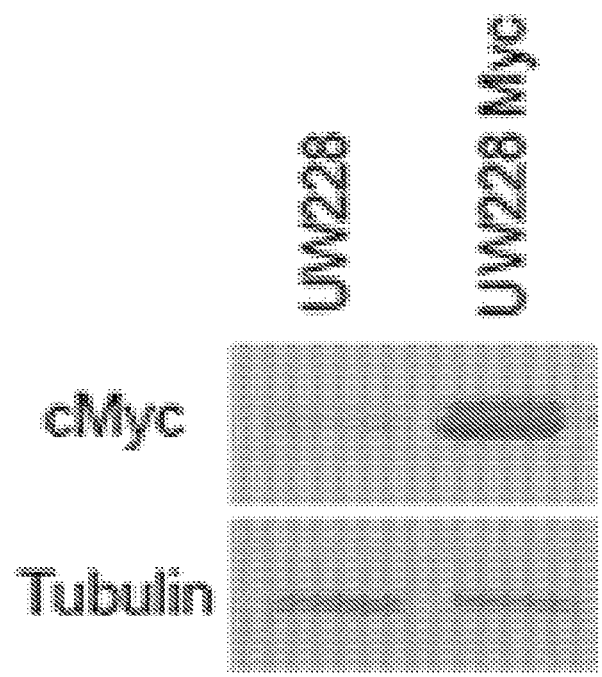
FIG. 22 shows a western blot of Myc induction in medulloblastoma cells (UW228)
Figure 23:
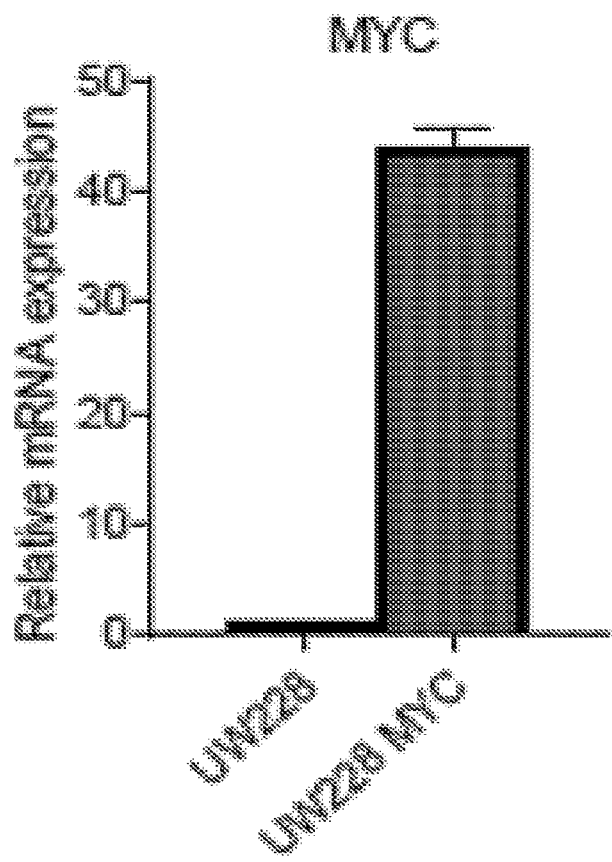
FIG. 23 shows a chart of qRT-PCR Myc mRNA expression.
Figure 24:
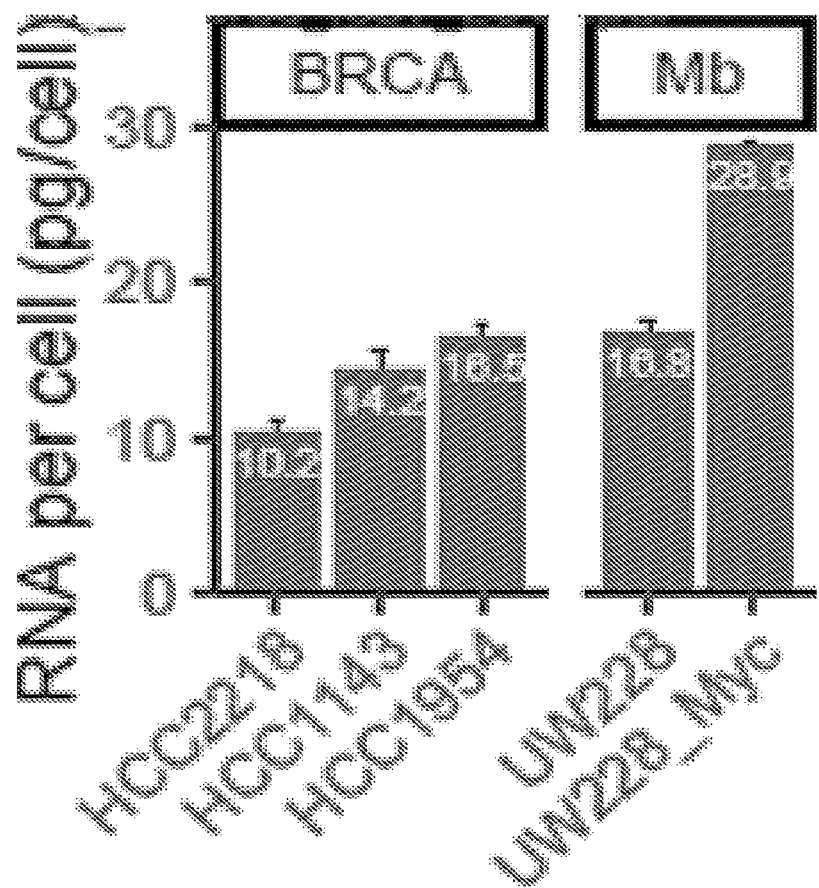
FIG. 24 shows a chart of RNA output per cell for each line tested.
Figure 26:
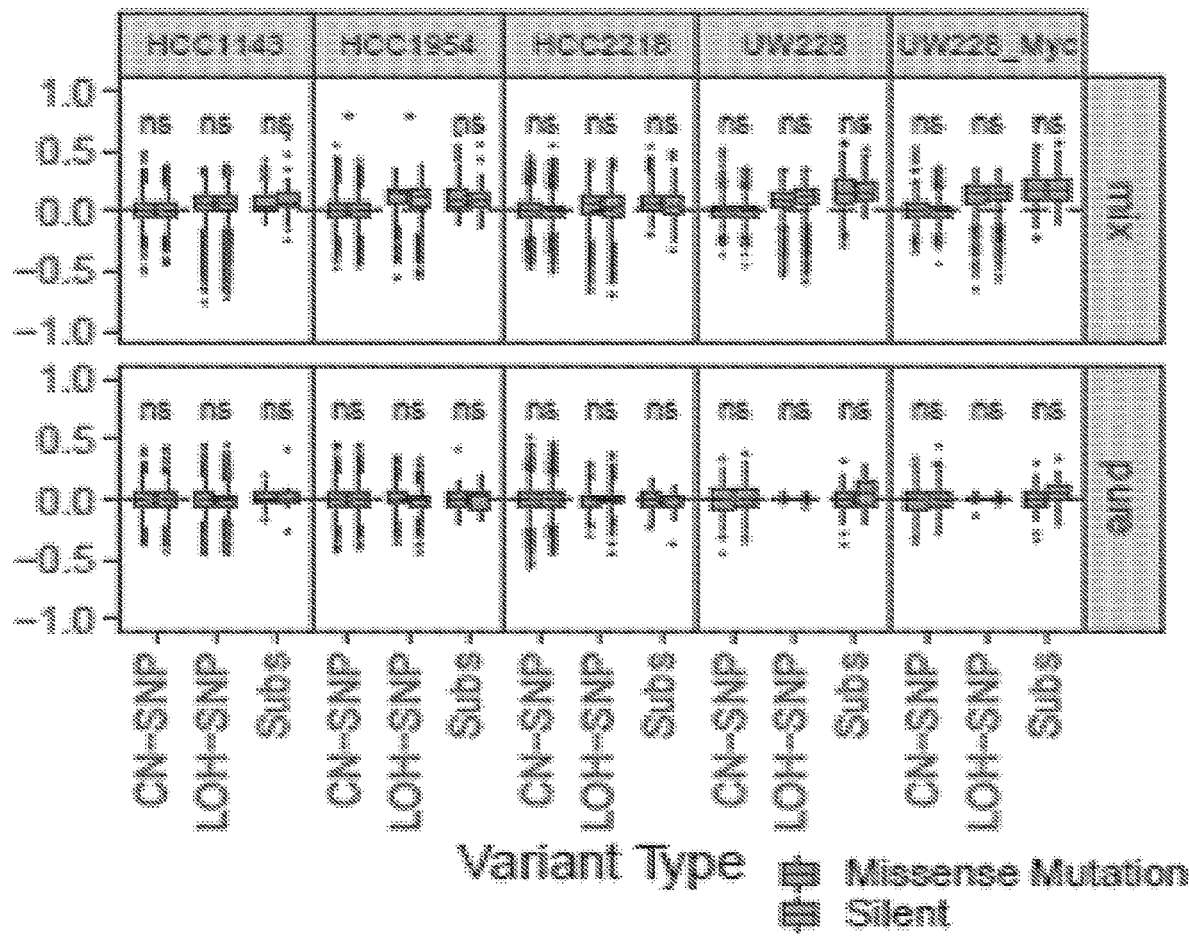
FIG. 26 shows variant allele fraction difference boxplots of copy-neutral SNP (CN-SNP), LOH-SNP, and somatic substitution variants of each cell line used in either cell mixtures, or purified cell lines split by missense and silent variant types.
Figure 27:
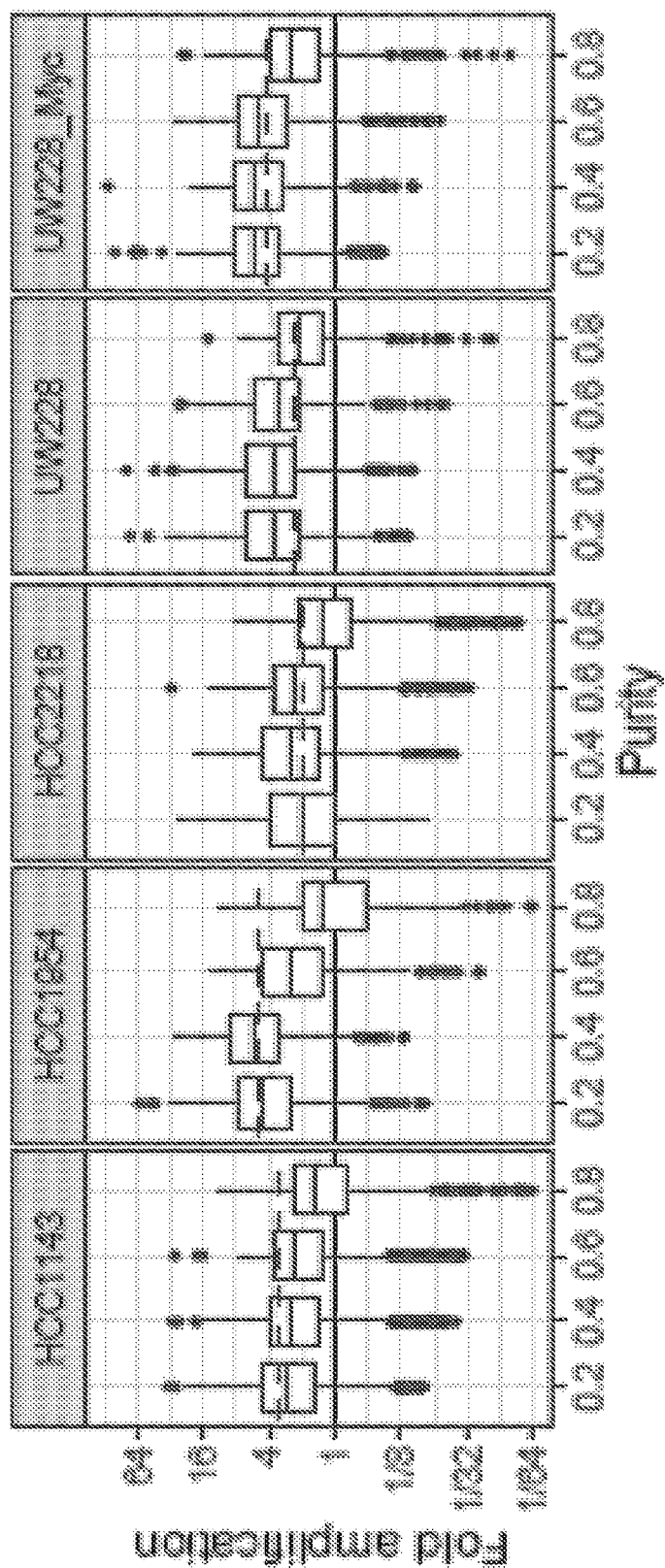
FIG. 27 shows a chart of RNA fold amplification distributions for each cell mixture.
Figure 28:
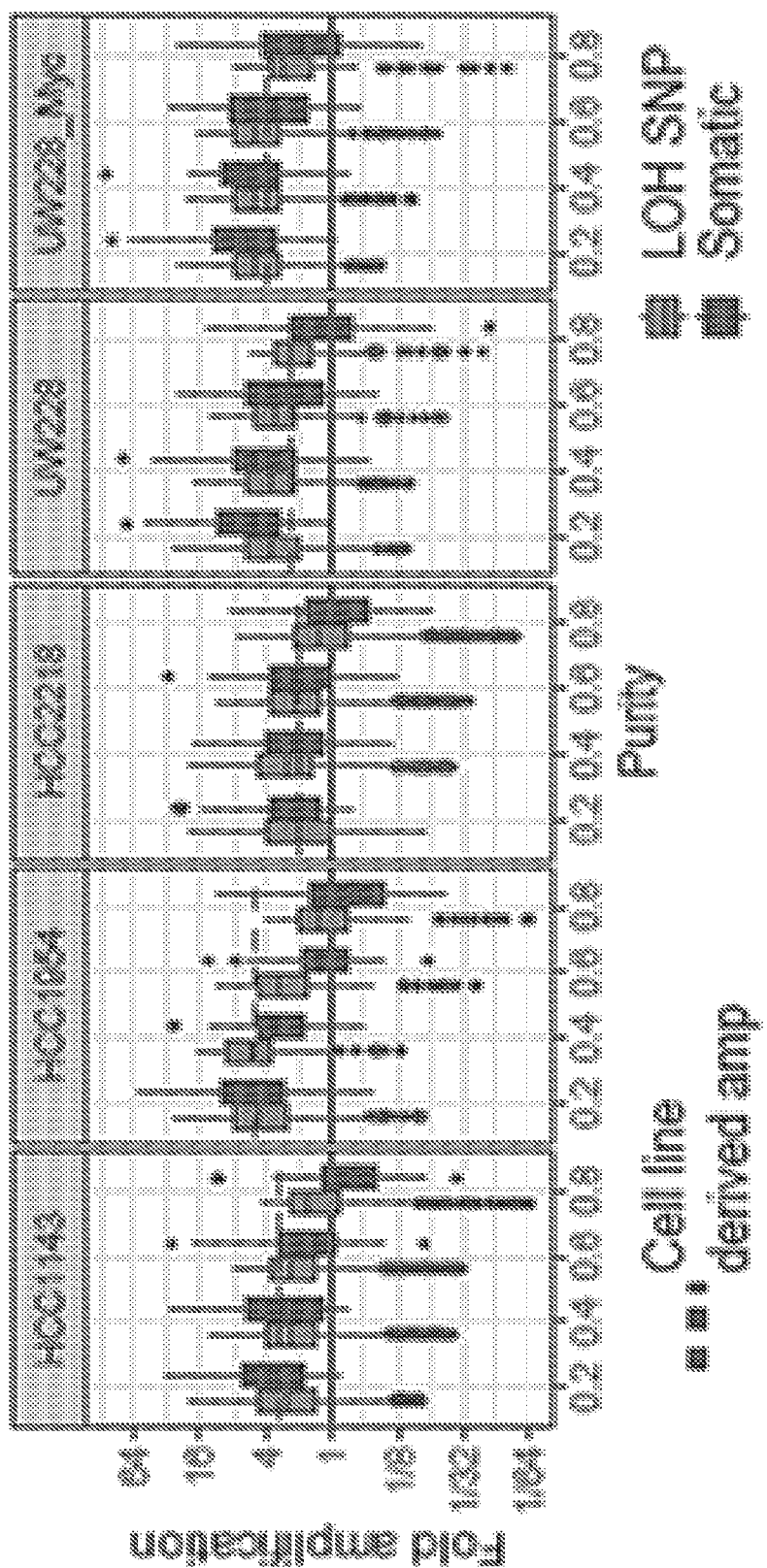
FIG. 28 shows a chart of RNA fold amplification distributions for each cell mixture split by LOH SNP and somatic substitution variant types.
Figure 29:
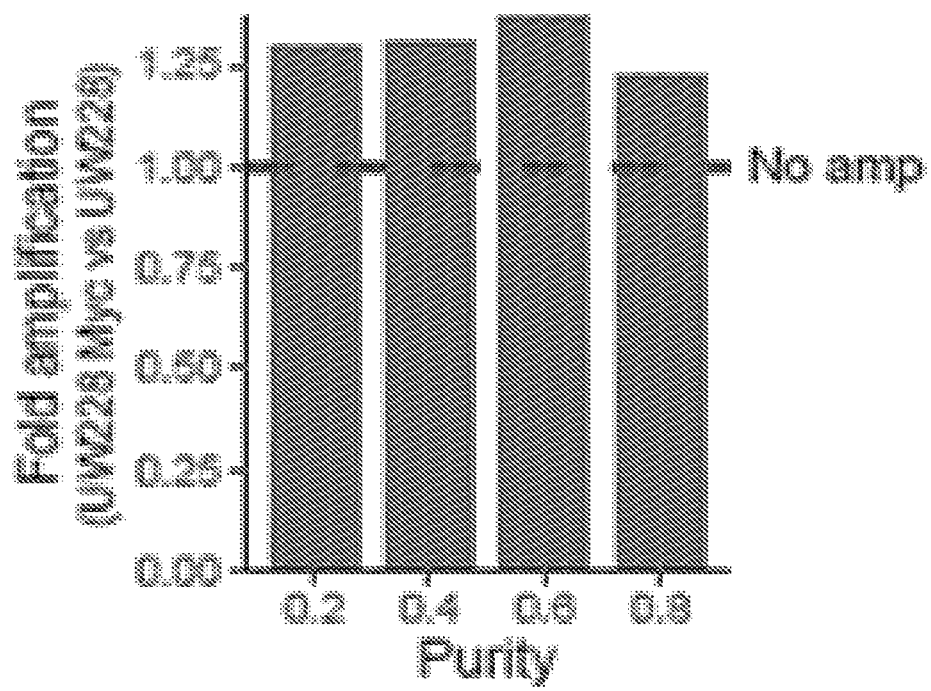
FIG. 29 is a barplot depicting transcriptional amplification in Myc containing UW228 cells versus wild type UW228 cells.

To evaluate the accuracy of the system 200, analyses were performed on mixed cancer and normal cells after measuring each lines' total RNA output (in pg/cell), as shown in FIG. 5A. In the medulloblastoma cell line UW228, the system 200 was able to stably over expressed MYC, as shown in FIGS. 22 and 23, which led to significant increases in RNA output, as shown in FIGS. 5B and 24. Across multiple dilution mixtures, sequencing and copy number analysis were performed (by exome sequencing, RNA-Seq and SNP arrays) and then tested the system's 200 ability to measure somatic transcriptional output. The relative difference between the RNA and DNA VAFs of marker variants were determined. The RNA from every mixed sample displayed increased amounts of tumor specific markers (LOH-SNPs and Subs.), relative to the non-tumor specific copy-neutral SNPs (p-value <0.0001 for CN-SNPs vs LOH-SNPs and Subs.), as shown in FIG. 24. This was also true for silent mutations demonstrating that selective pressure on coding mutations did not explain the observed increase in expression of cancer-cell specific mutations, as shown in FIG. 26. The system 200 was able to find amplification in every mixed sample, as shown in FIGS. 27 and 28. Importantly, it was confirmed that the amplification in the Myc expressing cells was indeed above and beyond that of wild type cells (30% average increase), as shown in FIG. 29. The presence of intermixed stromal cells (that is, some amount of impurity) is used to differentiate non-tumor-derived and tumor-derived transcription. Consistent with this, in simulated data, it was confirmed that at very high purity levels, the system 200 still correctly marks the tumor as "amplified" even if the system 200 outputs a conservative underestimate of the tumor's true transcriptional output, as shown in FIG. 30. Still, across all cell lines and at all purity levels, the system 200 found high concordance between the observed and expected tumor RNA content (r=0.94, p=1.1e−09), as shown in FIG. 5C.

Figure 6:
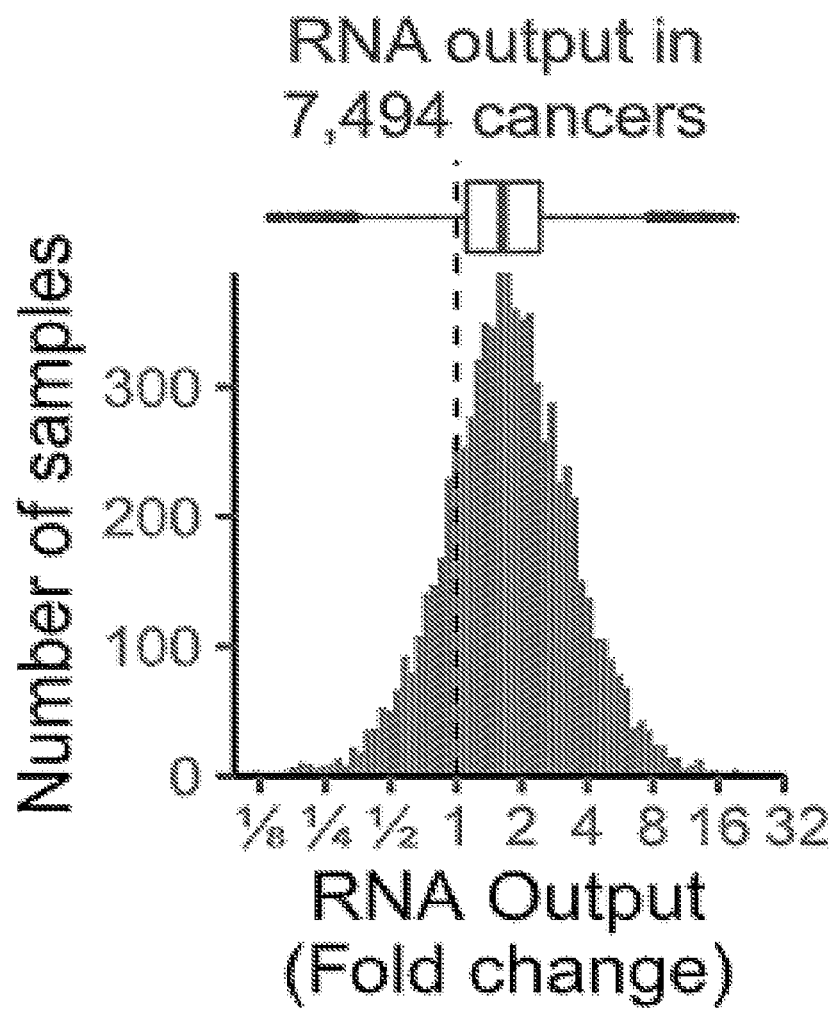
FIG. 6 is a chart of a histogram showing an example of the transcriptional output of 6,095 cancers.
Figures 31A, 31B:
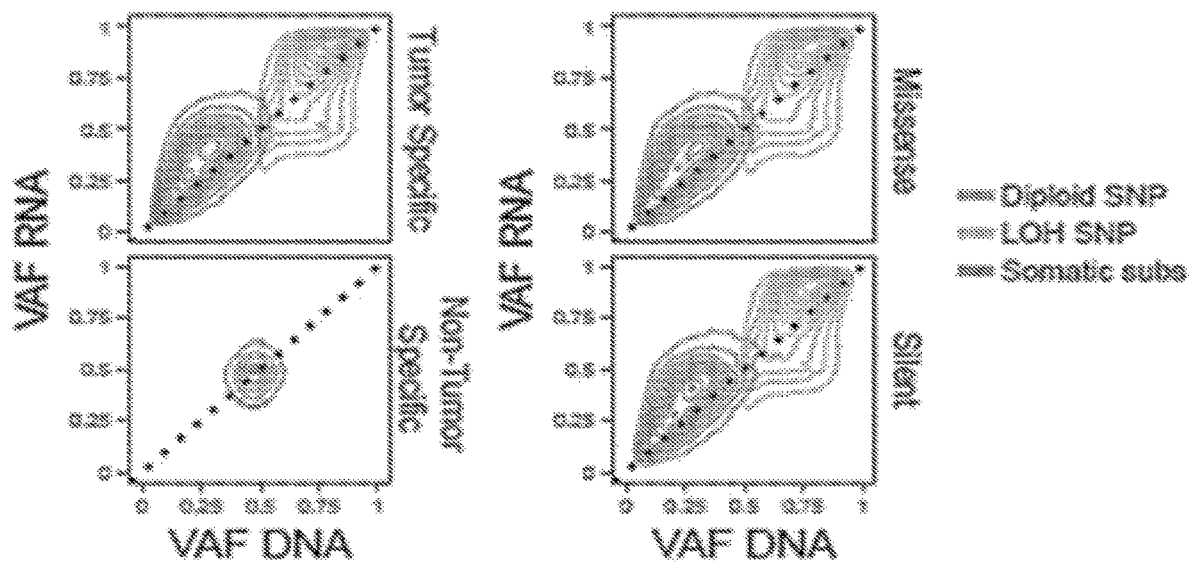
FIG. 31A shows a diagram of DNA and RNA variant allele fraction distributions for tumor specific (LOH SNPs and SNVs) and non-tumor specific variant types (diploid SNPs)
FIG. 31B shows a diagram of missense and silent mutation DNA and RNA variant allele fraction density distributions.
Figure 32:
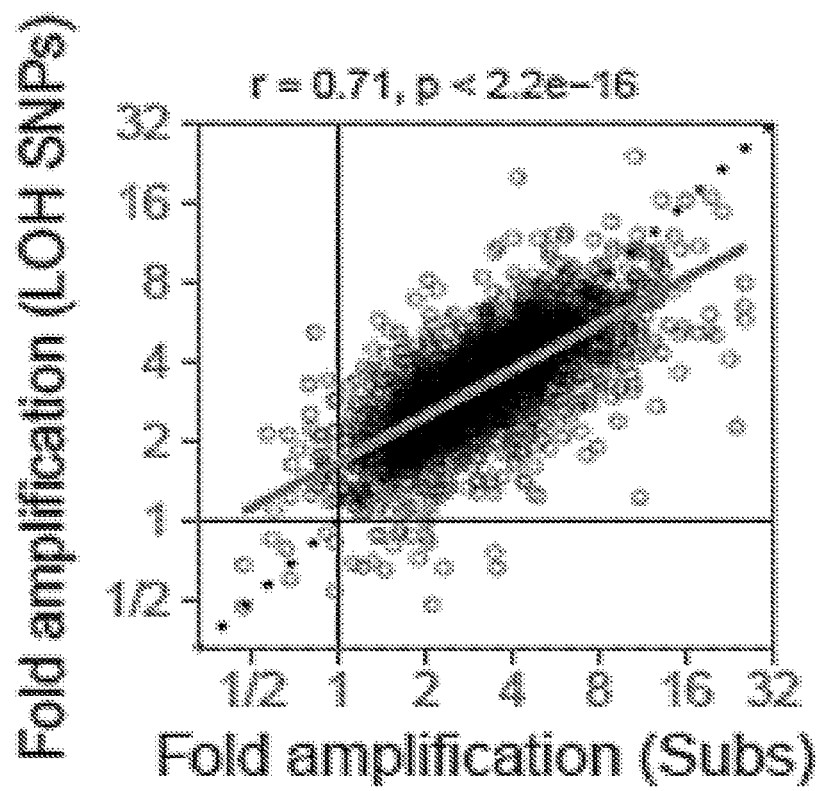
FIG. 32 shows a diagram of correlation between RNA amplification values derived independently for LOH-SNP variants and somatic substitution variants including tumors with at least 15 of each variant type.

The example experiments thus validated the sensitivity and accuracy of the system 200, and subsequently, example experiments were conducted to characterize transcriptional amplification in human cancer. 141,167 expressed somatic substitutions and 3,906,502 LOH-SNPS in 7,494 tumors were detected from 31 cancer types. Differences were measured between RNA and DNA VAFs across the whole cohort. A shift in VAF, towards RNA, was seen for both markers (substitutions and LOH SNPs), suggestive of generally increased transcriptional output in human cancers, as shown in FIG. 31A. As expected, no such change was seen with diploid SNPs. As was the case in the validation experiments, no effect was seen of selection on missense mutations, as shown in FIG. 31B. Further, amplification measures derived independently from somatic substitutions and LOH-SNPs were highly correlated (Pearson's r=0.71, p<2.2e−16), as shown in FIG. 32. Copy number and sample purity data were integrated and applied to all tumors. Across tumor types, cancer cells were more transcriptionally active than their normal counterparts, with a mean 2.22 fold-increase in RNA output, as shown in FIG. 6. Strikingly, increased transcription was nearly universal in human cancer (80% of tumor with >1-fold increase), with a 2-fold or greater increase observed in 41% of tumors. RNA output correlated significantly with higher tumor mutation burden and ploidy; particularly in genome doubled tumors (2.6 fold vs 1.9 fold; p<2.2e−16). Of note, as measures of the present embodiments were normalized per tumor DNA copy, the increased transcription observed in genome doubled tumors is 'above and beyond' what would be expected given their increased DNA copy number.

To quantify the contribution of individual factors to differences in transcriptional output, an iterative regression model was used in which features of interest were added successively, as described herein. This allowed measurements of the proportion of variability in transcriptional output explained by each feature. Tumor purity was accounted for, as shown in FIG. 33, then searched for common clinical and molecular factors, including tumor stage, ploidy, mutation burden and patient age. 10% of the global variability in amplification levels could be explained by these factors alone (of these, tumor stage and ploidy were the most important), as shown in FIG. 33.

Figures 8A, 8B, 8C:
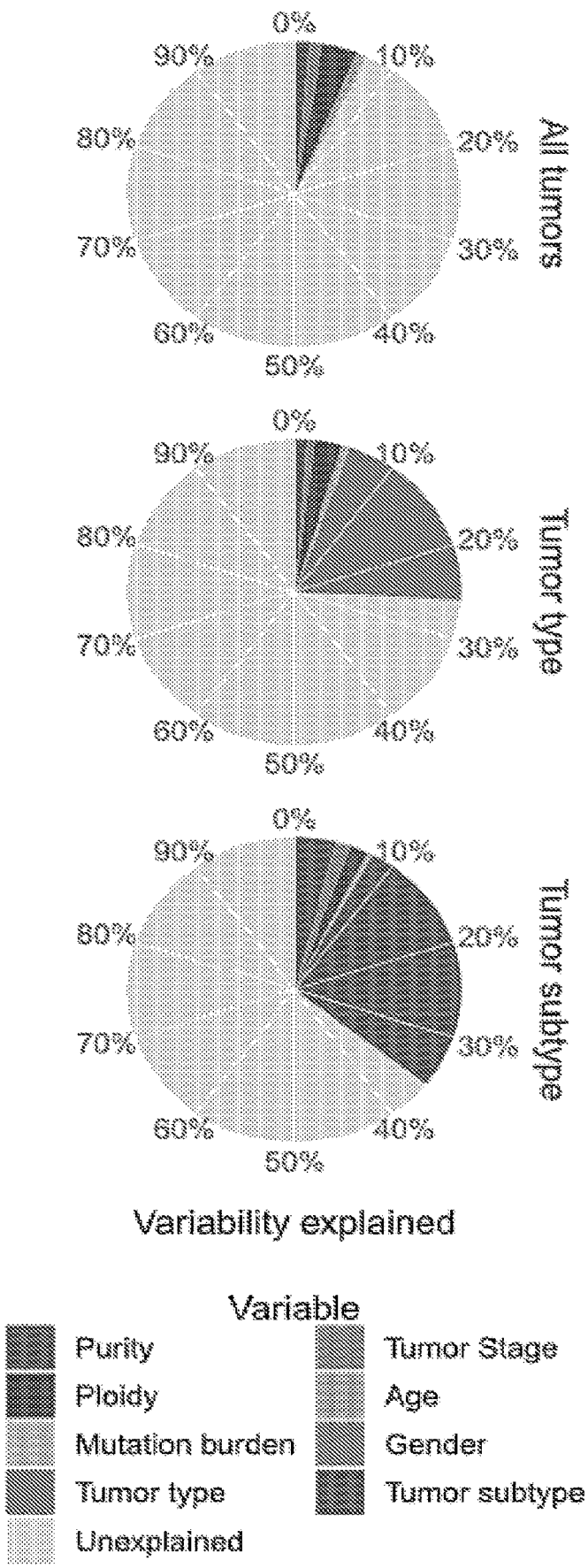
FIG. 8A shows a diagram of proportion of variability in RNA amplification for all tumors.
FIG. 8B shows a diagram of the proportion of variability explained in fold amplification levels modeled using tumor type.
FIG. 8C shows a diagram of proportion of variability explained in fold amplification levels modeled using tumor subtypes.

Since the cell-of-origin of a cancer shapes its transcriptional profile, an assessment of the relationship between the system 200 and developmental germ layer of origin was performed (neuroectoderm: five tumor types, mesoderm: 11 and endoderm/ectoderm: 14). Tumors of endodermal/ectodermal origin had the highest levels of amplification (3-fold median amplification), and the mesodermal and neuroectodermal types had lower levels (2.3 and 2.0 median fold amplification respectively; p<2.2e−16), as shown in FIG. 7A. These differences may reflect fundamental differences in gene regulation between developmental lineages; however, the developmental germ layer of origin contributes minimally to a tumor's transcriptional output (2% additional variability explained), as shown in FIG. 8A.

Figure 34:
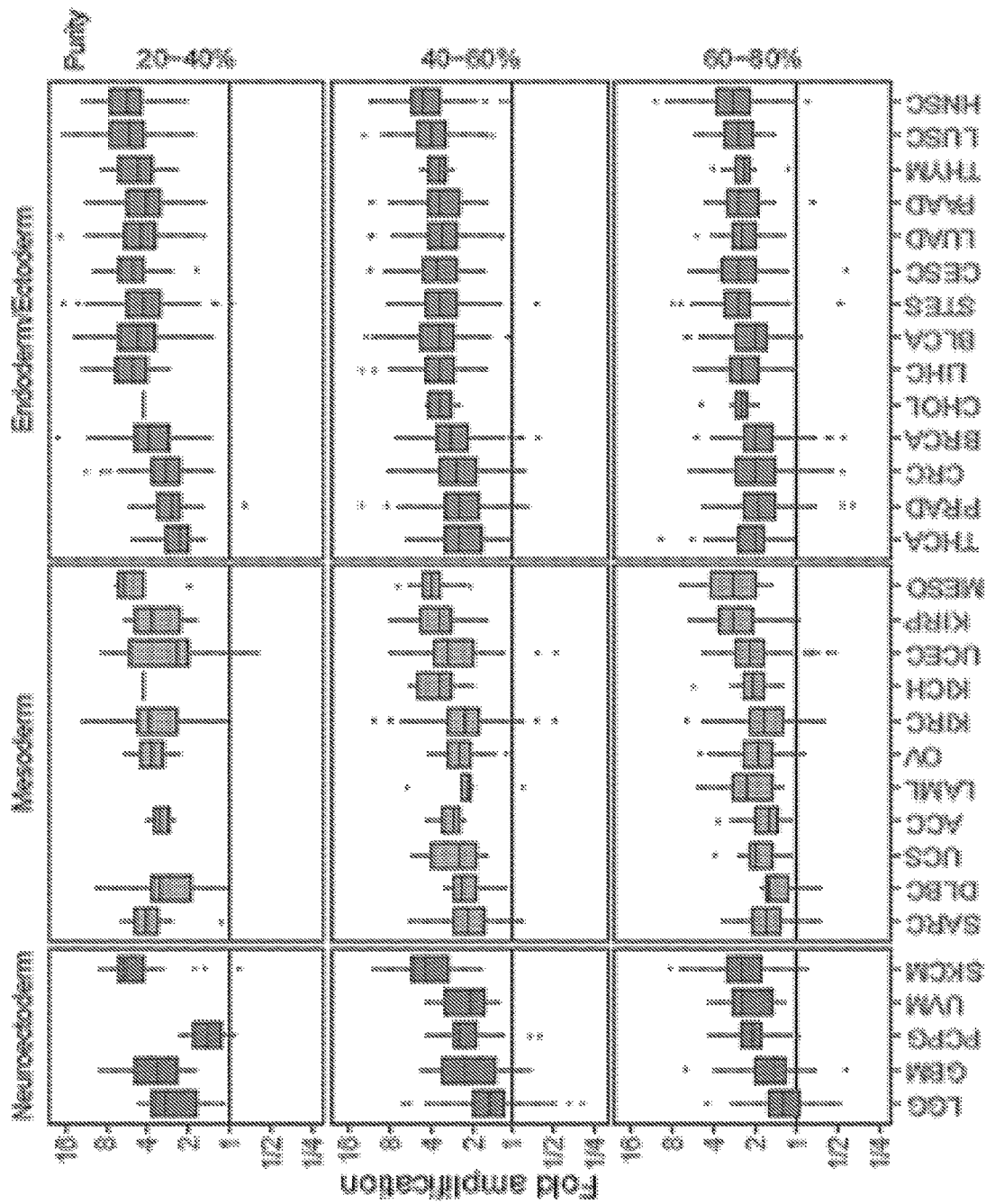
FIG. 34 shows a diagram of RNA amplification levels across different purity levels.

The RNA output of individual tumor types was further investigated. It was observed that there was a striking variability in levels of RNA amplification among 31 tumor types, as shown in FIG. 7B, even when accounting for technical and sampling differences, as shown in FIG. 34. The median amplification levels ranged from 1.4 to 4.4 across tumor types. Some tumor types, such as skin melanomas, lung cancers, and head and neck cancers, displayed consistently high levels of transcriptional amplification (>35% above 4-fold). In contrast, other tumor types, such as brain, prostate, sarcoma and ovarian, had a much lower frequency of high-level amplification (<10% above 4-fold). Overall, it was determined that individual tumor types accounted for an additional 19% of the variability of RNA output across cancer (total variance explained: 26%), as shown in FIG. 8B.

Figure 35:
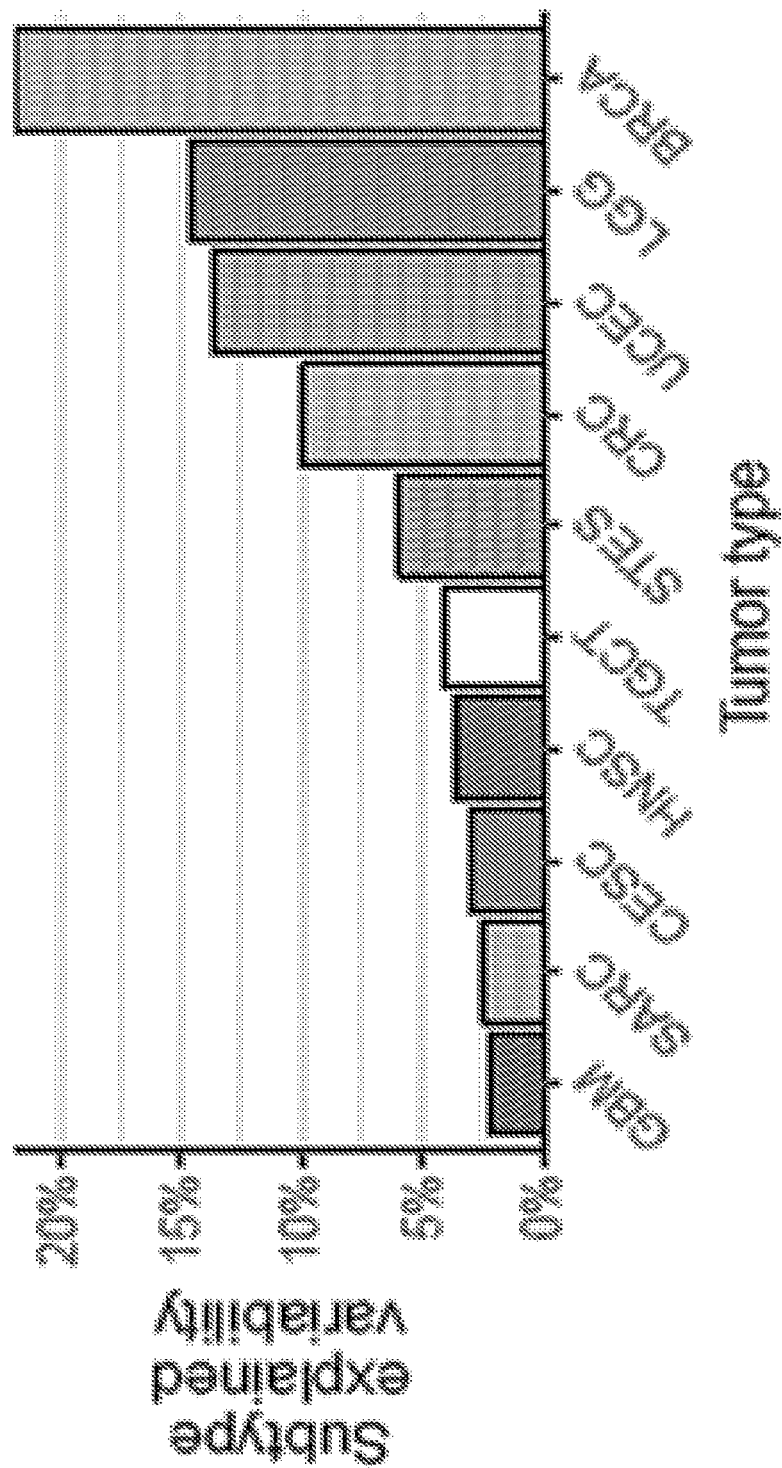
FIG. 35 shows a diagram of a proportion of variability in RNA amplification explained by subtype within selected cancer types.

In some cancers, five orders of magnitude separated the least transcriptionally active samples from the highest. To see whether this intra-tumor type variability was underpinned by molecular subtypes, the cohort was subdivided based on established clinical entities and examined amplification levels, as shown in FIG. 7C. This resolved a significant amount of intratumoral variability for many cancers. For example, in breast cancers, the more clinically aggressive basal-like subtype had the highest levels of amplification, followed by Her2, normal, and then the less aggressive luminal subtypes. Within the low-grade gliomas, the clinically aggressive IDH-wild type samples had the highest level of amplification (~1.6 times more than IDH mutated tumors). The same was true in glioblastomas. In addition to demarcating aggressive subtypes, the system 200 also co-associated with distinct subtypes. For instance, in both endometrial and colorectal carcinomas, the subtype driven by excessive point mutations (MSI, POLE) had increased RNA output compared to the copy number-associated subtype (CIN, CN High). In certain tumors, molecular subtype explained a significant fraction of the variability in RNA output (>10%), as shown in FIG. 35. Taken together, tumor subtypes explained an additional 13% of the variability in transcriptional output, bringing the total to ~40%, as shown in FIG. 8C.

Figure 9:
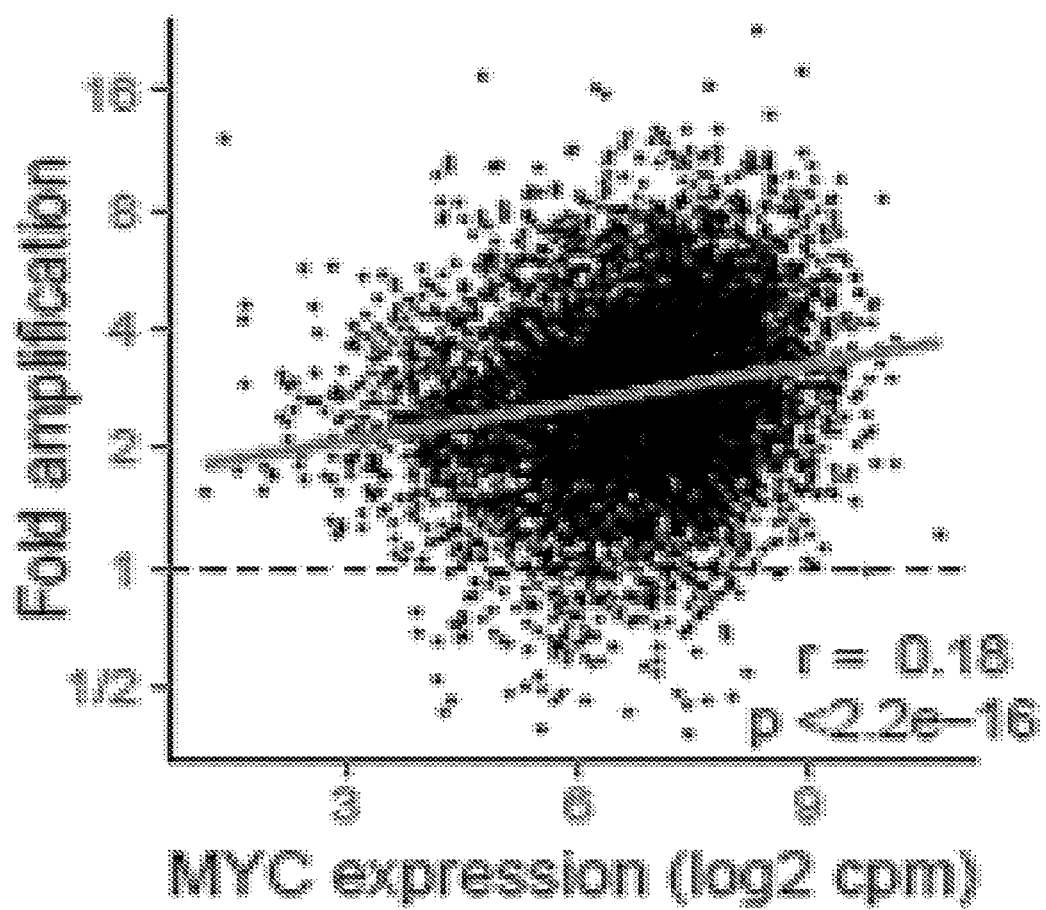
FIG. 9 shows a chart of correlation between MYC expression and RNA amplification.
Figure 10:
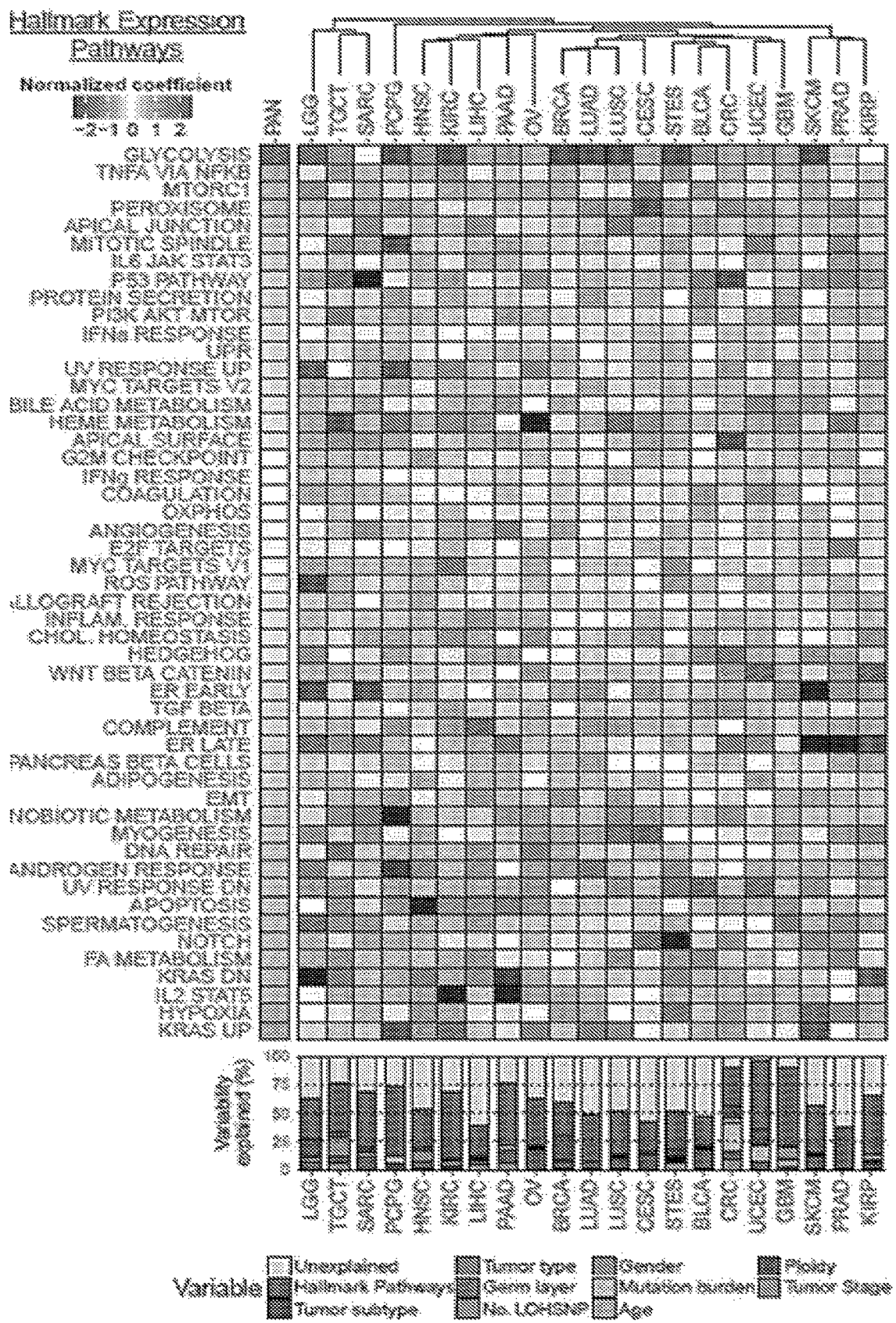
FIG. 10 shows a heatmap of machine learning regression coefficients representing the association between 50 hallmark pathways expression levels and amplification levels in the pan-cancer cohort (PAN) and specific tumor types.

MYC has been implicated as a driver of transcriptional amplification in cell lines and it was found that its expression was linked to an increase in transcriptional output in vivo (p<2.2e−16), as shown in FIG. 9. In some cases, MYC copy number on its own was found to be insufficient, and, conversely, there were many tumors whose transcriptional output appeared to be independent of their MYC expression. For this reason, additional expression pathways were discovered to explain the ~60% of variability that had been unaccounted for. Using machine learning regression models, the associations between the system 200 and established hallmark signalling pathways across the whole cohort (pan-cancer), then within individual tumor types (restricting the analysis to types with >80 samples). Several oncogenic signalling pathways, such as the TNFa/NFkB and MTORC1 pathways, emerged as significantly associated with levels outputted by the system 200, as shown in FIG. 10. By far the strongest association with amplification was seen for the glycolytic pathway. In over two thirds of the tumor types in the pan-cancer cohort, glycolysis was significantly associated with RNA output (within the top five pathways).

Figure 11:
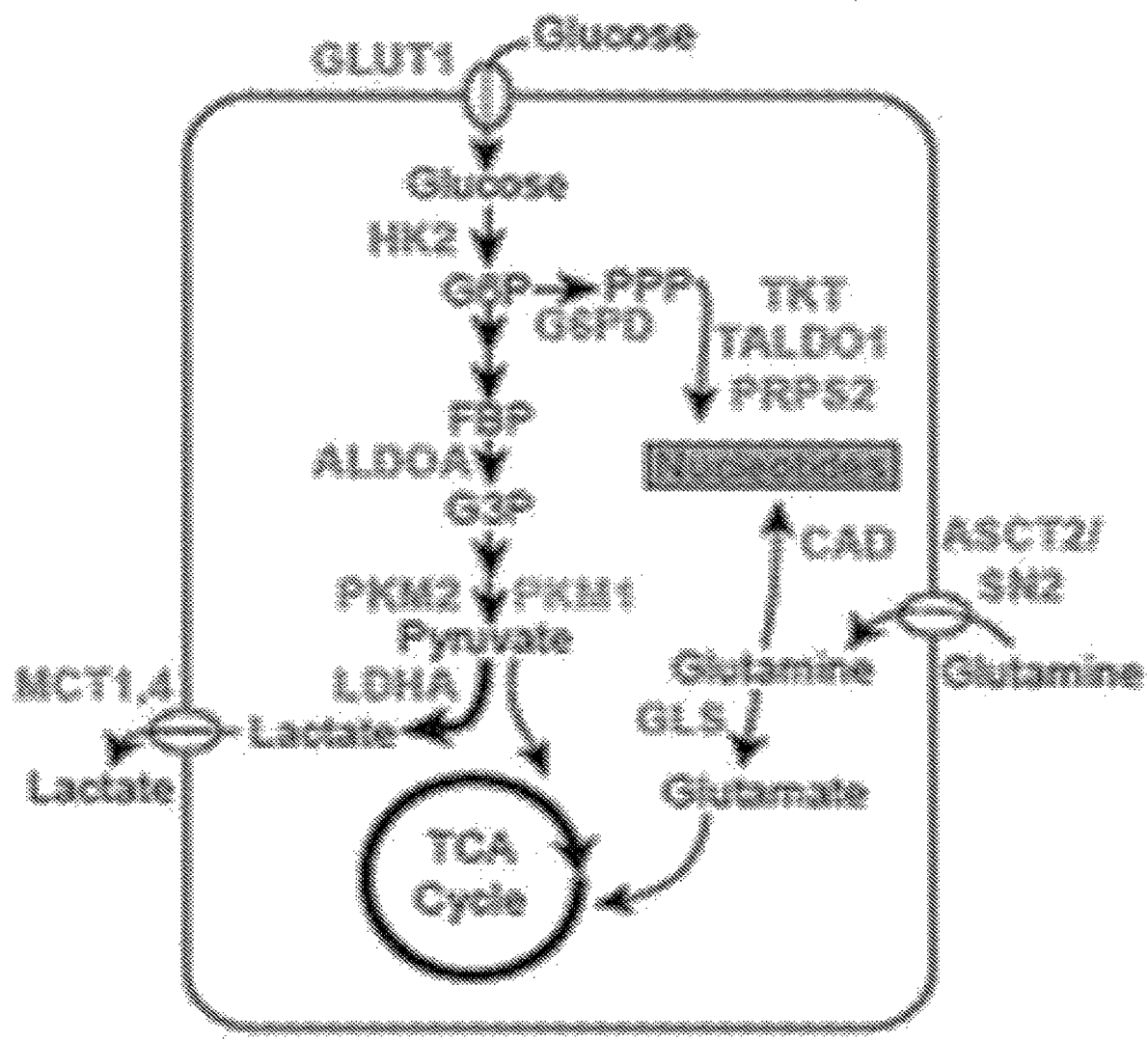
FIG. 11 shows a diagram depicting selected metabolic genes either enriched or depleted in transcriptionally amplified samples.

Having seen a widespread link between tumors' transcriptional output and their altered metabolism, as measured by glycolysis, the individual genes involved were examined. The expression of key genes implicated in aerobic glycolysis in cancer (the Warburg effect) and nucleotide synthesis were measured. Remarkably, nearly every Warburg gene was upregulated in transcriptionally amplified samples, suggesting that increased glucose consumption yields nucleotides as fodder for elevated transcription (9/11 genes), as shown in FIG. 11. Consistent with this, an increased expression of genes was observed that generate essential nucleotide precursors, including the provision of nitrogen and carbon for nucleotide synthesis. These findings were validated by measuring expression of KEGG metabolic pathways, confirming that simple sugar metabolism, as well as purine and pyrimidine metabolism are among the most significantly active pathways in transcriptionally amplified samples, as shown in FIG. 10.

Figure 12:
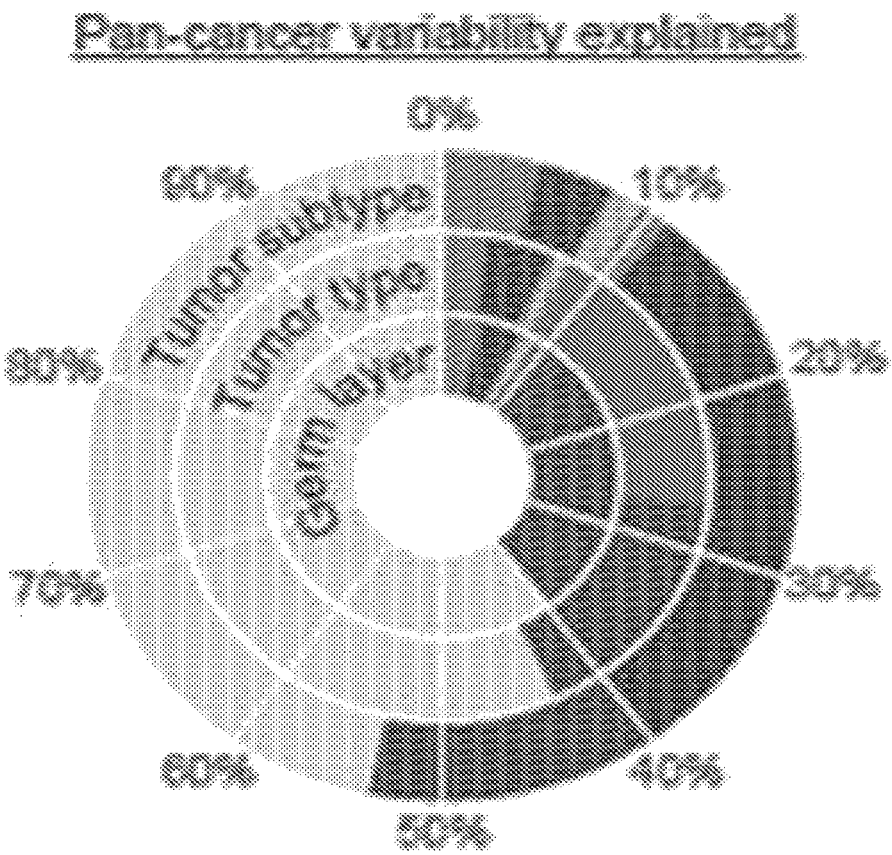
FIG. 12 shows a sunburst plot depicting the proportion of variability in RNA amplification explained by the developmental germ layer, tumor type, and tumor subtype models with hallmark pathway expression.

The results of the example experiments suggest increased glycolysis and increased glutamine uptake in transcriptionally amplified cancers. This further suggests that RNA amplification is caused by increased transcript production, rather than reduced turnover. Taken together, the expression of hallmark signaling pathways explained a large portion of a tumor's transcriptional amplification, as shown in FIG. 12. Even without accounting for a tumor's diagnosis, hallmark pathway expression accounted for almost 40% of the variability in its RNA output. A tumor's expression of cancer hallmarks explained as much of its RNA output as its subtype. Combining all factors together increased the variability explained to over 50%. The amount of variance explained by pathway expression varied from 27% to 69% in different tumor types, as shown in FIG. 10. In some cancers over 90% of the total variability could be explained, suggesting that, with the addition of gene expression pathways, global RNA output could be fully predicted.

Figure 41:
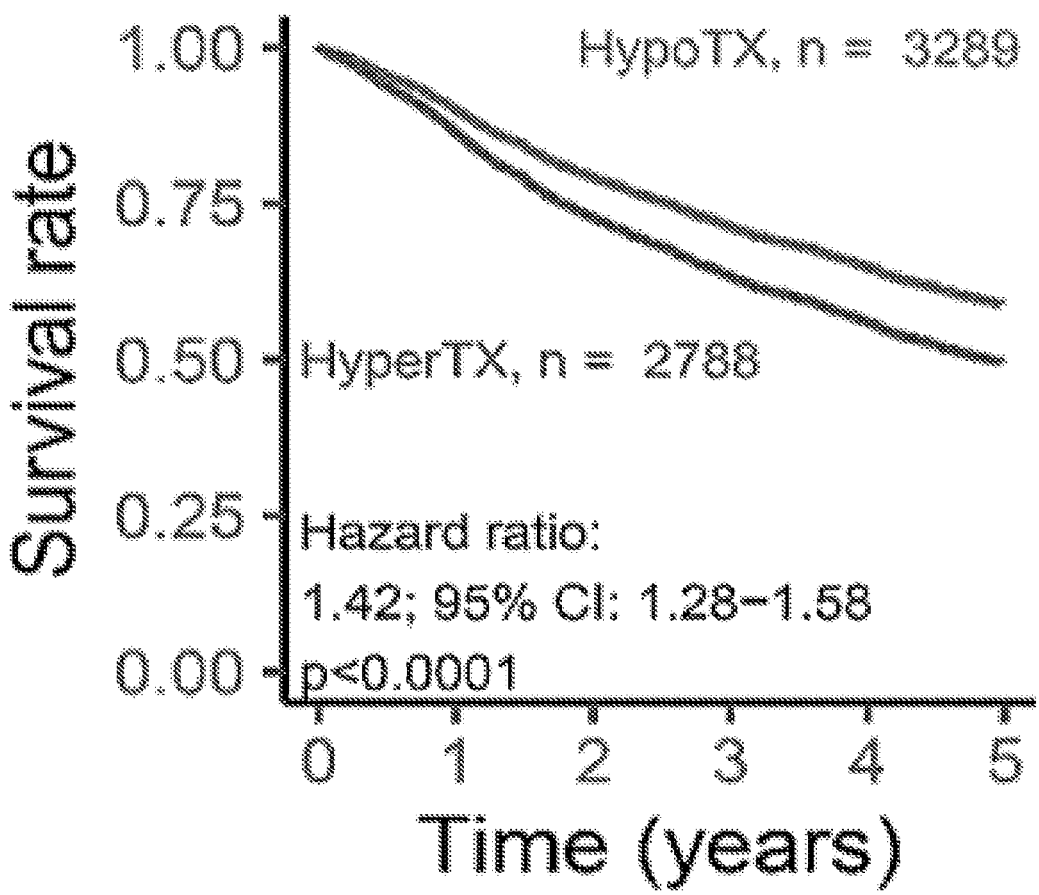
FIG. 41 shows a Cox adjusted survival curves for hyper- and hypotranscriptional groups in the pan-cancer cohort.
Figure 42:
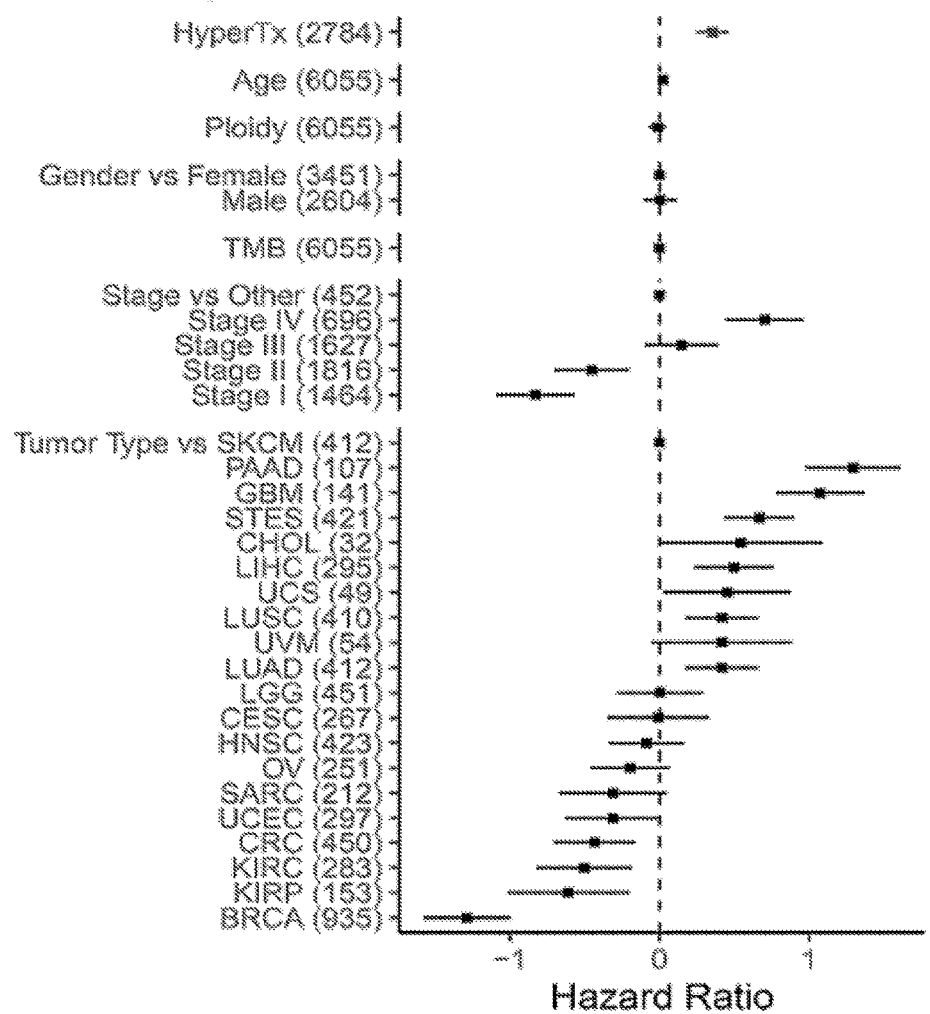
FIG. 42 shows a Forest plot showing hazard ratios for the pan-cancer cox regression model.

In the example experiments, patients were grouped into hyper- and hypotranscription groups using an automated threshold finding approach and survival analysis was performed (in cancers with sufficient numbers of events. Hypertranscription predicted worse overall survival across cancer (50% vs 59% cox-adjusted 5-year survival, as shown in FIG. 41. Patients with elevated RNA output had a 42% increased risk of mortality within the first five years of diagnosis—even when accounting for tumor type, mutation burden, tumor stage, and gender (HR: 1.42; 95% CI 1.28-1.58; P<0.0001), as shown in FIG. 42.

Figure 43:
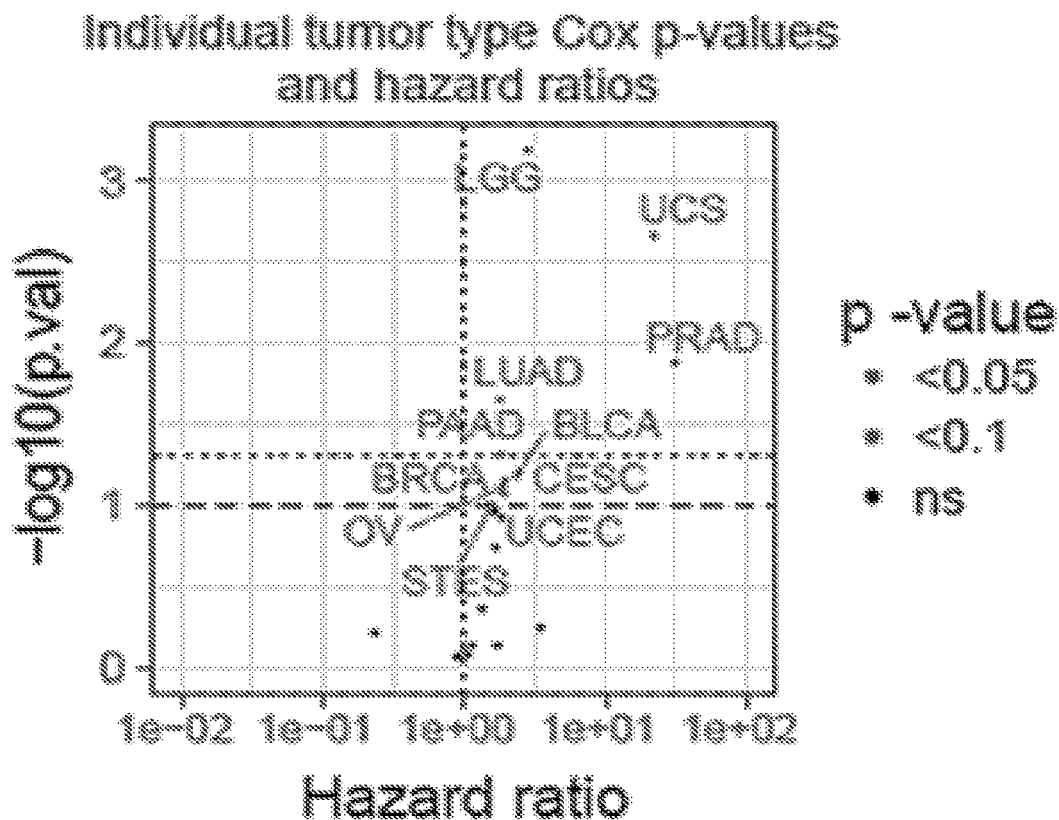
FIG. 43 shows a diagram of cox hazard ratios and associated p-values for high RNA amplification tumors across the TCGA cohort.

Extending this analysis to individual tumor types, multiple diagnostic groups in which patients with amplified cancers had worse survival, as shown in FIG. 43. In uterine carcinosarcoma, it was found that 100% of patients with highly amplified tumors succumb to disease within 5 years of diagnosis, compared to patients with lowly amplified tumors, of which 45% survive past 5-years (cox-HR=4.7, p<0.05). Other studies of this uterine carcinosarcoma cohort did not report significant associations between survival and several clinical and molecular features, highlighting that the system 200 can identify "hidden" tumor subtypes. Within dedifferentiated and pleomorphic liposarcomas, all patients with highly amplified tumors succumbed to disease within 5-years compared to patients with lowly amplified, of which 61% survived (HR=27.5, p<0.01).

The clinical classification of gliomas is by tumor grade. Low grade gliomas (LGG) are enriched for IDH1 or IDH2 mutations which lead to genomic hypermethylation. LGGs have improved survival compared to high-grade glioblastoma (GBM), and IDH mutations are associated with improved survival in both LGG and GBM. Consistent with this, GBMs often lack IDH mutations. Differentiating which LGGs will progress to GBM is a major challenge. Advantageously, LGG had significantly lower RNA amplification than GBM (p<0.0001), as shown in FIG. 7B. Moreover, analysis of all gliomas by molecular alterations revealed that tumors lacking IDH mutations were also those with higher RNA amplification (p<0.0001), as shown in FIG. 7C. Having established that use of the system 200 can stratify gliomas, it was determined that the system 200 can can discern subtypes within IDH mutant tumors. Within IDH mutant LGG, the presence of deletions on chromosomes 1p and 19q ("IDH-mutant+1p/19q codel" or oligodendrogliomas) represents a distinct clinical entity with favorable outcome. Within the oligodendrogliomas, the system 200 identified a new subclass with high RNA output and significantly worse survival (46% vs 95% survival; cox-HR=74.5, p<0.05).

Taken together, transcriptional output has prognostic utility that is both complementary to other approaches, but with greater precision and flexibility, and provides a substantially improved metric that can allow for better prognostication, above and beyond known tumor types and genetic markers.

Figure 18:
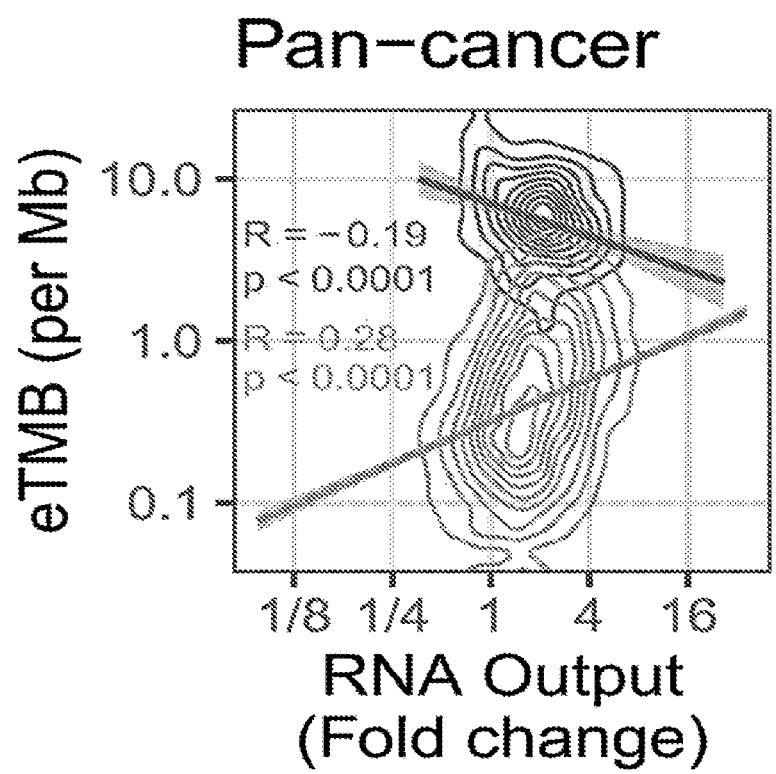
FIG. 18 shows a diagram of a pan-cancer correlation between expressed tumor mutation burden (eTMB) and hypertranscription for hypermutant (>10 mut/Mb) and non-hypermutant tumors (<10 mut/Mb)
Figure 19:
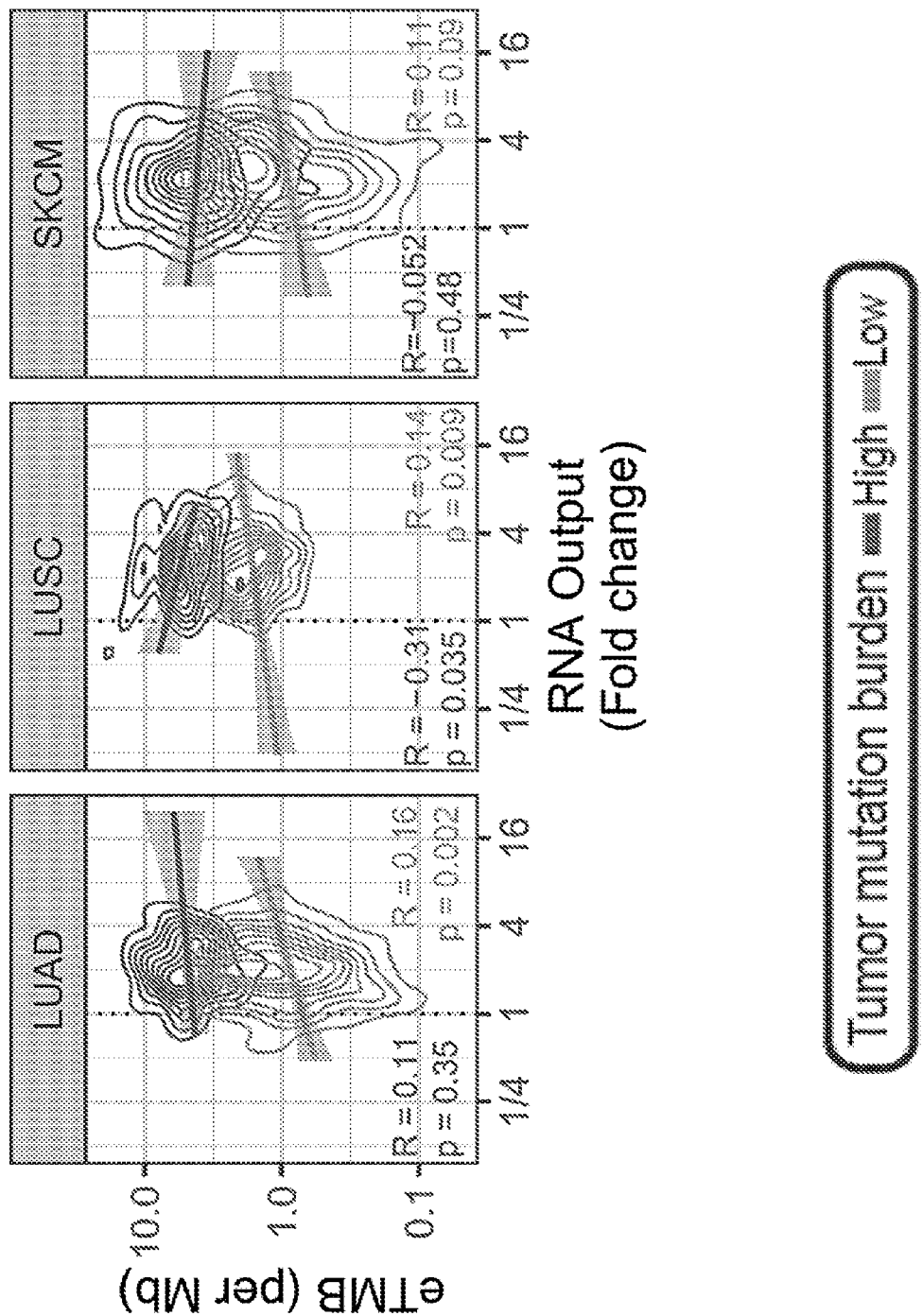
FIG. 19 shows a diagram of a correlation between eTMB and hypertranscription for hypermutant (>10 mut/Mb) and non-hypermutant tumors (<10 mut/Mb) in lung cancers (LUAD and LUSC), and skin melanoma (SKCM)

In the example experiments, the association between RNA abundance and response to immunotherapy was investigated. The success of immune checkpoint inhibition therapy (ICI) hinges on the immune system's ability to recognize tumor cells as foreign. For this reason, high genomic tumor mutation burden (TMB), yielding increased neoepitopes, is associated with ICI responsiveness. However, TMB alone is generally an imperfect predictor of ICI therapeutic response: low TMB (non-hypermutant) tumors can respond while many high TMB (hypermutant) tumors do not. The present inventors hypothesized that hypertranscriptional tumors, which in effect express more tumor-specific transcripts, including somatic mutations, would invoke a stronger immune response. To test this, the present inventors first quantified expressed tumor mutation burden (eTMB) in the TCGA cohort and searched for correlations with hypertranscription. In low TMB cancers (<10 coding mutations per megabase), eTMB increased with RNA output, while the opposite occurred in high TMB tumors (>10mut/Mb) (FIG. 18). Within lung and skin cancers, it was found that significant overlap in eTMB in tumors with low and high TMB tumors (FIG. 19). This suggested that expressed mutation burden due to hypertranscription may better identify patients that would respond to ICI therapy. TMB low tumors can effectively "look like" TMB high tumors in the setting of hypertranscription.

Figure 21A:
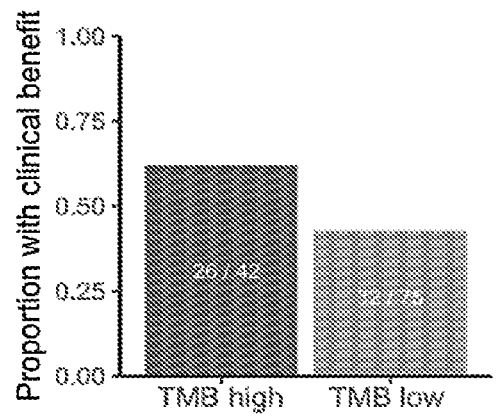
FIG. 21A shows a diagram of proportion of patients with clinical benefit from ICI in either high or low TMB groups.
Figure 21B:
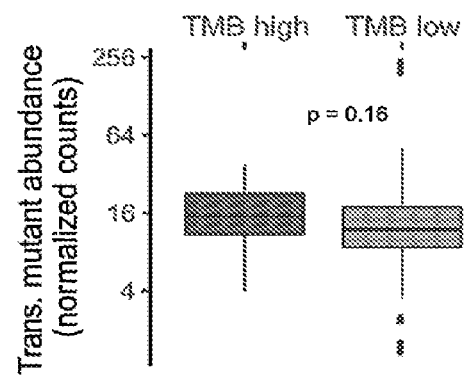
FIG. 21B shows a diagram of average transcriptional mutation abundance of TMB high and TMB low ICI patients (student's t-test, p=0.16)
Figure 21C:
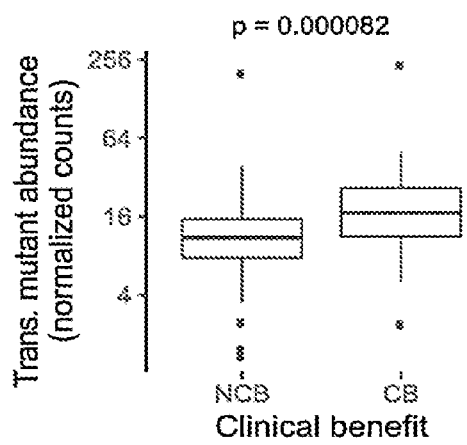
FIG. 21C shows a diagram of average transcriptional mutation abundance of ICI patients with and without clinical benefit to ICI.
Figure 21D:
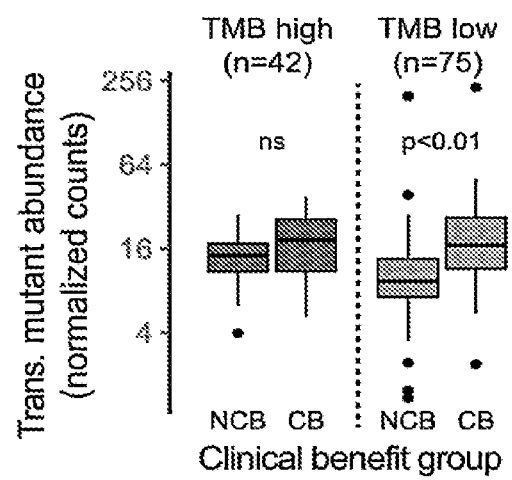
FIG. 21D shows a diagram of average transcriptional mutation abundance of ICI patients with and without clinical benefit to ICI split by TMB high and low groups.

To see if transcriptional mutant abundance was relevant in the context of ICI treatment, the example experiments investigated four clinical melanoma ICI cohorts for which both DNA and RNA-sequencing were conducted. Again, overlap in eTMB was observed for high and low TMB tumors (FIG. 20A). Overall, a greater proportion of high TMB patients had clinical benefit compared to low TMB patients (62% of hypermutant patients, and 43% of non-hypermutant patients, FIG. 21A). Since eTMB is simply a count of expressed mutations, it does not generally effectively capture how abundantly these mutations are expressed in the transcriptome. To measure true transcriptional mutant abundance, the present inventors integrated RNA output from the system 200, variant allele fractions, gene expression count data and sample purity. It was observed that there was no significant difference in transcriptional mutant abundance between low and high TMB tumors (FIG. 21B). However, transcriptional mutant abundance was significantly elevated in clinically benefitting patients (FIG. 21C). Upon closer inspection, it was found that expressed mutation abundance was significantly elevated in low TMB patients with clinical benefit (FIG. 21D). Patients with low TMB but high transcriptional mutant abundance were as likely to benefit from ICI as patients with high TMB patients (68% vs 62%, FIG. 20B). Overall, transcriptional mutant abundance had more predictive value for ICI patients, particularly able to identify non-hypermutant patients for whom ICI was effective (FIG. 20C).

The example experiments illustrate that there is elevated transcriptional output across human cancer. The pervasiveness of this phenomenon, seen in nearly every cancer type and enriched in patients with poor survival, suggests that increased global transcription is an essential feature of cancer. The system 200 advantageously provides a direct 'read out' of transcriptional amplification in primary tumors, which was found to explain differences in patient survival (e.g. in liposarcoma, uterine carcinosarcoma) and delineated new subtypes of cancer, even for tumor types that have been extensively and repeatedly genetically profiled (e.g. low-grade glioma).

Since the system 200, in some cases, determines the relative amounts of transcription between the tumor from non-tumor cells, a certain amount of stromal contamination (or impurity) may be present. In an example, the system 200 could be used to profile two thirds of solid tumors, which had the requisite impurity and/or harbored enough mutations or regions of LOH. This example is relatively conservative and there are likely more transcriptionally amplified tumor types that could be identified using the system 200. The approach of the system 200 also means that, in addition to controlling for the confounding effects of copy number, ploidy and clonality, the tumor cells' transcription has been normalised to that of the surrounding stroma. Thus, the system 200 can output the global transcription of the tumor "over and above" that of the patient's tissue matched stroma. This output may be important when considering the therapeutic window for transcriptional inhibitors (TIs).

For the purposes of illustration of the present embodiments, some of the present FIGS. will be described in greater detail. The following acronyms are used: CIMP=CpG island methylator phenotype, CIN=Chromosomal instable, DDLPS=Dedifferentiated liposarcoma, ESCC=Esophageal squamous cell carcinoma, GS=Genomically stable, LMS=Leiomyosarcoma, MFS/UPS=Myxofibrosarcoma and undifferentiated pleomorphic sarcoma (UPS), and MSI=Microsatellite instable.

FIGS. 3 to 5C illustrate an overview of an example of transcriptional output analysis with the system 200. FIG. 3 shows how transcriptional amplification occurs when cancer cells elevate their transcriptional output above normal cell levels (left). Upon RNA extraction from primary tumor tissue, transcriptional output per cell information is lost (middle). Cancer and normal cell specific transcripts can be identified using cancer-cell specific marker variants, such as somatic substitutions (Subs.) and LOH-SNPs (right). FIG. 4 shows an overview of how the system 200 measures transcriptional output in primary tumors. Positive variant allele fraction (VAF) shifts in the RNA of cancer-cell specific variants indicates that transcriptional output has increased. The present embodiments incorporate these variant allele fraction shift, along with 9 purity, ploidy, and local variant copy number information, to produce a fold amplification density distribution for each sample. Shown are representative samples with and without RNA 11 amplification. FIG. 5A shows a diagram of a validation example experiment involving mixtures of cellular equivalents of RNA from tumor and normal cells, simulating primary tumors of varying purity. These mixtures were then sequenced and processed by the system 200. HCC2218 and HCC1143 are breast cancer cell lines. UW228 is a medulloblastoma cell line with and without activated MYC (UW228 and UW228_MYC). FIG. 5B shows fold amplification levels of the cell lines used based on cell counting and direct RNA quantification. FIG. 5C illustrates RNA amplification derived tumor RNA content compared to actual RNA content demonstrating very high concordance.

FIGS. 6 to 8C illustrate elevated transcriptional output in human cancer. FIG. 6 is a histogram showing an example of the transcriptional output of 7,494 cancers. Dotted line indicates 1-fold amplification level (i.e. no RNA amplification). The distribution is shifted to the right, indicating widespread RNA amplification. FIG. 7A shows an example of RNA amplification levels of cancers (expressed as fold change), grouped by whether the tumors have undergone whole genome doubling. FIG. 8A shows proportion of variability in RNA amplification for all tumors. FIG. 7B shows an example of fold amplification levels of cancers by their tumor type and FIG. 8B shows the proportion of variability explained in fold amplification levels modeled using tumor type. FIG. 7C shows an example of fold amplification levels of selected cancer types by their subtype and FIG. 8C shows the proportion of variability explained in fold amplification levels modeled using tumor subtypes.

FIGS. 9 to 12 show an example of gene expression analysis revealing pathways associated with transcriptional amplification. FIG. 9 shows correlation between MYC expression and RNA amplification. FIG. 10 shows a heatmap of machine learning regression coefficients representing the association between 50 hallmark pathways expression levels and amplification levels in the pan-cancer cohort (PAN) and specific tumor types. FIG. 10 also shows proportion of variability explained in specific tumor types, including hallmark pathway expression. FIG. 11 shows a diagram depicting selected metabolic genes either enriched or depleted in transcriptionally amplified samples. Of note are the increased expression of the pentose phosphate pathway genes (G6PD, TKT, TALDO1—necessary for the generation of ribose-5-phosphate), glutamine transporters (ASCT2, SN2—which provide nitrogen and carbon for nucleotide synthesis) and of PRPS and CAD, which are rate limiting for purine and pyrimidine synthesis. FIG. 12 shows a sunburst plot depicting the proportion of variability in RNA amplification explained by the developmental germ layer, tumor type, and tumor subtype models with hallmark pathway expression.

Figure 13A:
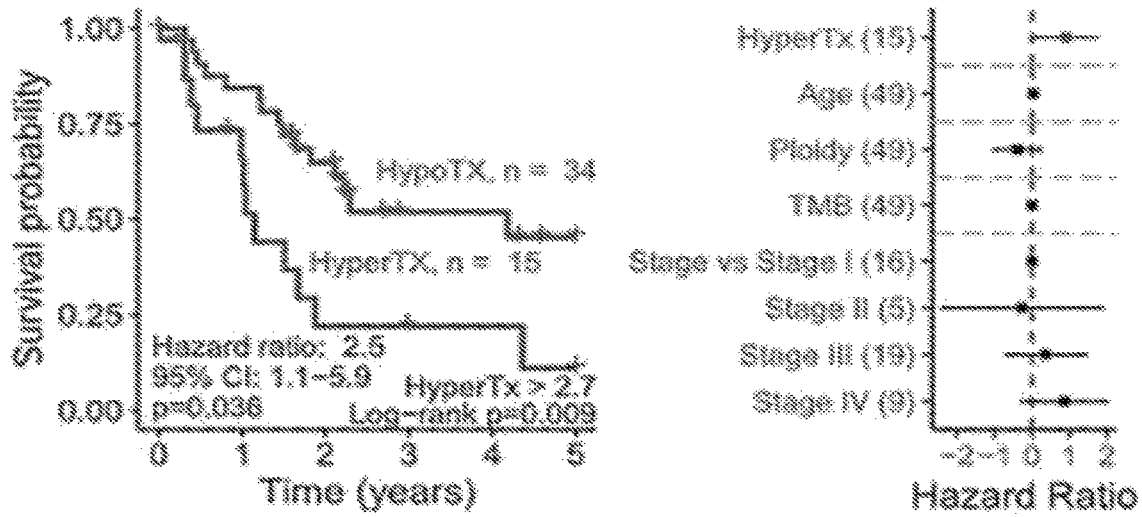
Figure 13B:
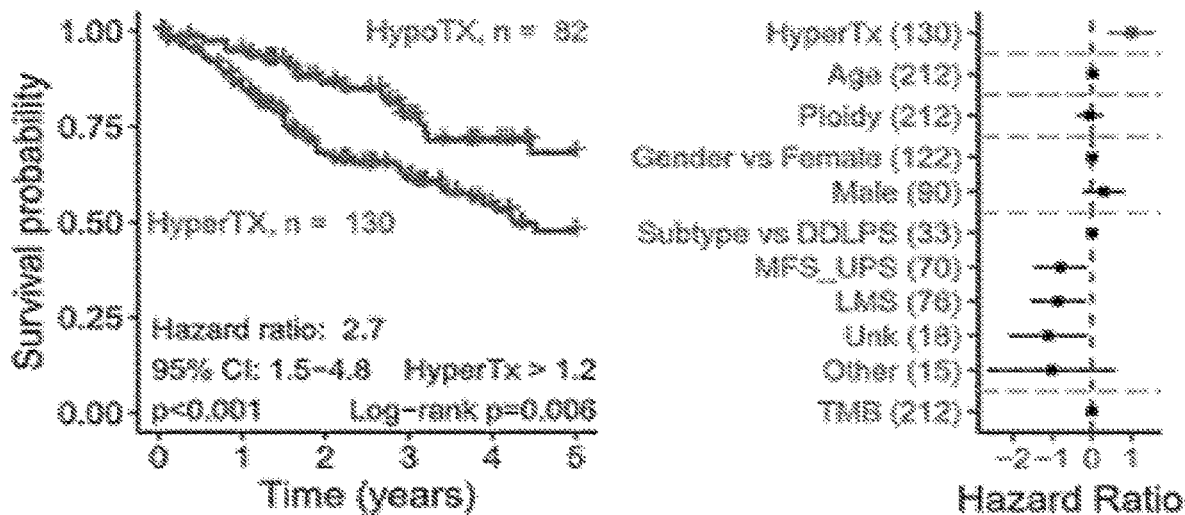
FIG. 13B shows bone sarcoma.
Figure 14A:
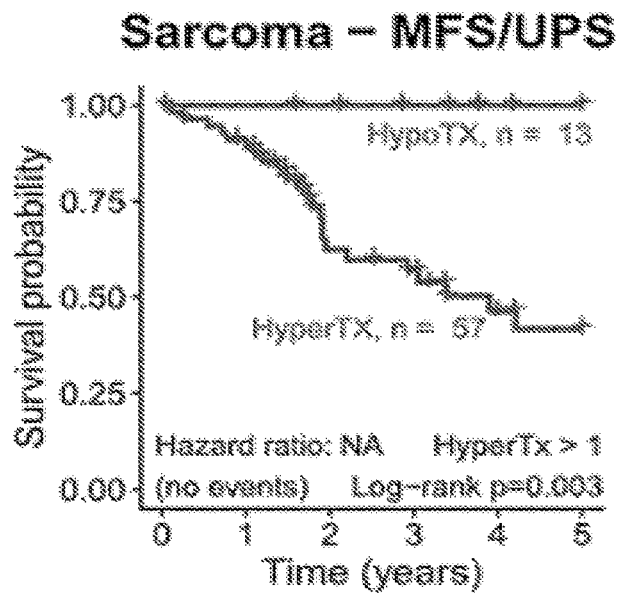
FIG. 14A shows myxofibroid and undifferentiated pleomorphic sarcoma.
Figure 14B:
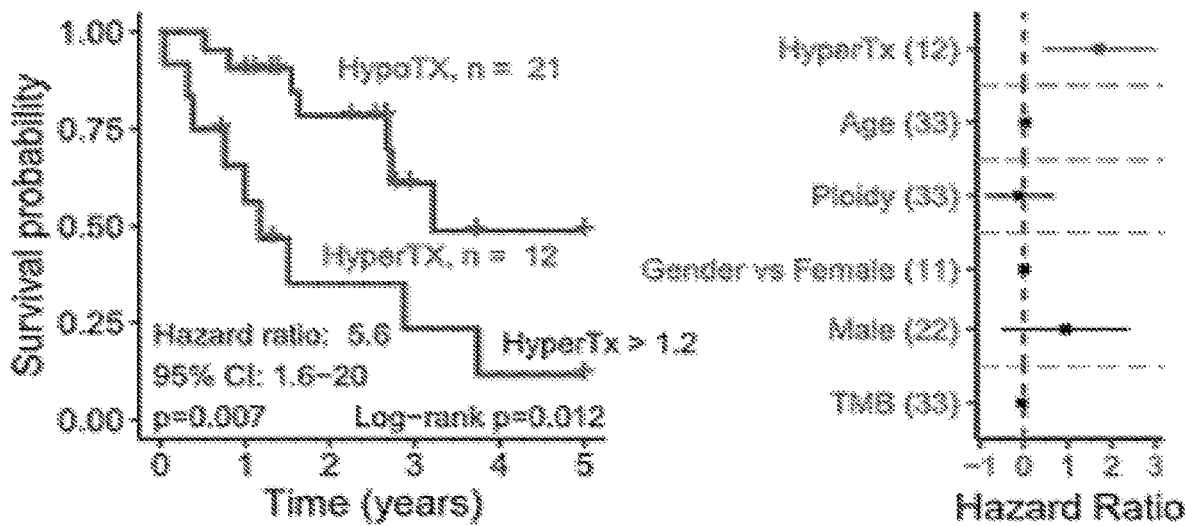
FIG. 14B shows dedifferentiated liposarcoma.
Figure 15:
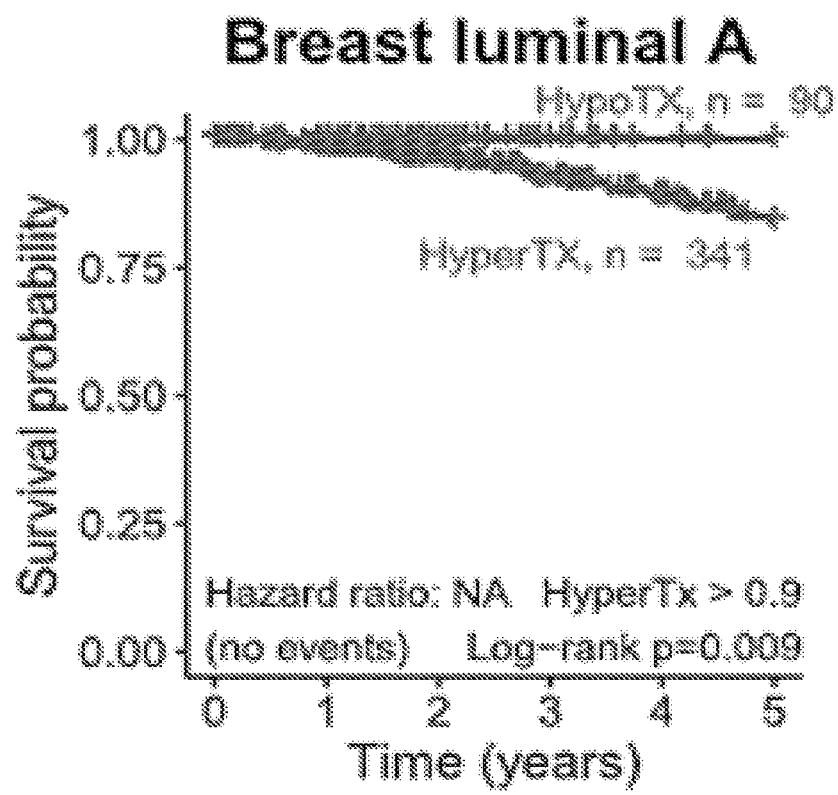
Figure 16:
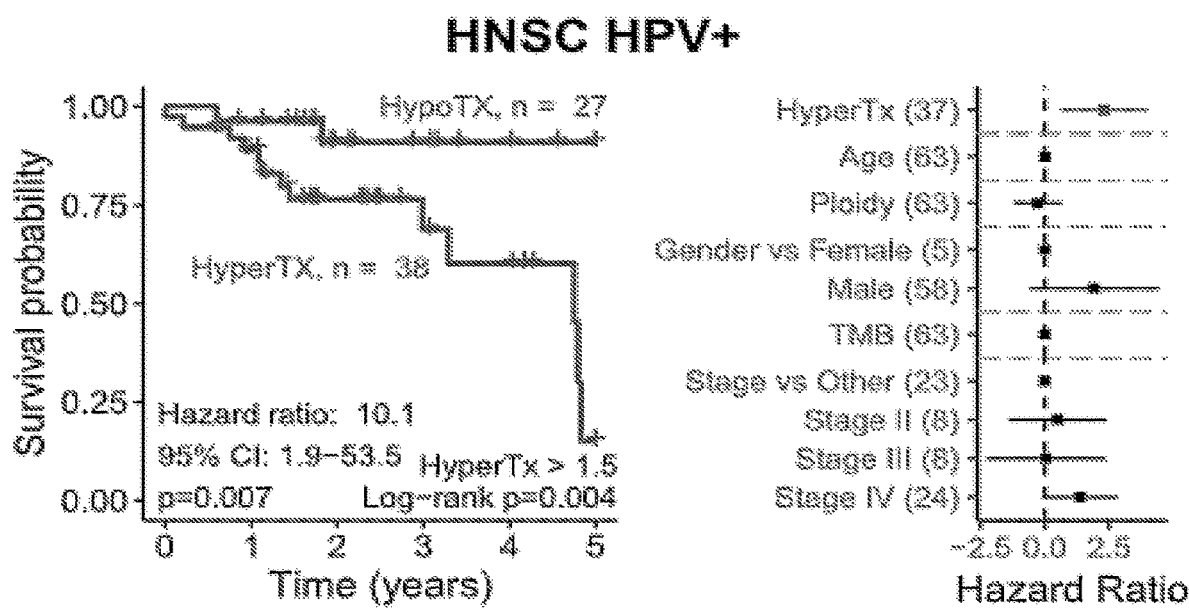
Figure 17:
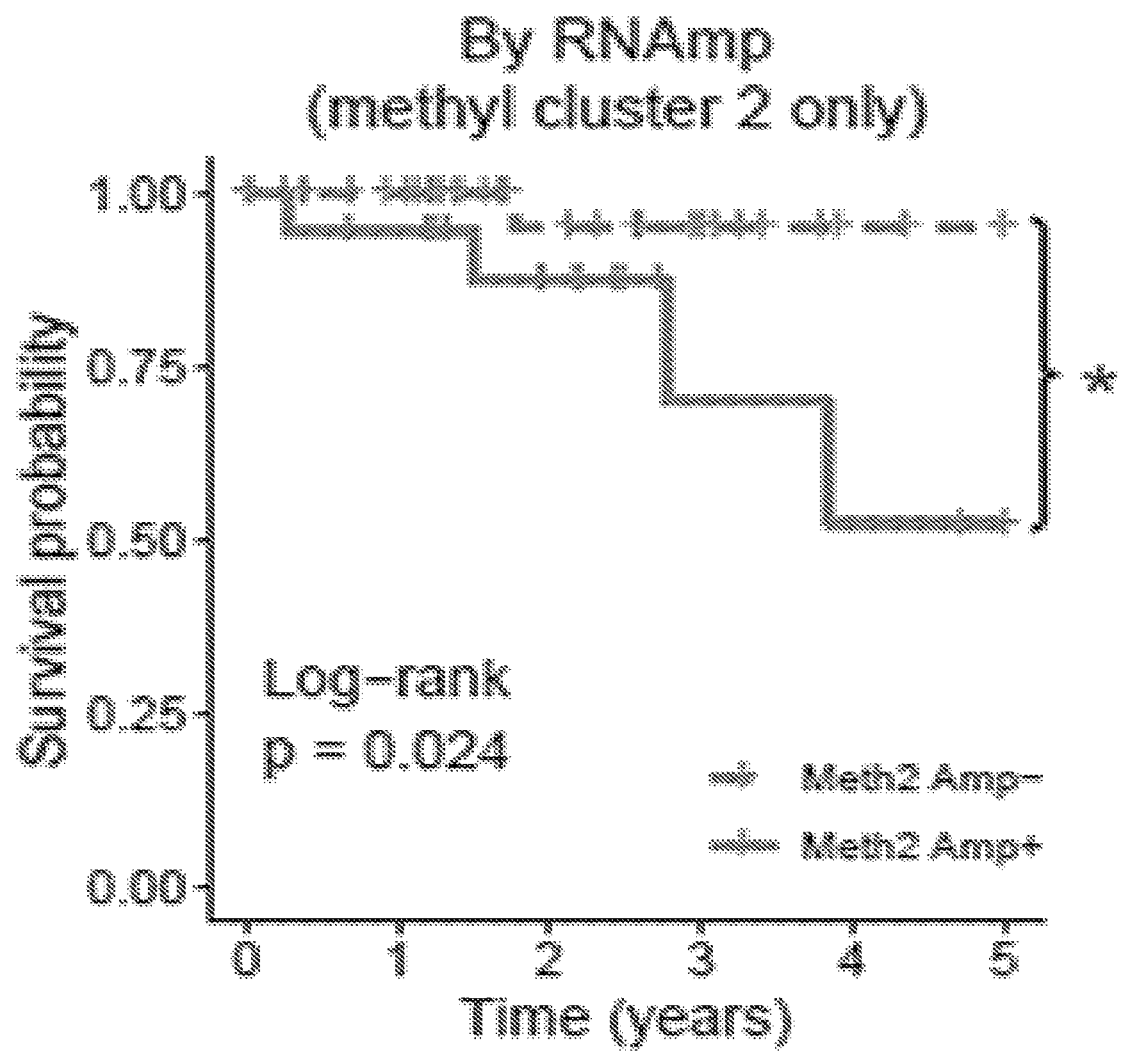
FIG. 17 shows a Kaplan-Meier survival curve of the IDH-mutant 1p/19q codeletion methylation cluster 2 grouped by RNA amplification showing significant survival differences.

FIGS. 13A to 16 show an example experiment illustrating hypertranscription defining patient subgroups with worse overall survival, where FIG. 13A shows uterus carcinosarcoma, FIG. 13B shows bone sarcoma, FIG. 14A shows myxofibroid and undifferentiated pleomorphic sarcoma, FIG. 14B shows dedifferentiated liposarcoma, FIG. 15 shows luminal A breast cancer, and FIG. 16 shows HPV+ head and neck squamous cell carcinoma. Each figure shows a Kaplan-Meier survival plot. FIGS. 13A, 13B, 14B and 16 also show Cox regression model hazard ratios. Error bars on all hazard ratio coefficients represent the 95% CI.

FIGS. 18 to 21D show an example of expressed mutation burden and RNA amplification as biomarkers for immunotherapy response. FIG. 18 shows pan-cancer correlation between expressed tumor mutation burden (eTMB) and hypertranscription for hypermutant (>10 mut/Mb) and non-hypermutant tumors (<10 mut/Mb). FIG. 19 shows correlation between eTMB and hypertranscription for hypermutant (>10 mut/Mb) and non-hypermutant tumors (<10 mut/Mb) in lung cancers (LUAD and LUSC), and skin melanoma (SKCM). FIG. 20A shows correlation between eTMB and hypertranscription for hypermutant (>10 mut/Mb) and non-hypermutant tumors (<10 mut/Mb) in four melanoma ICI cohorts. FIG. 20B shows proportion of patients with clinical benefit from ICI in high and low TMB groups split by transcriptional mutant abundance levels. FIG. 20C shows log odds of response to ICI for different tumor mutation burden markers. Transcriptional mutant abundance is an overall better predictor of ICI response compared to genomic TMB. FIG. 21A shows proportion of patients with clinical benefit from ICI in either high or low TMB groups. TMB high is defined as greater than 10 mutations per megabase. FIG. 21B shows average transcriptional mutation abundance of TMB high and TMB low ICI patients (student's t-test, p=0.16). FIG. 21C shows average transcriptional mutation abundance of ICI patients with and without clinical benefit to ICI. Patients with clinical benefit have significantly increase average mutation abundance (student's t-test, p=0.000082). FIG. 21D shows average transcriptional mutation abundance of ICI patients with and without clinical benefit to ICI split by TMB high and low groups. Patients with low TMB but high transcriptional mutant abundance were as likely to benefit from ICI as patients with high TMB patients. In the above diagrams, CB refers to clinical benefit and NCB refers to no clinical benefit.

Figure 25:
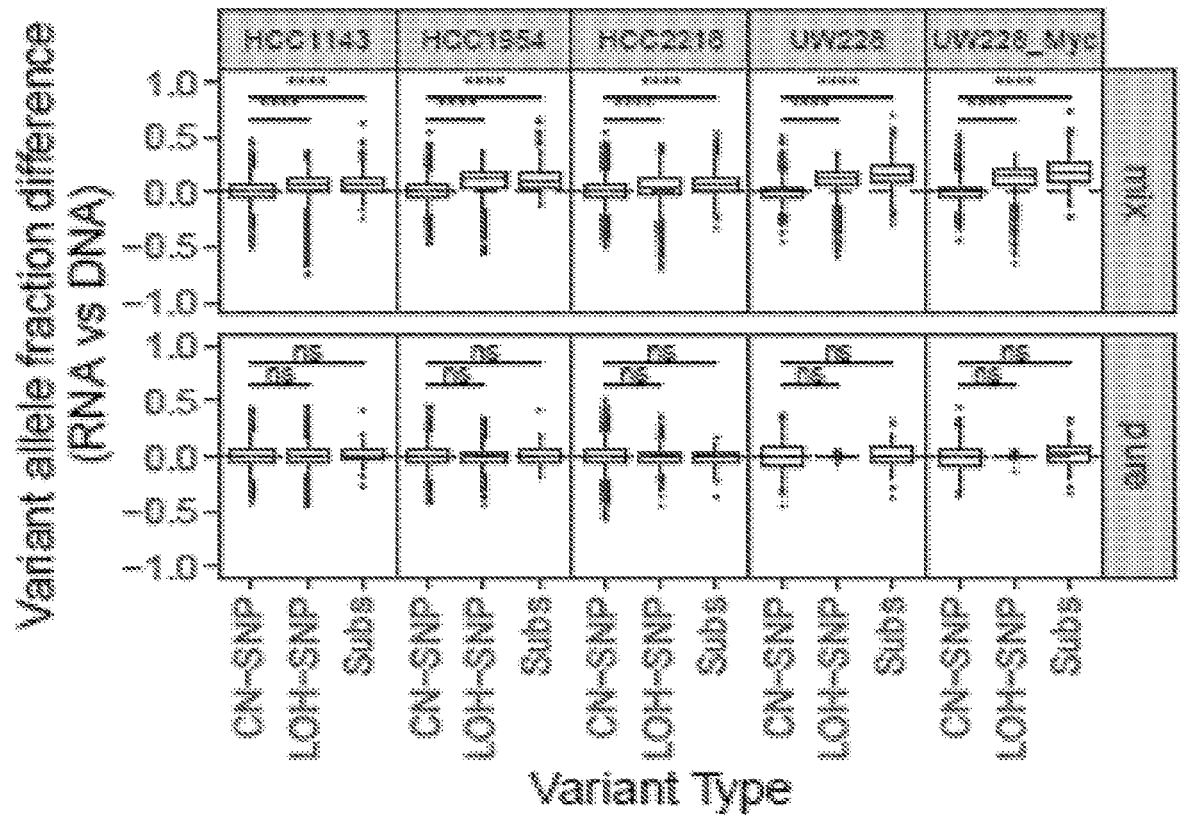
FIG. 25 shows variant allele fraction difference boxplots of copy-neutral SNP (CN-SNP), LOH-SNP, and somatic substitution variants of each cell line used in either cell mixtures, or purified cell lines.

FIGS. 22 to 30 show an example experimental validation of the system 200. FIG. 22 shows a western blot of Myc induction in medulloblastoma cells (UW228) and FIG. 23 shows qRT-PCR Myc mRNA expression. FIG. 24 shows RNA output per cell for each line tested: BRCA—Breast cancer, and Mb—Medulloblastoma. FIG. 25 shows variant allele fraction difference boxplots of copy-neutral SNP (CN-SNP), LOH-SNP, and somatic substitution variants of each cell line used in either cell mixtures, or purified cell lines. Note that every mixed cell line displays a larger proportion of reads reporting the variant in the RNA relative to DNA (top row), while the same is not true for pure cells (bottom). All comparisons are to the copy neutral single nucleotide polymorphisms (CN-SNP). FIG. 26 shows variant allele fraction difference boxplots of copy-neutral SNP (CN-SNP), LOH-SNP, and somatic substitution variants of each cell line used in either cell mixtures, or purified cell lines split by missense and silent variant types. Note that no difference is seen between missense and silent (synonymous) variants. FIG. 27 shows RNA fold amplification distributions for each cell mixture. FIG. 28 shows RNA fold amplification distributions for each cell mixture split by LOH SNP and somatic substitution variant types. FIG. is a barplot depicting transcriptional amplification in Myc containing UW228 cells versus wild type UW228 cells. FIG. 30 shows in-silico tumor RNA content calculations for different amplification levels and purity levels.

FIGS. 31A to 35 show an example of elevated transcriptional output in human cancer. FIG. 31A shows DNA and RNA variant allele fraction distributions for tumor specific (LOH SNPs and SNVs) and non-tumor specific variant types (diploid SNPs). As expected, diploid SNPs are centered at 0.5 and show no difference between RNA and DNA, indicating equivalent proportions, while cancer-cell specific markers have a higher VAF in the RNA. FIG. 31B shows missense and silent mutation DNA and RNA variant allele fraction density distributions. FIG. 32 shows correlation between RNA amplification values derived independently for LOH-SNP variants and somatic substitution variants including tumors with at least 15 of each variant type. FIG. 33 shows variability explained in RNA amplification levels before and after adjusting for tumor purity. FIG. 34 shows RNA amplification levels across different purity levels. FIG. 35 shows the proportion of variability in RNA amplification explained by subtype within selected cancer types.

Figure 36:
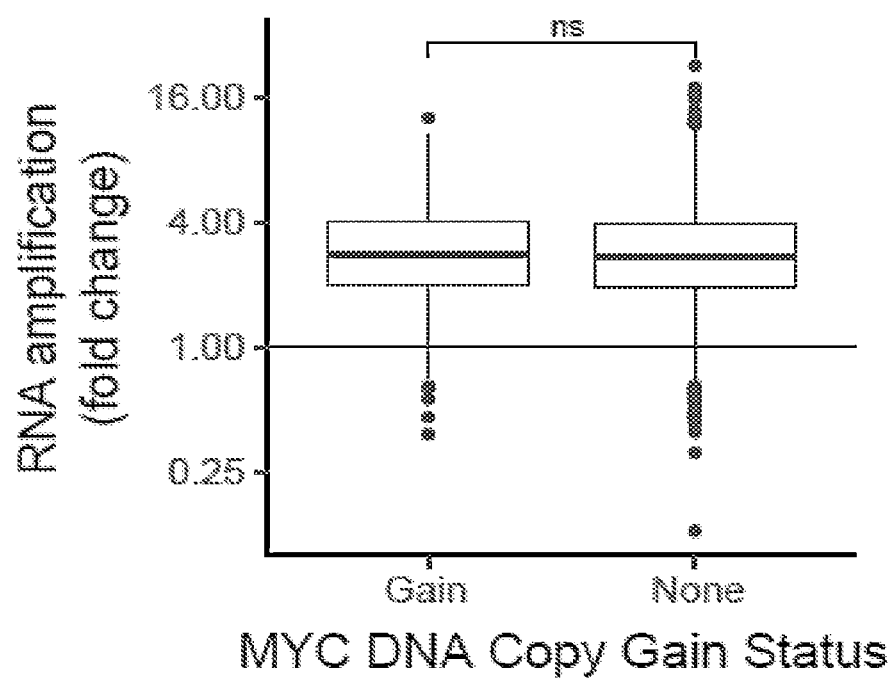
FIG. 36 shows a boxplot depicting RNA amplification levels of tumors with and without MYC copy gains.
Figure 37:
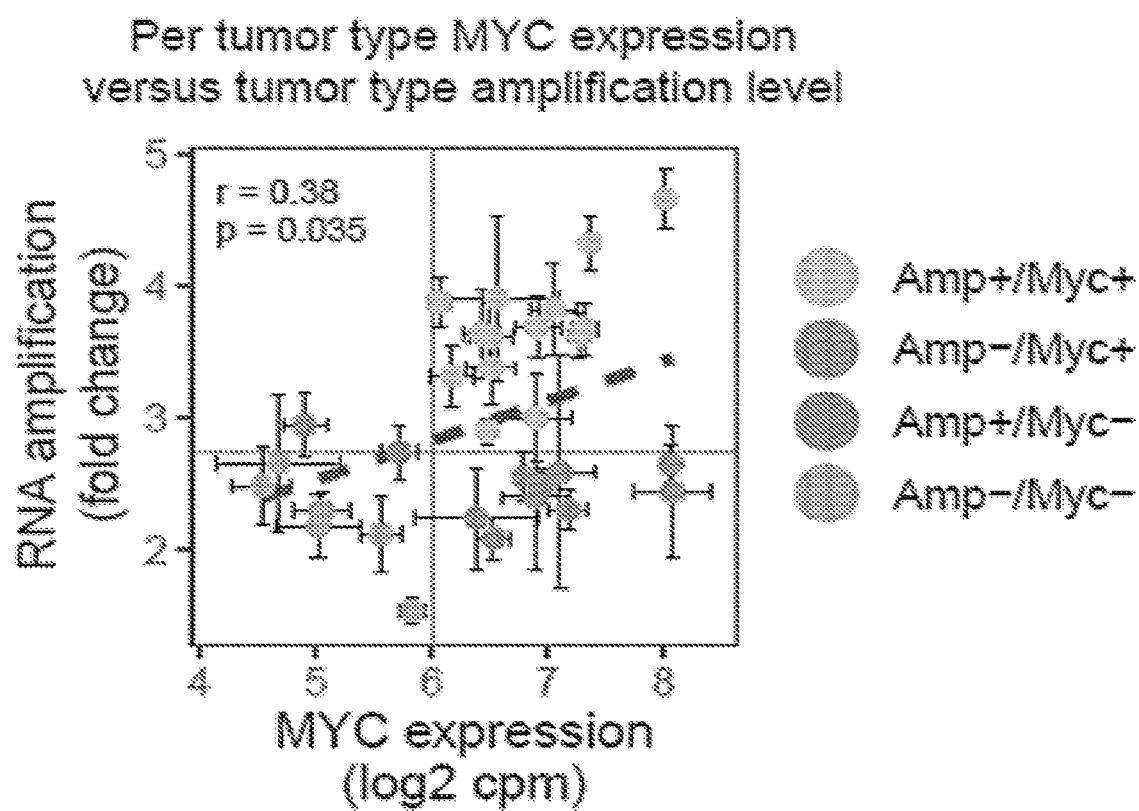
FIG. 37 shows a diagram of correlation between per tumor type mean MYC expression and RNA amplification levels.

FIGS. 36 and 37 show an example of MYC expression and copy status in relation to tumor RNA amplification. FIG. 36 shows a boxplot depicting RNA amplification levels of tumors with and without MYC copy gains. FIG. 37 shows correlation between per tumor type mean MYC expression and RNA amplification levels; highlighting that high MYC does not necessarily lead to high transcriptional output. Each circle represents one tumor type.

Figure 38:
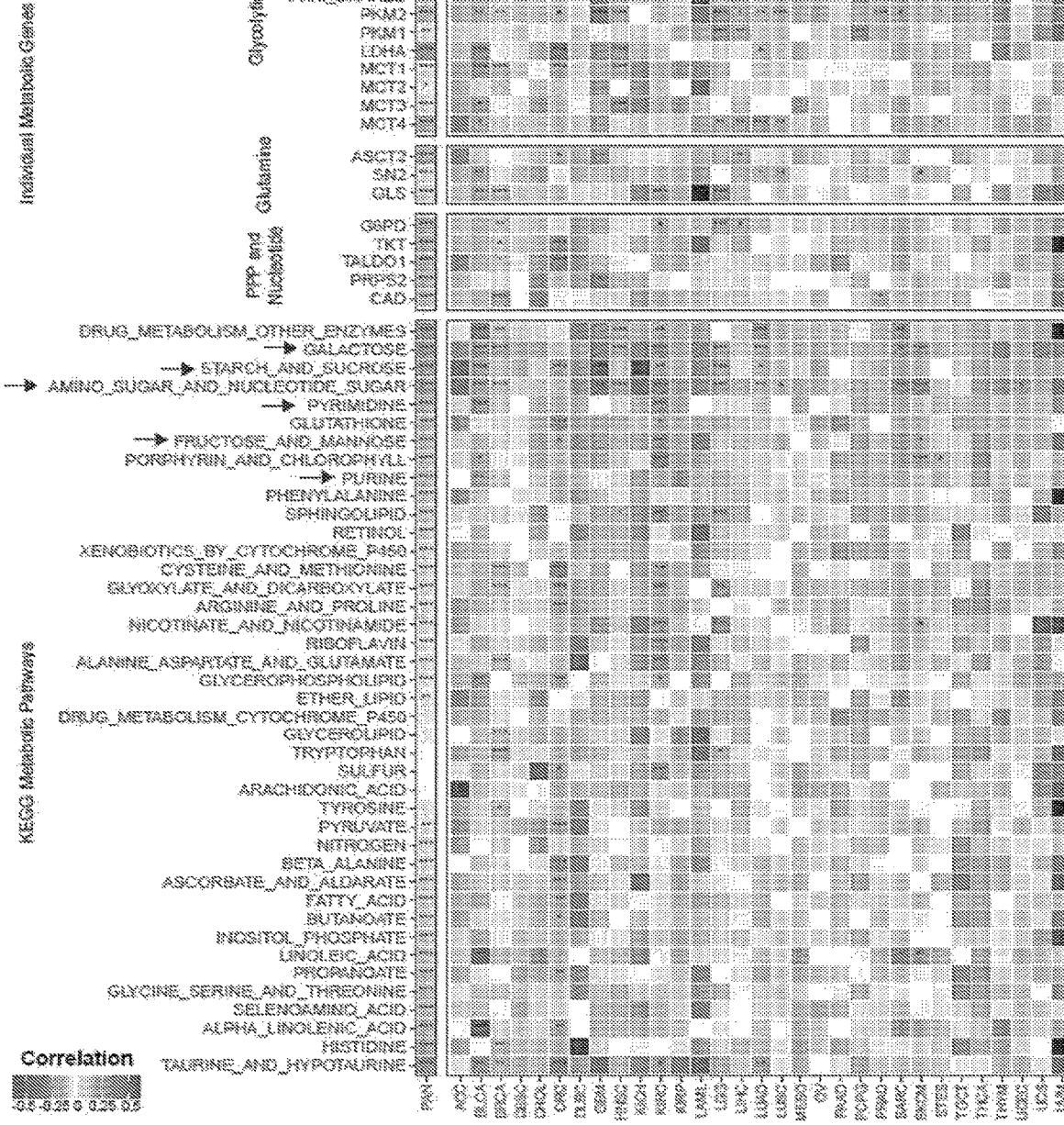
FIG. 38 shows a diagram of correlation between selected metabolic genes and transcriptional output, and correlation between KEGG metabolic pathways and transcriptional output.
Figure 39:
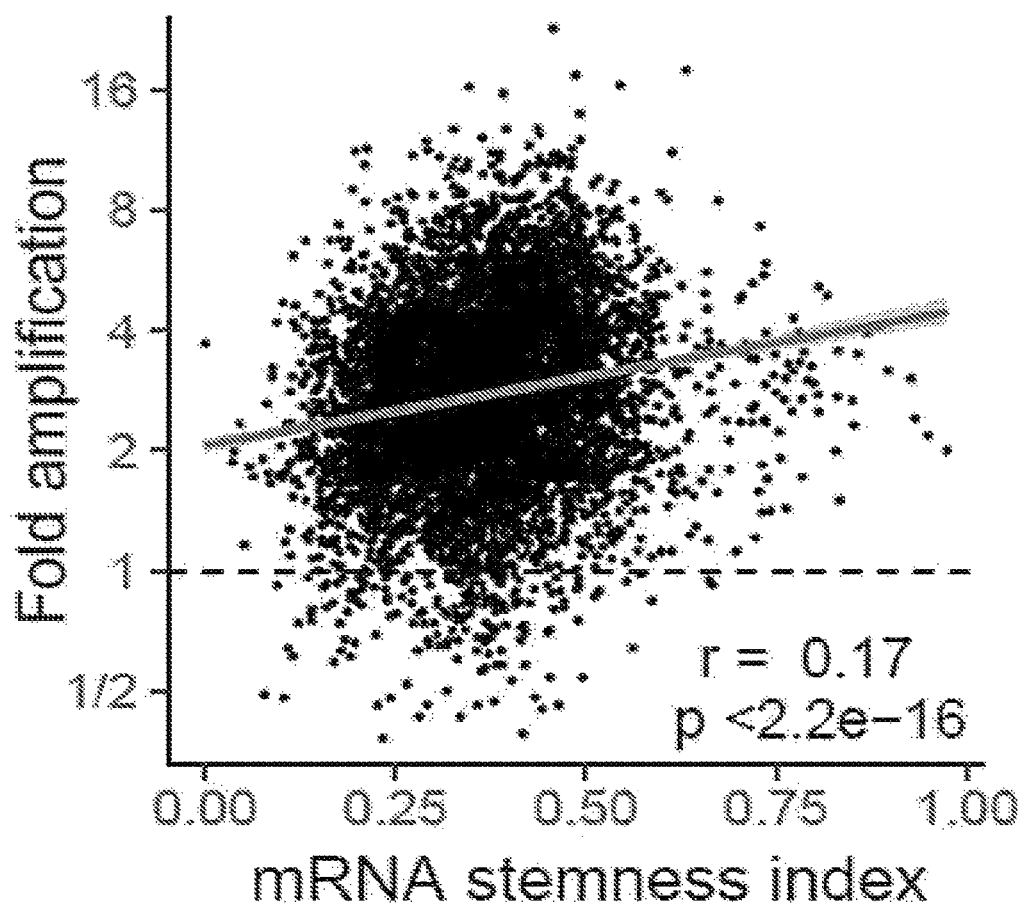
FIG. 39 shows a diagram of correlation between mRNA stemness index scores and RNA amplification.
Figure 40:
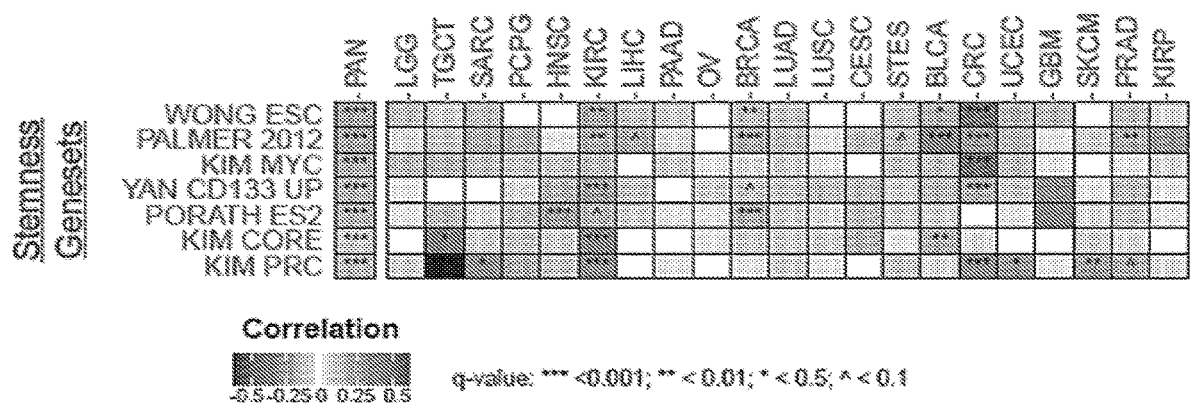
FIG. 40 shows a heatmap depicting the correlation values and significance for selected stemness genesets and RNA amplification.

FIGS. 38 to 40 show an example of gene expression analysis revealing pathways associated with transcriptional amplification. FIG. 38 shows correlation between selected metabolic genes and transcriptional output, and correlation between KEGG metabolic pathways and transcriptional output. The simple sugar and nucleotide pathways are highlighted by arrows, all of which are significantly enriched. FIG. 39 shows correlation between mRNA stemness index scores and RNA amplification. FIG. 40 shows a heatmap depicting the correlation values and significance for selected stemness genesets and RNA amplification.

Figure 44:
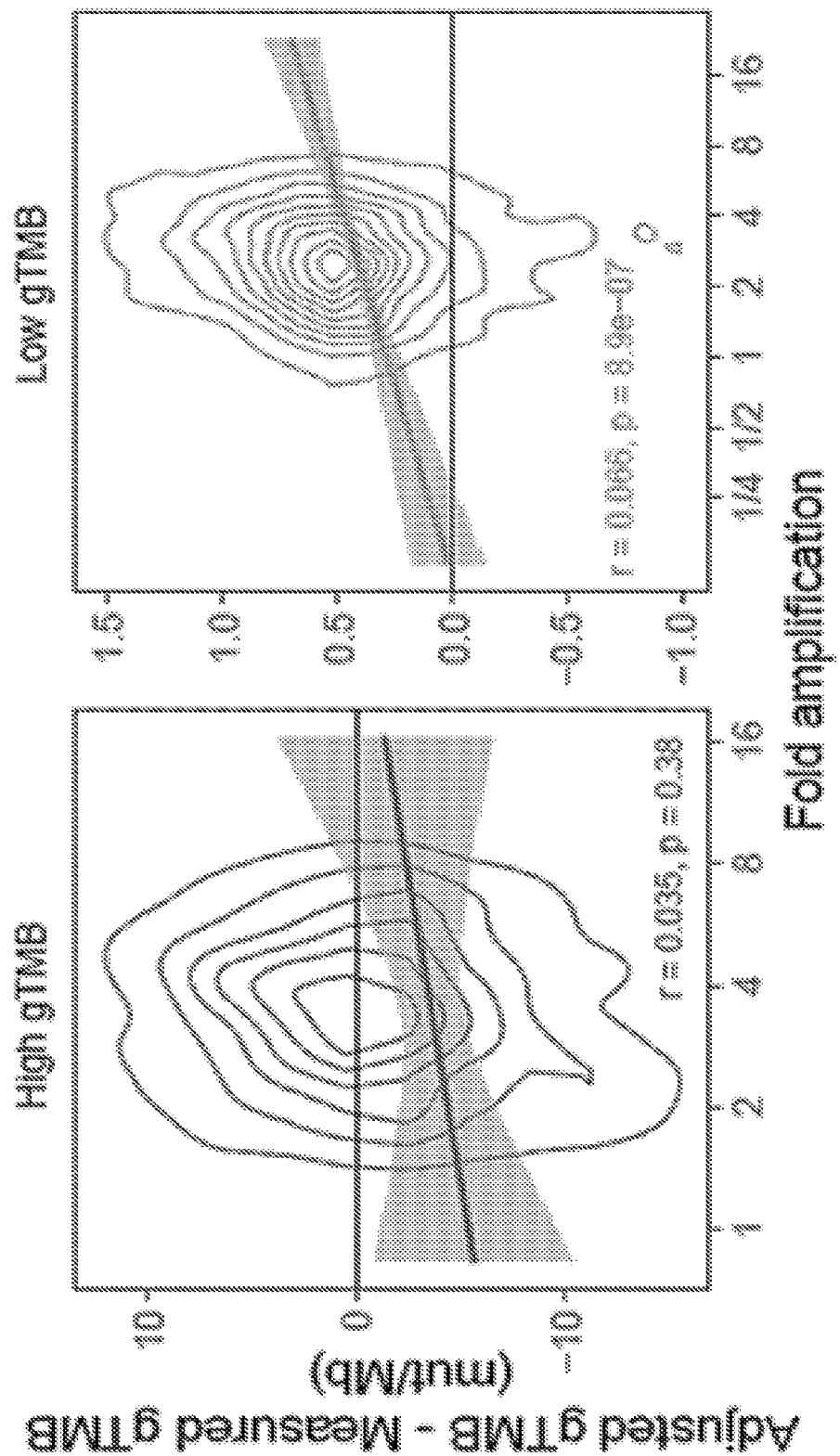
FIG. 44 shows a diagram of correlation between the adjusted genomic tumor mutation burden (gTMB) and measured gTMB difference and RNA amplification for high and low gTMB tumors.

FIGS. 41 to 44 show an example of analysis of transcriptional output and survival. FIG. shows a representation of an approach to define RNA amplification threshold. For each tumor type, a threshold is selected by maximizing the Youden's statistic, separating high and low amplified tumors on the basis of survival. FIG. 42 shows a Kaplan-Meier survival curve for the pan-cancer cohort grouped by RNA amplification. FIG. 43 shows cox-proportional hazards model for the pan-cancer cohort grouped by RNA amplification. FIG. 44 shows cox hazard ratios and associated p-values for high RNA amplification tumors across the TCGA cohort.

Figure 45:
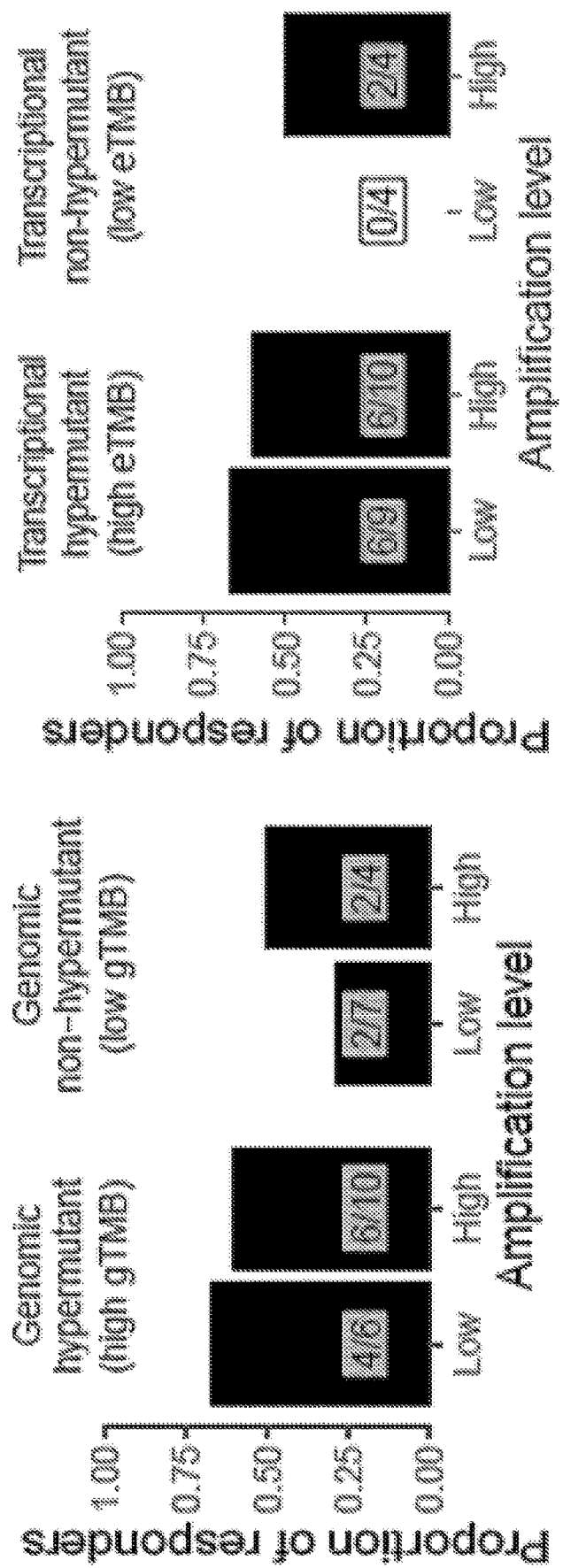
FIG. 45 shows a diagram of proportion of anti-PD1 responding patients broken down by RNA amplification and gTMB (left) or eTMB (right)
Figure 46:
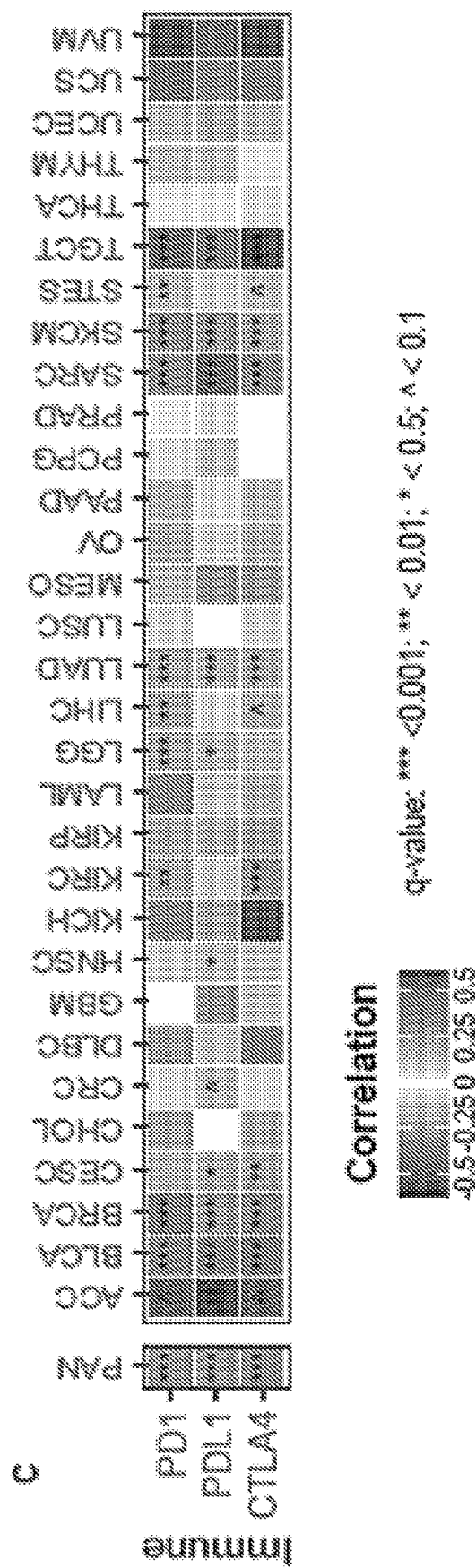
FIG. 46 shows a heatmap showing the correlation between immune markers and transcriptional output.

FIGS. 44 to 46 show an example of expressed mutation burden and RNA amplification as biomarkers for immunotherapy response. FIG. 44 shows correlation between the adjusted genomic tumor mutation burden (gTMB) and measured gTMB difference and RNA amplification for high and low gTMB tumors (i.e. hypermutated and non-hypermutated). FIG. 45 shows proportion of anti-PD1 responding patients broken down by RNA amplification and gTMB (left) or eTMB (right). FIG. 46 shows a heatmap showing the correlation between immune markers and transcriptional output.

In the present embodiments, transcriptional mutant abundance refers to the average expression level of each mutation in a sample. In the example experiments, gene expression counts from each sample were normalized using GeTMM33. For each mutation, the present inventors estimated the transcriptional mutant abundance by first multiplying the normalized counts for the gene containing the mutation by the variant allele fraction of that mutation in the RNA. Then, a correction factor was applied that accounts for tumor purity, hypertranscription, and tumor copy number related impact on expected mutation counts as follows:

$$\text{Transcriptional mutant abundance} = \\ VAF_{RNA} * \text{Counts} * \frac{1}{\text{correction factor}} \quad (14)$$

$$\text{Correction Factor} = \frac{\text{amp} * \text{total.}cn/2}{\text{amp} * \text{total.}cn/2 + 1 - \text{purity/purity}} \quad (15)$$

where amp*total.cn/2 is the tumor ploidy corrected hypertranscription level and 1−purity/purity is the normal:tumor cell ratio.

Cancer patients with tumors harboring many mutations (hypermutant) can have dramatic responses to immunotherapy; however, for non-hypermutant tumors responses are widely variable. An embodiment of the present disclosure can be used to identify patients with non-hypermutant tumors that will respond to immunotherapy, thereby increasing the number of people benefiting from this therapy. This embodiment can include measuring the abundance of mutant alleles in the tumor. This measurement is corrected for gene length and is highly correlated with measurements derived from the techniques of the system 200 described herein. In fact, the output of the system 200 can be used as part of calculating the tumor's mutation abundance. In particular, the system 200 can be used to determine the proportion of reads that derive from the tumor, which guards against the confounding effects of tumor purity. The mutation abundance is summed over all mutations (i), as per the formula provided below, where p is the sample's purity, $CN_{Tumor,i}$ is the tumor's total copy number at the locus of mutation i, $A_i$ is the abundance of mutation i (GeTMM normalized), $VAF_i$ is the Variant allele frequency of mutation i, and amp is hypertranscription level of the tumor. Num(I) is the number of expressed mutations present in the tumor.

$$\frac{\sum_i \frac{A_i VAF_i}{\text{amp}\left(\frac{CN_{Tumor,i}}{2}\right)}}{\text{amp}\left(\frac{CN_{Tumor,i}}{2}\right) + \frac{1-p}{p}}$$
$$num(I)$$

As can be seen in FIGS. 20B and 20C, with the approach of this embodiment, mutation abundance is a better predictor of immunotherapy response than TMB.

Although the invention has been described with reference to certain specific embodiments, various other aspects, advantages and modifications thereof will be apparent to those skilled in the art without departing from the spirit and scope of the invention as outlined in the claims appended hereto. The entire disclosures of all references recited above are incorporated herein by reference.

The invention claimed is:

1. A computer-implemented machine learning method for identifying cancer-cell specific transcriptional output for provision of immunotherapy treatment, the method comprising:
   receiving, by a processor, the nucleic acid data from one or more samples;
   determining, by the processor, variant allele fraction (VAF) of markers in ribonucleic acid (RNA) in the nucleic acid data and markers for deoxyribonucleic acid (DNA) in the nucleic acid data;
   comparing, by the processor, the VAF of the RNA relative to the DNA for each of the markers;
   quantifying, by the processor, cancer-cell specific changes in transcriptional output for each of the markers using the comparison of the VAF of the RNA relative to the DNA;
   inputting input data comprising the quantification of cancer-cell specific changes to a machine learning regression model, the machine learning regression model having been trained on input data comprising ratios of RNA relative to DNA to determine that a higher ratio of RNA relative to the DNA indicates a higher mutation burden and more aggressive cancer, the machine learning regression model generating as output data a mutation burden;
   identifying, by the processor, a response to immunotherapy treatment using the mutation burden where low mutation burden indicates non-hypermutant tumors that respond to the immunotherapy treatment; and
   outputting, by the processor, the response to immunotherapy treatment for provision of the immunotherapy treatment of cancer.

2. The method of claim 1, wherein comparing the VAF of the RNA relative to the DNA for each of the markers comprises determining a VAF difference, a VAF ratio, and an allelic ratio.

3. The method of claim 1, wherein the quantification of cancer-cell specific changes in transcriptional output comprises no elevation in cancer global transcription when the VAF indicates that the markers in the RNA and the DNA are similar, and elevation in cancer global transcription when the VAF indicates that the markers in the RNA are elevated relative to the markers in the DNA.

4. The method of claim 1, wherein the samples comprise both cancer cells and normal cells, and wherein determining the VAF in the RNA comprises measuring the cancer cells total RNA output and measuring the normal cells total RNA output.

5. The method of claim 1, wherein the markers comprise somatic single nucleotide substitutions and single nucleotide polymorphisms in regions of loss-of-heterozygosity (LOH-SNPs).

6. The method of claim 1, wherein the one or more samples come from human tumors whose RNA was derived from bulk tissue.

7. The method of claim 1, wherein the mutation burden comprises expressed mutation burden and the immunotherapy comprises immune checkpoint inhibitor (ICI) therapy.

8. The method of claim 7, wherein determining the mutation burden further comprises determining an adjusted genomic tumor mutation burden (TMB) value based on the expressed TMB using a linear regression model with the expressed TMB as a predictor variable and genomic TMB as an outcome variable.

9. The method of claim 1, wherein determining the mutation burden comprises determining non-hypermutant tumors that would respond to immunotherapy.

10. A computer-implemented machine learning system for identifying cancer-cell specific transcriptional output for provision of immunotherapy treatment, the system comprising one or more processors and a data storage, the one or more processors receiving instructions from the data storage to execute:
   an input module, executed by the processor, to receive the nucleic acid data from one or more samples;
   a machine learning based comparison module, executed by the processor, to:
      determine variant allele fraction (VAF) of markers in ribonucleic acid (RNA) in the nucleic acid data and markers for deoxyribonucleic acid (DNA) in the nucleic acid data;
      compare the VAF of the RNA relative to the DNA for each of the markers;
      quantify cancer-cell specific changes in transcriptional output for each of the markers using the comparison of the VAF of the RNA relative to the DNA;
      provide input data comprising the quantification of cancer-cell specific changes to a machine learning regression model, the machine learning regression model having been trained on input data comprising ratios of RNA relative to DNA to determine that a higher ratio of RNA relative to the DNA indicates a higher mutation burden and more aggressive cancer, the machine learning regression model generating as output data a mutation burden; and identify a response to immunotherapy treatment using the mutation burden where low mutation burden indicates non-hypermutant tumors that respond to the immunotherapy treatment; and an output module, executed by the processor, to output the response to immunotherapy treatment for provision of the immunotherapy treatment of cancer based on the response.

11. The system of claim 10, wherein comparing the VAF of the RNA relative to the DNA for each of the markers comprises determining a VAF difference, a VAF ratio, and an allelic ratio.

12. The system of claim 10, wherein the quantification of cancer-cell specific changes in transcriptional output comprises no elevation in cancer global transcription when the VAF indicates that the markers in the RNA and the DNA are similar, and elevation in cancer global transcription when the VAF indicates that the markers in the RNA are elevated relative to the markers in the DNA.

13. The system of claim 10, wherein the samples comprise both cancer cells and normal cells, and wherein determining the VAF in the RNA comprises measuring the cancer cells total RNA output and measuring the normal cells total RNA output.

14. The system of claim 10, wherein the markers comprise somatic single nucleotide substitutions and single nucleotide polymorphisms in regions of loss-of-heterozygosity (LOH-SNPs).

15. The system of claim 10, wherein the one or more samples come from human tumors whose RNA was derived from bulk tissue.

16. The system of claim 10, wherein the mutation burden comprises expressed mutation burden and the immunotherapy comprises immune checkpoint inhibitor (ICI) therapy.

17. The system of claim 16, wherein determining the mutation burden further comprises an adjusted genomic tumor mutation burden (TMB) value based on the expressed TMB using a linear regression model with the expressed TMB as a predictor variable and genomic TMB as an outcome variable.

18. The system of claim 10, wherein determining the mutation burden comprises determining non-hypermutant tumors that would respond to immunotherapy.

19. The method of claim 1, wherein low mutation burden is indicative of non-hypermutant tumors where there is less than 10 mutations-per-megabase (mut/Mb).

20. The system of claim 10, wherein low mutation burden is indicative of non-hypermutant tumors where there is less than 10 mutations-per-megabase (mut/Mb).

* * * * *